(12) United States Patent
Sher et al.

(10) Patent No.: US 7,425,550 B2
(45) Date of Patent: Sep. 16, 2008

(54) LACTAM GLYCOGEN PHOSPHORYLASE INHIBITORS AND METHOD OF USE

(75) Inventors: Philip Sher, Plainsboro, NJ (US); Gang Wu, Princeton, NJ (US); Terry Stouch, West Windsor, NJ (US); Bruce Ellsworth, Princeton, NJ (US)

(73) Assignee: Bristol-Meyers Squibb Company, Princeton, NJ (US)

( * ) Notice: Subject to any disclaimer, the term of this patent is extended or adjusted under 35 U.S.C. 154(b) by 166 days.

(21) Appl. No.: 11/352,867

(22) Filed: Feb. 13, 2006

(65) Prior Publication Data
US 2006/0128687 A1    Jun. 15, 2006

Related U.S. Application Data

(62) Division of application No. 10/440,851, filed on May 19, 2003, now Pat. No. 7,057,046.

(60) Provisional application No. 60/382,002, filed on May 20, 2002.

(51) Int. Cl.
A61K 31/554    (2006.01)
C07D 267/14    (2006.01)
C07D 498/02    (2006.01)

(52) U.S. Cl. .................. 514/211.06; 540/491

(58) Field of Classification Search ............ 514/211.06; 540/491
See application file for complete search history.

(56) References Cited

U.S. PATENT DOCUMENTS

| | | |
|---|---|---|
| 3,674,836 A | 7/1972 | Creger |
| 3,749,715 A | 7/1973 | Stein et al. |
| 3,983,140 A | 9/1976 | Endo et al. |
| 4,027,009 A | 5/1977 | Grier et al. |
| 4,231,938 A | 11/1980 | Monaghan et al. |
| 4,346,227 A | 8/1982 | Terahara et al. |
| 4,448,784 A | 5/1984 | Glamkowski et al. |
| 4,450,171 A | 5/1984 | Hoffman et al. |
| 4,499,289 A | 2/1985 | Baran et al. |
| 4,512,988 A | 4/1985 | Weller, III et al. |
| 4,613,610 A | 9/1986 | Wareing |
| 4,647,576 A | 3/1987 | Hoefle et al. |
| 4,681,893 A | 7/1987 | Roth |
| 4,686,237 A | 8/1987 | Anderson |
| 4,692,522 A | 9/1987 | Parsons et al. |
| 4,755,509 A | 7/1988 | Teulon |
| 4,759,923 A | 7/1988 | Buntin et al. |
| 4,871,721 A | 10/1989 | Biller |
| 4,924,024 A | 5/1990 | Biller |
| 5,006,530 A | 4/1991 | Angerbauer et al. |
| 5,011,930 A | 4/1991 | Fujikawa et al. |
| 5,177,080 A | 1/1993 | Angerbauer et al. |
| 5,206,235 A | 4/1993 | Fisher et al. |
| 5,260,440 A | 11/1993 | Hirai et al. |
| 5,273,995 A | 12/1993 | Roth |
| 5,354,772 A | 10/1994 | Kathawala |
| 5,385,929 A | 1/1995 | Bjorge et al. |
| 5,488,064 A | 1/1996 | Sher |
| 5,491,134 A | 2/1996 | Sher et al. |
| 5,506,219 A | 4/1996 | Robl |
| 5,541,204 A | 7/1996 | Sher et al. |
| 5,545,735 A | 8/1996 | Bochis et al. |
| 5,552,397 A | 9/1996 | Karanewsky et al. |
| 5,594,006 A | 1/1997 | Sakamoto et al. |
| 5,594,016 A | 1/1997 | Ueno et al. |
| 5,595,872 A | 1/1997 | Watterau, II et al. |
| 5,612,359 A | 3/1997 | Murugesan |
| 5,614,492 A | 3/1997 | Habener |
| 5,652,363 A | 7/1997 | Khanna et al. |
| 5,686,104 A | 11/1997 | Mills et al. |
| 5,691,322 A | 11/1997 | Robl |
| 5,712,279 A | 1/1998 | Biller et al. |
| 5,712,396 A | 1/1998 | Magnin et al. |
| 5,719,278 A | 2/1998 | Albright et al. |
| 5,739,135 A | 4/1998 | Biller et al. |
| 5,753,675 A | 5/1998 | Wattanasin |
| 5,760,246 A | 6/1998 | Biller et al. |
| 5,770,615 A | 6/1998 | Cheng et al. |
| 5,776,983 A | 7/1998 | Washburn et al. |

(Continued)

FOREIGN PATENT DOCUMENTS

EP    0142146    5/1985

(Continued)

OTHER PUBLICATIONS

Albright, J.D. et al., "Synthesis of 1,4,5,6-Tetrahydropyrazolo[3,4-d]pyrido[3,2-b]azepine", J. Heterocyclic Chem., vol. 37, pp. 41-46 (2000).

(Continued)

*Primary Examiner*—Taofiq A Solola
(74) *Attorney, Agent, or Firm*—Burton Rodney

(57) ABSTRACT

A compound of formula I is provided having the structure

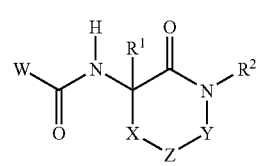

wherein
  W is as defined herein;
  X is —CHR$^5$O—;
  Y is a bond;
  Z is an aryl or heteroaryl group; and
  R$^1$, and R$^2$, are as described herein.

Further provided is a method for treating diabetes and related diseases employing the above compound, either alone or in combination with another therapeutic agent.

20 Claims, No Drawings

U.S. PATENT DOCUMENTS

| | | | |
|---|---|---|---|
| 5,789,587 | A | 8/1998 | Fisher et al. |
| 5,827,875 | A | 10/1998 | Dickson, Jr. et al. |
| 5,849,918 | A | 12/1998 | Esser et al. |
| 5,885,983 | A | 3/1999 | Biller et al. |
| 5,952,322 | A | 9/1999 | Hoover et al. |
| 5,962,440 | A | 10/1999 | Sulsky |
| 6,017,926 | A | 1/2000 | Askew et al. |
| 6,043,265 | A | 3/2000 | Murugesan et al. |

FOREIGN PATENT DOCUMENTS

| | | |
|---|---|---|
| EP | 0160546 | 11/1985 |
| EP | 0107095 | 9/1987 |
| EP | 0416740 | 3/1991 |
| EP | 0978279 | 2/2000 |
| EP | 1088824 | 4/2001 |
| EP | 1177791 | 2/2002 |
| FR | 2596363 | 10/1987 |
| GB | 2205837 | 12/1988 |
| JP | 8-259447 | 10/1996 |
| JP | 2000-256318 | 9/2000 |
| WO | WO 86/03488 | 6/1986 |
| WO | WO 86/07054 | 12/1986 |
| WO | WO 93/14067 | 7/1993 |
| WO | WO 97/21993 | 9/1993 |
| WO | WO 96/36596 | 11/1996 |
| WO | WO 96/38144 | 12/1996 |
| WO | WO 96/39384 | 12/1996 |
| WO | WO 96/39385 | 12/1996 |
| WO | WO 97/12613 | 4/1997 |
| WO | WO 97/12615 | 4/1997 |
| WO | WO 97/43268 | 11/1997 |
| WO | WO 99/00353 | 1/1999 |
| WO | WO 99/26659 | 6/1999 |
| WO | WO 99/38501 | 8/1999 |
| WO | WO 99/43663 | 9/1999 |
| WO | WO 99/46272 | 9/1999 |
| WO | WO 99/61431 | 12/1999 |
| WO | WO 99/67278 | 12/1999 |
| WO | WO 99/67279 | 12/1999 |
| WO | WO 00/01389 | 1/2000 |
| WO | WO 00/47206 | 8/2000 |
| WO | WO 00/59506 | 10/2000 |
| WO | WO 01/00586 | 1/2001 |
| WO | WO 01/21602 | 3/2001 |
| WO | WO 01/27128 | 4/2001 |

OTHER PUBLICATIONS

Aranyos, A. et al., "Novel Electron-Rich Phosphine Ligands Facilitate the Palladium-Catalyzed Preparation of Diaryl Ethers", J. Am. Chem. Soc., vol. 121, pp. 4369-4378 (1999).

Arbeeny, C. et al., "The Metabolic Syndrome: From Pathophysiology to Novel Treatment Strategies", Curr. Med. Chem.—Imm., Endoc. & Metab. Agents, vol. 1, No. 1, pp. 1-24 (2001).

Armstrong, III, J.D. et al., "An Efficient Asymmetric Synthesis of (R)-3-Amino-2,3,4,5-tetrahydro-1H-[1]benzazepin-2-one", Tetrahedron Letters, vol. 35, No. 20, pp. 3239-3242 (1994).

Ashworth, D.M. et al., "2-Cyanopyrrolidides as Potent, Stable Inhibitors of Dipeptidyl Peptidase IV", Bioorganic & Medicinal Chemistry Letters, vol. 6, No. 10, pp. 1163-1166 (1996).

Ball, J.B. et al., Syntheses and Conformational Analyses of Some 3-Amino-2,5-dioxo-2,3,4,5-tetrahydro-1H-1-benzazepine Derivatives, etc., J. Heterocyclic Chem., vol. 27, pp. 279-286 (1990).

Bell, I.M. et al., "Development of Orally Active Oxytocin Antagonists, etc.", J. Med. Chem., vol. 41, No. 12, pp. 2146-2163 (1998).

Berg-Nielsen, K. et al., "Amino-Claisen Rearrangement of Vinyl Propargylamines and Pryindane Synthesis from a Divinyl Ketone", Acta Chemica Scandinavica B, vol. 32, pp. 553-556 (1978).

Biller, S.A. et al., "Isoprenoid (Phosphinylmethyl)phosphonates as Inhibitors of Squalene Synthetase", Journal of Medicinal Chemistry, vol. 31, No. 10, pp. 1869-1871 (1988).

Biller, S.A. et al., "Squalene Synthase Inhibitors", Current Pharmaceutical Design, vol. 2, No. 1, pp. 1-40 (1996).

Bundgaard, H., ed., Design of Prodrugs, Elsevier Science Publishers B.V., publ. (1985) (table of contents).

Caprathe, B.W. et al., "Dopamine Autoreceptor Agonists as Potential Antipsychotics. 3. 6-Propyl-4,5,5a,6,7,8-hexahydrothiazolo[4,5-f]quinolin-2-amine", J. Med. Chem., vol. 34, pp. 2736-2746 (1991).

Capson, T.L., "Synthesis and Evaluation of Ammonium Analogs of Carbocationic Intermediates in Squalene Biosynthesis", dissertation, Department of Medicinal Chemistry, University of Utah, pp. iv-v, table of contents, 16-17, 40-43, 48-51, Summary (Jun. 1987).

Carling, R.W. et al., "3-Nitro-3,4-dihydro-2(1H)-quinolones. Excitatory Acid Antagonists Acting at Glycine-Site NMDA, etc.", J. Med. Chem., vol. 36, No. 22, pp. 3397-3408 (1993).

Casimir, J.R. et al., "Efficient Synthesis of (S)-4-Phthalimido-1,3,4,5- tetrahydro-8-(2,6-dichlorobenzyloxy)-3-oxo-2-benzazepin-2-acetic Acid (Pht-Hba(2,6-Cl$_2$-Bn)-Gly-OH)", J. Org. Chem., vol. 65, pp. 6487-6492 (2000).

Corey, E.J. et al., "Application of Unreactive Analogs of Terpenoid Pyrophosphates to Studies of Multistep Biosynthesis. Demonstration That 'Presqualene Pyrophosphate' Is an Essential Intermediate on the Path to Squalene", J. Am. Chem. Soc., vol. 98, No. 5, pp. 1291-1293 (1976).

Cornicelli, J.A. et al., "15-Lipoxygenase and Its Inhibition: A Novel Therapeutic Target for Vascular Disease", Current Pharmacteuical Design, vol. 5, No. 1, pp. 11-20 (1999).

Davis, A.L. et al., "Preparation and Antimicrobial Properties of the D and L Forms of 3-Amino-3,4-dihydro-1-hydroxycarbostyril", Journal of Medicinal Chemistry, vol. 15, No. 3, pp. 325-327 (1972).

Davis, A.L. et al., "Synthesis of the 3-Methyl and 4-Methyl Derivatives of 3-Amino-3,4-dihydro-1-hydroxycarbostyril and Related Compounds", J. Heterocyclic Chem., vol. 17, pp. 1405-1408 (1980).

Davis, A.L. et al., "The Syntheses and Biological Activities of o-Aminophenylalanine and Related Compounds", Archives of Biochemistry and Biophysics, vol. 102, pp. 48-51 (1963).

DeVita, R.J. et al., "Heterocyclic Analogs of the Benzolactam Nucleus of the Non-Peptidic Growth Hormone Secretagogue L-692,429", Bioorganic & Medicinal Chemistry Letters, vol. 5, No. 12, pp. 1281-1286 (1995).

El-Subbagh, H.I. et al., "Synthesis and Antitumor Activity of Some New Substituted Quinolin-4-one and 1,7-Naphthyridin-4-one Analogs", Arch. Pharm. Pharm. Med. Chem., vol. 332, pp. 19-24 (1999).

Epsztajn, J. et al., "Applications of Organolithium and Related Reagents in Synthesis. Part 3. A General Study of the Reaction of Lithium Alkyls with Pyridine Ketones", J. Chem. Soc. Perkin Trans. I, pp. 213-219 (1985).

Ferraris, D. et al., "Catalytic, Enantioselective Alkylation of α-Imino Esters: The Synthesis of Nonnatural α-Amino Acid Derivatives", J. Am. Chem. Soc., vol. 124, No. 1, pp. 67-77 (2002).

Flynn, G.A. et al., "An Acyliminium Ion Route to Cis and Trans 'Anti' Phe-Gly Dipeptide Mimetics", Bioorganic & Medicinal Chemistry Letters, vol. 1, No. 6, pp. 309-312 (1991).

Ford, E.S. et al., "Prevalence of the Metabolic Syndrome Among US Adults: Findings From the Third National Health and Nutrition Examination Survey," JAMA, vol. 287, No. 3, pp. 356-359 (2002).

Fujita, M. et al., "A Novel, Covenient Synthesis of 2-Aryl-3-oxo-3,4-dihydro-2H-1,4-benzothiazines", Synthesis, pp. 599-604 (1988).

Ghiselli, G., "The Pharmacological Profile of FCE 27677: A Novel ACAT Inhibitor with Potent Hypolipidemic Activity Mediated by Selective Suppression of the Hepatic Secretion of ApoB-100-Containing Lipoprotein", Cardiovascular Drug Reviews, vol. 16, No. 1, 16-30 (1998).

Greene, T.W. et al., Protective Groups in Organic Sythesis, Second Edition, John Wiley & Sons, Inc., publ., pp. ix-x (table of contents) (1991).

Hamann B.C. et al., "Sterically Hindered Chelating Alkyl Phosphines Provide Large Rate Accelerations in Palladium-Catalyzed Amination of Aryl Iodides, Bromides, and Chlorides, etc.", J. Am. Chem. Soc., vol. 120, pp. 7369-7370 (1998).

Hara, S., "Ileal Na$^+$/bile acid cotransporter inhibitors", Drugs of the Future, vol. 24, No. 4, pp. 425-430 (1999).

Hoover, D.J. et al., "Indole-2-carboxamide Inhibitors of Human Liver Glycogen Phosphorylase", J. Med. Chem., vol. 41, pp. 2934-2938 (1998).

Huang, Y. et al., "The Improved Preparation of 7,8-dihydroquinoline-5(6H)-one and 6,7-dihydro-5H-1-pyridine-5-one", Synthetic Communications, vol. 28, No. 7, pp. 1197-1200 (1998).

Hughes, T.E. et al., "(1-[[[2-[5-Cyanopyridin-2-yl)amino]ethyl]amino]acetyl]-2-cyano-(S)-pyrrolidine) a Slow-Binding Inhibitor of Dipeptidyl Peptidase IV", Biochemistry, vol. 38, pp. 11597-11603 (1999).

Itoh, K. et al., "Synthesis and Angiotensin Converting Enzyme Inhibitory Activity of 1,5-Benzothiazepine and 1,5-Benzoxazepine Derivatives. I", Chem. Pharm. Bull., vol. 34, pp. 1128-1147 (1986).

Jackson, R.F.W. et al., "Concise Synthesis of Enantiomerically Pure Phenylalanine, Homophenylalanine, and Bishomophenylalanine Derivatives Using Organozinc Chemistry, etc.", J. Org. Chem., vol. 63, pp. 7875-7884 (1998).

Jössang-Yanagida, A. et al., "Tetrahydropyridoazepines and Tetrahydropyridoazepinones from the Corresponding Dihydroquinolones", J. Heterocyclic Chem., vol. 15, pp. 249-251 (1978).

Kikeji, D. et al., "A Convenient Synthesis of 3,4-Dihydro-2-methyl-3-oxo-2H-1,4-benzoxazine-2-carboxylic Acids and 3,4-Dihydro-2-methyl-3-oxo-2-H-pyrido[3,2-b]-1,4-oxazine-2-carboxylic Acid", J. Heterocyclic Chem., vol. 30, pp. 597-602 (1993).

Kluge, M. et al., "Syntheses for 2-Amino and 2-Mercapto-2H-1,4-benzoxazin-3(4H)-one and 2H-1,4-Benzothiazin-3(4H)-one as Aza and Thio Analogues of the Natural Product Blepharigenin", J. Heterocyclic Chem., vol. 33, pp. 1623-1626 (1996).

Krause, B.R. et al., "Chapter 6: ACAT Inhibitors: Physiologic Mechanisms for Hypolipidemic and Anti-Atherosclerotic Activities in Experimental Animals", Inflammation: Mediators Pathways, CRC Press, Inc., publ., Ruffolo, Jr., R.R. and Hollinger, M.A., eds., pp. 173-198 (1995).

Lardenois, P. et al., "A Convenient Synthesis of 7,8-dihydroisoquinolin-5-(6H)-one", Synthetic Communications, vol. 26, No. 12, pp. 2305-2308 (1996).

Larock, R.C., Comprehensive Organic Transformations: A Guide to Functional Group Preparations, VCH Publishers, Inc., publ., pp. xiii-xxviii (table of contents) (1989).

Lowe, III, J.A. et al., "5-Phenyl-3-ureidobenzazepin-2-ones as Cholecystokinin-B Receptor Antagonists", J. Med. Chem., vol. 37, pp. 3789-3811 (1994).

Martin, W.H. et al., "Discovery of a human liver glyocgen phosphorylase inhibitor that lowers blood glucose in vivo", Proc. Natl. Acad. Sci. USA, vol. 95, pp. 1776-1781 (1998).

McCord, T.J. et al., "The Synthesis, Configuration, and conformation of cis- and trans-3-Amino-3,4-dihydro-1-hydroxy-4-methylcarbostyrils and Other Configurationally Related Compounds", J. Heterocyclic Chem., vol. 18, pp. 1035-1039 (1981).

Morton, G.C. et al., "Novel solid-phase synthesis of 1,5-benzothiazepine-4-one derivatives", Tetrahedron Letters, vol. 41, pp. 3029-3033 (2000).

Murakami, K. et al.,"A Novel Insulin Sensitizer Acts as a Coligand for Peroxisome Proliferator-Activated Receptor-α (PPAR-α) and PPAR-γ", etc., Diabetes, vol. 47, pp. 1841-1847 (1998).

Murakami, Y. et al., "1,3-Disubstituted Benzazepines as Novel, Potent, Selective Neuropeptide Y Y1 Receptor Antagonists", J. Med. Chem., vol. 42, pp. 2621-2632 (1999).

Nicolosi, R.J. et al., "The ACAT inhibitor, CI-1011 is effective in the prevention and regression of aortic fatty streak area in hamsters", Atherosclerosis, vol. 137, pp. 77-85 (1998).

Ortiz de Montellano, P.R. et al., "Inhibition of Squalene Synthetase by Farnesyl Pyrophosphate Analogues", Journal of Medicinal Chemistry, vol. 20, No. 2, pp. 243-249 (1977).

Parsons, W.H. et al., "Benzolactams. A.New.Class of Converting Enzyme Inhibitors", Biochemical and Biophysical Research Communications, vol. 117, No. 1, pp. 108-113 (1983).

Rabi-Barakay, A. et al., "Intramolecular Amidoalkylation of Aromatics III. Synthesis of Conformationally Restricted Bridged Peptide Analogues of Phe-Gly", Tetrahedron, vol. 50, No. 36, pp. 10771-10782 (1994).

Robl, J.A. et al., "Dual Metalloprotease Inhibitors. I. Constrained Peptidomimetics of Mercaptocyl Dipeptides", Bioorganic & Medicinal Chemistry Letters, vol. 4, No. 15, pp. 1789-1794 (1994).

Rosenblum, S.B. et al., "Discovery of 1-(4-Fluorophenyl)-(3R)-[3-(4-fluorophenyl)-(3S)-hydroxypropyl]-(4S)-(4-hydroxyphenyl)-2-azetidinone (SCH 58235), etc.", J. Med. Chem., vol. 41, pp. 973-980 (1998).

Saari, W.S. et al., "Synthesis and Evaluation of 2-Pyridinone Derivatives as HIV-1-Specific Reverse Transcriptase Inhibitors. 2. Analogues of 3-Aminopyridin-2(1H)-one", J. Med. Chem., vol. 35, pp. 3792-3802 (1992).

Salisbury, B.G. et al., "Hypocholesterolemic activity of a novel inhibitor of cholesterol absorption, SCH 48461", Atherosclerosis, vol. 115, pp. 45-63 (1995).

Salvino, J.M. et al., "Polymer-Supported Tetrafluorophenol: A New Activated Resin for Chemical Library Synthesis", J. Comb. Chem., vol. 2, pp. 691-697 (2000).

Schoen, W.R. et al., "A Novel 3-Substituted Benzazepinone Growth Hormone Secretagogue (L-692,429)", J. Med. Chem., vol. 37, pp. 897-906 (1994).

Sendobry, S.M. et al., "Attenuation of diet-induced atherosclerosis in rabbits with a highly selective 15-lipoxygenase inhibitor lacking significant antioxidant properties", British Journal of Pharmacology, vol. 120, pp. 1199-1206 (1997).

Sicker, D. et al., "A Convenient Synthesis of Heterocyclic N-Hydroxylactams", Synthesis, pp. 331-333 (1985).

Sicker, D. et al., "Synthesis for 2-Hydroxy-2H-1,4-benzothiazin-3(4H)-one Derivatives as Thio Analogues of Natural Hemiacetals", J. Heterocyclic Chem., vol. 31, pp. 809-812 (1994).

Slade, J. et al., "Angiotensin Converting Enzyme Inhibitors: 1,5-Benzothiazepine Derivatives", J. Med. Chem., vol. 28, pp. 1517-1521 (1985).

Sliskovic, D.R. et al., "ACAT Inhibitors: Potential Anti-atherosclerotic Agents", Current Medicinal Chemistry, vol. 1, pp. 204-225 (1994).

Smith, C. et al., "RP 73163: A Bioavailable Alkylsulphinyl-Diphenylimidazole ACAT Inhibitor", Bioorganic & Medicinal Chemistry Letters, vol. 6, No. 1, pp. 47-50 (1996).

Smith, M.B., Compendium of Organic Synthetic Methods, vol. 11, John Wiley & Sons, Inc., publ., p. v (table of contents), (2003).

Stout, D.M., "Inhibitors of Acyl-CoA:Cholesterol O-Acyl Transferase (ACAT) as Hypocholesterolemic Agents. 6. The First Water-Soluble ACAT Inhibitor with Lipid-Regulating Activity, etc.", Chemtracts-Organic Chemistry, vol. 8, pp. 359-362 (1995).

Tamura, S.Y. et al., "Novel Benzo-Fused Lactam Scaffolds as Factor Xa Inhibitors", Bioorganic & Medicinal Chemistry Letters, vol. 9, pp. 2573-2578 (1999).

Tietze, L.F. et al., "First Sythesis and Structural Determination of Blepharin and 1'-Epiblepharin", Synthesis, pp. 1118-1120 (1991).

Turconi, M. et al., "Synthesis, Absolute Configuration, Conformational Analysis and Binding Affinity Properties of Enantiomeric Forms of DAU 5750, a Novel M1-M3 Muscarinic Receptor Antagonist", Bioorganic & Medicinal Chemistry, vol. 2, No. 12, pp. 1375-1383 (1994).

van Niel, M.B. et al., "CCK$_B$ Selective Receptor Ligands: Novel 1,3,5-Trisubstituted Benzazepin-2-ones", Bioorganic & Medicinal Chemistry Letters, vol. 5, No. 13, pp. 1421-1426 (1995).

Watthey, J.W.H. et al., "Synthesis and Biological Properties of (Carboxyalkyl)amino-Substituted Bicyclic Lactam Inhibitors of Angiotensin Converting Enzyme", J. Med. Chem., vol. 28, pp. 1511-1516 (1985).

Wermuth, C.G. et al., "Character 31: Designing Prodrugs and Bioprecursors I: Carrier Prodrugs", The Practice of Medicinal Chemistry, Academic Press, publ., Wermuth, C.G., ed., pp. 671-696 (1996).

Worley, J.W. et al., "2-Diakylphosphonyl- and 2-Alkylidene-3,4-dihydro-3-oxo-2H-1,4-benzothiazines", J. Org. Chem., vol. 40, No. 12, pp. 1731-1734 (1975).

Yamada, M. et al., "A Potent Dipeptide Inhibitor of Dipeptidyl Peptidase IV", Bioorganic & Medicinal Chemistry Letters, vol. 8, pp. 1537-1540 (1998).

Bundgaard, H., "Chapter 5: Design and Application of Prodrugs", A Textbook of Drug Design and Development, Harwood Academic Publishers, publ., Krogsgaard-Larsen, P. and Bundgaard, H., eds., pp. 113-191 (1991).

Fu, Y. et al., "Sterically Hindered $C^{\alpha\alpha}$-Disubstituted α-Amino Acids: Synthesis from α-Nitroacetate and Incorporation into Peptides", J. Org. Chem., vol. 66, pp. 7118-7124 (2001).

Ashworth, D.M. et al., "2-Cyanothiazolides as Very Potent, Stable Inhibitors of Dipeptidyl Peptidase IV", Bioorganic & Medicinial Chemistry Letters, vol. 6, No. 22, pp. 2745-2748 (1996).

McClard, R.W. et al., "Novel Phosphonylphosphinyl (P-C-P-C-) Analogues of Biochemically Interesting Diphosphates. Syntheses and Properties of P-C-P-C- Analogues of Isopentenyl Diphosphate and Dimethylallyl Diphosphate", J. Am. Chem. Soc., vol. 109, pp. 5544-5545 (1987).

Sorbera, L.A. et al., "Avasimibe: Treatment of Lipoprotein Disorders, ACAT Inhibitor", Drugs of Future, vol. 24, No. 1, pp. 9-15 (1999).

LACTAM GLYCOGEN PHOSPHORYLASE INHIBITORS AND METHOD OF USE

CROSS-REFERENCE TO RELATED APPLICATION

This application is a divisional of U.S. patent application Ser. No. 10/440,851, filed May 19, 2003 now U.S. Pat. No. 7,057,046, that claims the benefit of U.S. Provisional Application No. 60/382,002, filed May 20, 2002, which are incorporated herein by reference in its entirety.

FIELD OF THE INVENTION

The present invention relates to novel lactam compounds which are inhibitors of glycogen phosphorylase. Further, the present invention relates to methods for using such compounds and to pharmaceutical compositions containing such compounds.

BACKGROUND OF THE INVENTION

Approximately 100 million people worldwide suffer from type II diabetes, which is typically characterized by hyperglycemia due to excessive hepatic glucose production and peripheral insulin resistance, the root causes for which are as yet unknown. Hyperglycemia is considered to be the major risk factor for the development of diabetic complications, such as retinopathy, neuropathy, nephropathy and macrovascular disease.

Accordingly, hepatic glucose production is an important potential target for type II diabetes therapy. The liver produces glucose by glycogenolysis (breakdown of the glucose polymer glycogen) and gluconeogenesis (synthesis of glucose from 2- and 3-carbon precursors). Particularly, glycogenolysis is catalyzed in the liver, muscle and brain by tissue-specific isoforms of the enzyme glycogen phosphorylase. Prior studies suggest that glycogenolysis may make an important contribution to hepatic glucose output in type II diabetes. See WO 96/39384; WO 96/39385; EP 978279; Proc. Natl. Acad. Sci. USA 1998, 95, 1776-1781; J. Med. Chem. 1998, 41, 2934-2938. Thus, glycogen phosphorylase inhibitors are believed to be a useful therapeutic agent for treating type II diabetes and delaying the onset of diabetic complications by decreasing hepatic glucose production and lowering glycemia, while providing minimal risk of hypoglycemia and weight gain. See Id.

In recent years diabetes has been recognized as a component of Syndrome X (Metabolic or Dysmetabolic Syndrome), which consists of two or more of the often associated disorders—diabetes, hypertension, dyslipidemia (hypertriglyceridemia, low HDL and/or hypercholesterolemia) and obesity. Syndrome X is understood to result from the complex interplay of several metabolic, hormonal and physiologic abnormalities. Key among these is the hyperinsulinemia that often accompanies diabetes and has been associated with hypertension. It has been suggested that hypertension may be result in part from abnormal vascular growth and/or renal sodium retention caused by hyperinsulinemia. Because hyperinsulinemia is a compensatory response to hyperglycemia, treatments for diabetes that work by raising insulin levels (insulin, insulin secretagogues) treat hyperglycemia at the possible expense of promoting hypertension. However, treatments for diabetes operating by other mechanisms may decrease the need for insulin, thus ameliorating hyperinsulinemia and thereby potentially reducing the risk or progression of hypertension. The efficacy of glycogen phosphorylase inhibitors in lowering blood sugar is not dependent upon the production or delivery of insulin. Therefore, glycogen phosphorylase inhibitors may be effective in ameliorating hyperinsulinemia, while reducing the risk or progression of hypertension.

Both hypertension and glucose intolerance (hyperinsulinemia after a meal) are known to be independent risk factors for another component of Syndrome X, dyslipidemia. Therefore, treatments for diabetes that address hyperglycemia and reduce the need for insulin, such as glycogen phosphorylase inhibitors, offer the opportunity to treat not only diabetes and hypertension, but potentially dyslipidemia as well.

Further, glycogen phosphorylase inhibitors have been shown to decrease appetite for high fat foods in animal models of obesity (see WO 00/47206), and may thus be useful in the treatment of human obesity.

Therefore, by decreasing appetite for high fat foods, and by treating hyperglycemia without delivering or causing the production of insulin, glycogen phosphorylase inhibitors may be useful in treating or preventing, either directly or indirectly, all of the components of Syndrome X—diabetes, hypertension, dyslipidemia and obesity. See WO 96/39384, WO 96/39385, WO 00/47206.

Since the elements of Syndrome X are all risk factors for atherosclerosis and cardiovascular disease, glycogen phosphorylase inhibitors may be useful in treating, preventing or slowing the progression of atherosclerosis and cardiovascular disease.

Furthermore, atherosclerosis and cardiovascular disease increase the risk of ischemic events, both cardiac and non-cardiac, and both during normal day-to-day activities and in the perioperative setting. Glycogen phosphorylase inhibitors have been shown to reduce tissue damage during ischemic events (see U.S. Pat. No. 5,952,322, WO 99/43663, WO 96/39384, WO 96/39385), and therefore may be of use in minimizing the adverse impact of this often encountered consequence of atherosclerosis and cardiovascular disease.

SUMMARY OF THE INVENTION

In accordance with the present invention, lactam compounds are provided that have the general structure of formula I

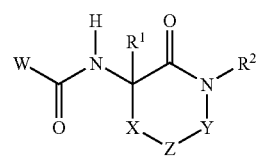

wherein
W is a bicyclic hetroaryl of the structure

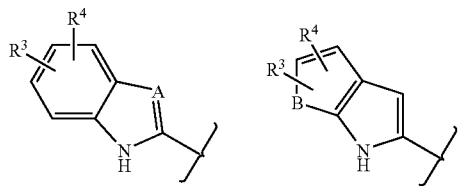

-continued

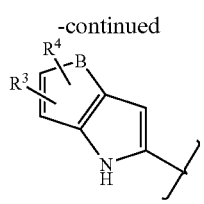

X is —O—, —S—, —SO$_2$—, —CHR$^5$—, —CHR$^5$O—, —CHR$^5$S—, —CHR$^5$SO$_2$—, —CHR$^5$CO— or —CH$_2$CHR$^5$—;

Y is a bond or —CHR$^6$—;

Z is an aryl or heteroaryl group of the following structure:

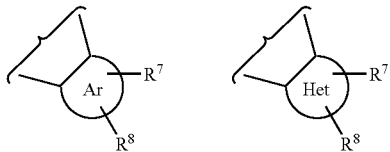

A is —CH— or —N—;
B is —O— or —S—;
R$^1$ is hydrogen, alkyl, aryl or alkenyl;
R$^2$ is hydrogen, alkyl, aryl, arylalkyl, heteroarylalkyl or alkenyl;
R$^3$ and R$^4$ are each independently hydrogen, halo, trifluoromethyl, cyano, alkyl or alkoxy;
R$^5$ and R$^6$ are each independently hydrogen, alkyl, aryl, alkenyl, CN, CN$_4$R$^{9A}$ (tetrazole), CO$_2$R$^{9A}$, CONR$^{9A}$R$^{9B}$ or CONR$^{9A}$OR$^{9B}$;
R$^7$ and R$^8$ are each independently hydrogen, halo, trifluoromethyl, cyano, hydroxy, a hydrogen bonding group, alkyl, alkoxy, aryl, arylalkyl, heteroarylalkyl, aryloxy or alkenyl; and
R$^{9A}$ and R$^{9B}$ are independently hydrogen, alkyl, arylalkyl, heteroarylalkyl or aryl, or R$^{9A}$ and R$^{9B}$ may optionally be cyclized together to form a ring, wherein said ring may further be substituted with one to three additional hydrogen bonding groups;

wherein when R$^1$, R$^2$, R$^5$, R$^6$, R$^7$ and R$^8$ are alkyl, aryl, alkenyl, arylalkyl, heteroarylalkyl, alkoxy or aryloxy, R$^1$, R$^2$, R$^5$, R$^6$, R$^7$ and R$^8$ may each independently be substituted with 1 to 3 hydrogen bonding groups.

The compounds of formula I above further include all pharmaceutically acceptable salts, stereoisomers and prodrug esters of formula I.

Preferably, Z is an aryl or heteroaryl group of the structure

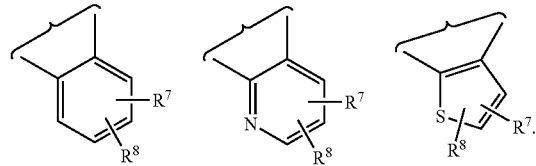

The hydrogen bonding group substitutent is preferably selected from the group consisting of OR$^{9A}$, OCO$_2$R$^{10}$, OCONR$^{9A}$R$^{9B}$, CN, NO$_2$, CN$_4$R$^{9A}$ (tetrazole), COCF$_3$, COR$^{9A}$, CO$_2$R$^{9A}$, CONR$^{9A}$R$^{9B}$, CONR$^{9A}$OR$^{9B}$, C(NR$^{9A}$)NR$^{9B}$R$^{9C}$, CONR$^{9A}$SO$_2$R$^{9B}$, SOR$^{10}$, SO$_2$R$^{10}$, SO$_3$H, SO$_2$NR$^{9A}$R$^{9B}$, SO$_2$NR$^{9A}$COR$^{9B}$, SO$_2$NR$^{9A}$CONR$^{9B}$R$^{9C}$, POR$^{9A}$R$^{9B}$, PO$_2$R$^{9A}$R$^{9B}$, PO$_3$R$^{9A}$R$^{9B}$, PO$_2$R$^{9A}$NR$^{9B}$R$^{9C}$, NR$^{9A}$R$^{9B}$, NR$^{9A}$COR$^{9B}$, NR$^{9A}$C(NR$^{9B}$)R$^{9C}$, NR$^{9A}$CO$_2$R$^{9B}$, NR$^{9A}$CONR$^{9B}$R$^{9C}$, NR$^{9A}$C(NR$^{9B}$)NR$^{9C}$R$^{9D}$, NR$^{9A}$SO$_2$R$^{9B}$, NR$^{9A}$CONR$^{9B}$ SO$_2$R$^{9C}$, NR$^{9A}$SO$_2$NR$^{9B}$R$^{9C}$, NR$^{9A}$POR$^{9B}$R$^{9C}$, NR$^{9A}$PO$_2$R$^{9B}$R$^{9C}$, NR$^{9A}$PO$_3$R$^{9B}$R$^{9C}$ and NR$^{9A}$PO$_2$R$^{9B}$NR$^{9C}$R$^{9D}$;

wherein
R$^{9C}$ and R$^{9D}$ are each independently hydrogen, alkyl, arylalkyl, heteroarylalkyl or aryl; and
R$^{10}$ is independently alkyl, arylalkyl, heteroarylalkyl, or aryl;
wherein R$^{9A}$, R$^{9B}$, R$^{9C}$, R$^{9D}$ or R$^{10}$ may further be substituted with one to three additional hydrogen bonding groups;
and wherein
two of R$^{9A}$, R$^{9B}$, R$^{9C}$ or R$^{9D}$ within the same hydrogen bonding group may optionally be cyclized together to form a ring, wherein said ring may further be substituted with one to three additional hydrogen bonding groups.

Preferred embodiments include compounds of formula I wherein
R$^1$ is hydrogen;
z is

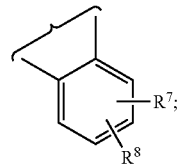

and
W is

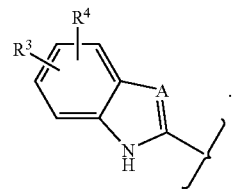

Additional embodiments include compounds of formula I where
R$^1$ is hydrogen;
Z is

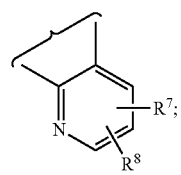

and
W is

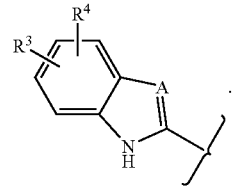

More preferably, W is 5-chloroindol-2-yl.
Further preferred embodiments include compounds of formula I, wherein
X is —CHR$^5$—, —CHR$^5$O—, —CHR$^5$S—, —CHR$^5$SO$_2$—, —CHR$^5$CO— or —CH$_2$CHR$^5$—;
Y is —CHR$^6$—; and
R$^5$ or R$^6$ are CO$_2$H.

Additional embodiments include compounds of formula I wherein when R$^1$, R$^2$, R$^5$, R$^6$, R$^7$ and R$^8$ are alkyl, aryl, alkenyl, arylalkyl, heteroarylalkyl, alkoxy or aryloxy, at least one of $R^1$, $R^2$, $R^5$, $R^6$, $R^7$ or $R^8$ are substituted with $CO_2H$.

The compounds of formula I inhibit the activity of the enzyme glycogen phosphorylase. Consequently, the compounds of the present invention may be used in the treatment of multiple diseases or disorders associated with glycogen phosphorylase activity, such as the treatment of diabetes, the micro- and macrovascular complications associated with diabetes, such as retinopathy, neuropathy, nephropathy, as well as hyperglycemia, hypertension, hypertriglyceridemia, dislipidemia, Syndrome X, obesity, hyperinsulinemia, diabetic complications, atherosclerosis, cardiovascular disease, ischemia, delayed wound healing, infection, cancer and other diseases.

The present invention provides for compounds of formula I, pharmaceutical compositions employing such compounds and for methods of using such compounds. In particular, the present invention provides a pharmaceutical composition comprising a therapeutically effective amount of a compound of formula I, alone or in combination with a pharmaceutically acceptable carrier.

Further, in accordance with the present invention, a method is provided for preventing, inhibiting or treating the progression or onset of diseases or disorders associated with the activity of the enzyme glycogen phosphorylase, such as defined above and hereinafter, wherein a therapeutically effective amount of a compound of formula I is administered to a mammalian, i.e., human, patient in need of treatment.

The compounds of the invention can be used alone, in combination with other compounds of the present invention, or in combination with one or more other agent(s).

Further, the present invention provides a method for preventing, inhibiting or treating the diseases as defined above and hereinafter, wherein a therapeutically effective amount of a combination of a compound of formula I and another compound of formula I and/or at least one other type of therapeutic agent, is administered to a mammalian, i.e., human patient in need of treatment.

Other compounds of the invention include compounds of formula I, as described above, excluding:

(a) compounds having the structure

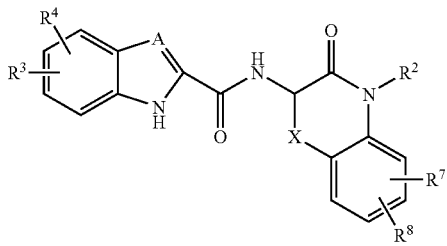

wherein the following occur simultaneously;

$R^2$ is substituted or unsubstituted $C_1$-$C_8$ alkyl, where the $C_1$-$C_8$ alkyl substitutent(s) is/are selected from the group consisting of $C_1$-$C_4$ alkyloxy, $C_1$-$C_4$ alkylamino, unsubstituted or mono-, di-, or trisubstituted $C_6$ or $C_{10}$ aryloxy, unsubstituted or mono-, di-, or, trisubstituted $C_6$ or $C_{10}$ aryl, and unsubstituted or mono-, di-, or tri-substituted $C_3$-$C_9$ heteroaryl, wherein the substituent(s) on the $C_6$ or $C_{10}$ aryloxy, the $C_6$ or $C_{10}$ aryl and the heteroaryl are selected from hydroxy, $C_1$-$C_4$ alkoxy, amino or mono- or di-$C_1$-$C_4$ alkyl-amino;

$R^3$ and $R^4$ are hydrogen, halo, $C_1$-$C_8$ alkyl or $C_1$-$C_8$ alkoxy;

$R^7$ and $R^8$ are hydrogen, halo, hydroxy, $C_1$-$C_8$ alkyl or $C_1$-$C_8$ alkoxy, where at least one of $R_7$ or $R_8$ is hydrogen; and X is —$CH_2$— or —$CH_2CH_2$—; and A is —CH— or —N—, (b) compounds having the structure

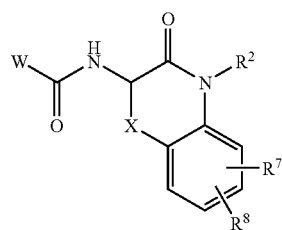

wherein the following occur simultaneously;

W is a bicyclic heteroaryl of the structure

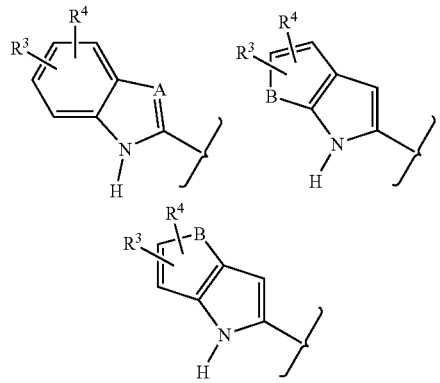

X is —$CHR^5O$—, —$CHR^5S$—, —$CHR^5CO$— or —$CH_2CHR^5$—;

A is —CH— or —N—;

B is —O— or —S—;

$R^2$ is hydrogen, $CH_2CONR^{14}R^{15}$ or $CHCO_2R^{16}$;

$R^3$ and $R^4$ are independently hydrogen, halogen, $C_1$-$C_6$ alkyl or $C_1$-$C_6$ alkoxy;

$R^5$ is hydrogen, alkyl or aryl;

$R^7$ and $R^8$ are independently hydrogen, halogen, alkyl or alkoxy;

$R^{14}$ and $R^{15}$ are independently hydrogen, alkyl or arylalkyl; and $R^{16}$ is alkyl or arylalkyl, (c) compounds having the structure

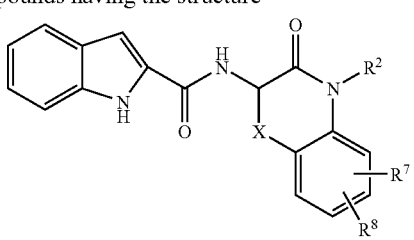

wherein the following occur simultaneously;

X is —$CH_2$— or —$CH_2CH_2$—;

$R^2$ is naphthyl or a 2-methoxyphenyl group containing at least two other substituents chosen from $C_1$-$C_3$ alkyl, $C_1$-$C_3$ alkoxy, halogen or trifluoromethyl;

$R^7$ is hydrogen and $R^8$ is $C_1$-$C_4$ alkyl, $C_1$-$C_3$ alkoxy or halo, or $R^8$ is hydrogen and $R^7$ is $C_1$-$C_4$ alkyl, $C_1$-$C_3$ alkoxy or halo, (d) compounds having the structure

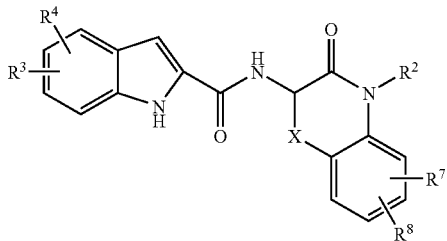

wherein the following occur simultaneously;
X is $CHR^{17}S$, $CHR^{17}SO_2$, $CHR^{17}CO$ or $CH_2CH_2$
$R^2$ is $CH_2CONR^{18}R^{19}$;
$R^3$ and $R^4$ are independently hydrogen, methyl, chloro or methoxy, where at least one of $R^3$ or $R^4$ is hydrogen;
$R^7$ and $R^8$ are each independently hydrogen, halogen, triflouromethyl, $C_1$-$C_3$ alkyl or $C_1$-$C_4$ alkoxy;
$R^{17}$ is hydrogen or methyl;
$R^{18}$ is $C_3$-$C_6$ alkyl or phenyl;
$R^{19}$ is $C_3$-$C_6$ alkyl, benzyl, phenyl or phenyl substituted with cyano, hydroxy, —$O(C_1$-$C_4$ alkyl), —$O(CH_2C_6H_5)$, —$NH(C_1$-$C_4$ alkyl), —$COO(C_1$-$C_4$ alkyl), $N(C_{1-4}$ alkyl$)_2$ or pyrrolidino.

DETAILED DESCRIPTION OF THE INVENTION

The following abbreviations have the indicated meanings:
min=minute(s)
h or hr=hour(s)
L=liter
mL=milliliter
μL=microliter
g=gram(s)
mg=milligram(s)
mol=moles
M=molar
mmol=millimole(s)
HPLC=high performance liquid chromatography
HPLC/MS or LC/MS=high performance liquid chromatography/mass spectrometry
MS or Mass Spec=mass spectrometry
[M+H]=parent plus a proton
[M−H]=parent minus a proton The following definitions apply to the terms as used throughout this specification, unless otherwise limited in specific instances.

The term "hydrogen bonding group(s)" describes functional groups that may form a hydrogen bond by either donating or accepting a hydrogen atom. Examples of suitable "hydrogen bonding group(s)" include, but are not limited to $OR^{9A}$, $OCO_2R^{10}$, $OCONR^{9A}R^{9B}$, $CN$, $NO_2$, $CN_4R^{9A}$ (tetrazole), $COCF_3$, $COR^{9A}$, $CO_2R^{9A}$, $CONR^{9A}R^{9B}$, $CONR^{9A}OR^{9B}$, $C(NR^{9A})NR^{9B}R^{9C}$, $CONR^{9A}SO_2R^{9B}$, $SOR^{10}$, $SO_2R^{10}$, $SO_3H$, $SO_2NR^{9A}R^{9B}$, $SO_2NR^{9A}COR^{9B}$, $SO_2NR^{9A}CONR^{9B}R^{9C}$, $POR^{9A}R^{9B}$, $PO_2R^{9A}R^{9B}$, $PO_3R^{9A}R^{9B}$, $PO_2R^{9A}NR^{9B}R^{9C}$, $NR^{9A}R^{9B}$, $NR^{9A}COR^{9B}$, $NR^{9A}C(NR^{9B})R^{9C}$, $NR^{9A}CO_2R^{9B}$, $NR^{9A}CONR^{9B}R^{9C}$, $NR^{9A}C(NR^{9B})NR^{9C}R^{9D}$, $NR^{9A}SO_2R^{9B}$, $NR^{9A}CONR^{9B}SO_2R^{9C}$, $NR^{9A}SO_2NR^{9B}R^{9C}$, $NR^{9A}POR^{9B}R^{9C}$, $NR^{9A}PO_2R^{9B}R^{9C}$, $NR^{9A}PO_3R^{9B}R^{9C}$, $NR^{9A}PO_2R^{9B}NR^{9C}R^{9D}$, and the like, wherein $R^{9A}$, $R^{9B}$, $R^{9C}$ and $R^{9D}$ for each occurrence are each independently hydrogen, alkyl, arylalkyl, heteroarylalkyl or aryl; and $R^{10}$ is independently alkyl, arylalkyl, heteroarylalkyl, or aryl.

Moreover, $R^{9A-9D}$ and $R^{10}$ may be further substituted by one to three hydrogen bonding groups, for example, $CONR^{9A}R^{9B}$ may represent $CON(Me)CH_2CH_2OH$. Optionally, two of $R^{9A}$, $R^{9B}$, $R^{9C}$ or $R^{9D}$ within the same hydrogen bonding group may be cyclized together to form a ring, for example, $CONR^{9A}R^{9B}$ may represent $CON(CH_2CH_2CH_2CH_2)$. Said ring may further be substituted with one to three additional hydrogen bonding groups, for example N-acylated hydroxyproline or N-acylated 3,4-dihydroxypyrrolidine.

The term "alkyl" as employed herein, alone or as part of another group, includes straight chain, branched chain and saturated cyclic hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, cyclopropyl, cyclohexyl, and the like.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, that include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl.

Unless otherwise indicated, the term "aryl" or "Ar" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one additional fused heterocyclic ring, for example:

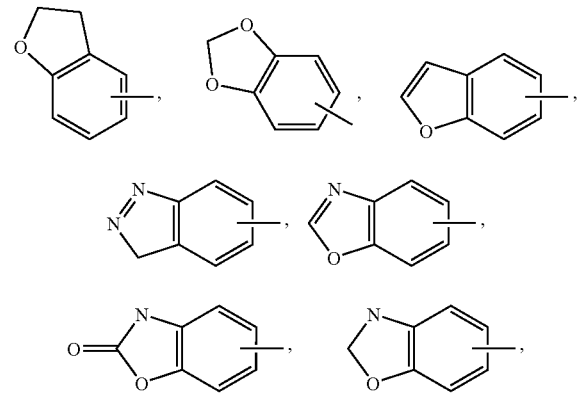

-continued

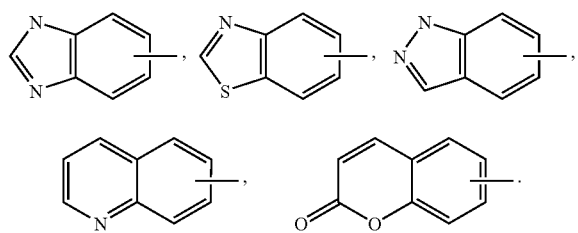

The term "arylalkyl" as used alone or as part of another group refers to an alkyl as defined herein, having an aryl substituent. Representative examples of arylalkyl include, but are not limited to, benzyl, 2-phenylethyl, 3-phenylpropyl, phenethyl, benzhydryl and naphthylmethyl and the like.

The term "halogen" or "halo" as used herein alone or as part of another group refers to chlorine, bromine, fluorine and iodine.

Unless otherwise indicated, the term "alkoxy" or "aryloxy" as employed herein alone or as part of another group refers to an alkyl or aryl group, as defined herein, linked to an oxygen atom.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur, and includes possible N-oxides. Examples of heteroaryl groups include the following:

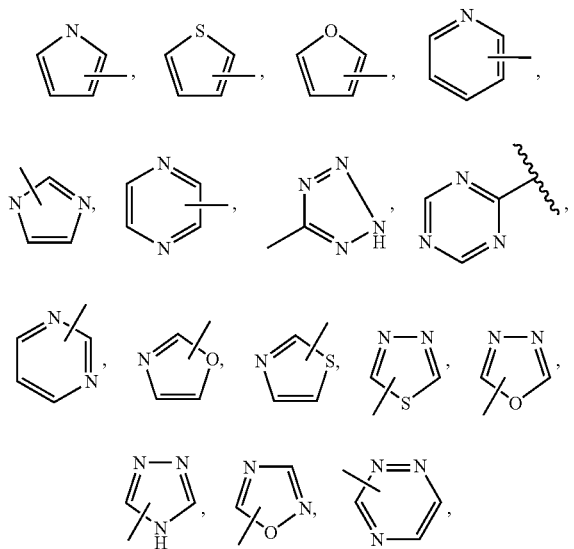

and the like.

As used herein, the term "heteroarylalkyl" means an alkyl group having a heteroaryl substituent.

The term "cyano" as used herein, refers to a —CN group.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tertbutyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate or nitrate.

Preferred salts of the compounds of formula I which contain an acid group include sodium, potassium and magnesium salts and pharmaceutically acceptable organic amines.

Any compound that can be converted in vivo to provide the bioactive agent (i.e., the compound of formula I) is a prodrug within the scope and spirit of the invention.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Various forms of prodrugs are well known in the art and are described in:

a.) *The Practice of Medicinal Chemistry*, Camille G. Wermuth et al., Ch 31, (Academic Press, 1996);

b.) *Design of Prodrugs*, edited by H. Bundgaard, (Elsevier, 1985); and c.) *A Textbook of Drug Design and Development*, P. Krogsgaard-Larson and H. Bundgaard, eds. Ch 5, pgs 113-191 (Harwood Academic Publishers, 1991).

Said references are incorporated herein by reference.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The compounds of formula I of the invention can be prepared as shown below in the following reaction schemes and description thereof, as well by using as relevant published literature procedures that may be used by one skilled in the art. Exemplary reagents and procedures for these reactions appear hereinafter and in the working Examples.

Compounds of formula I may be prepared by coupling carboxylic acids of formula II with amines of formula III using standard methods for amide bond formation, as known to those skilled in the art, for example, by treating equimolar amounts of compounds II and III in N,N-dimethylformamide solution at room temperature with equimolar amounts of 1-hydroxy-7-azabenzotriazole and 1-[3-dimethylamino)propyl]-3-ethylcarbodiimide hydrochloride.

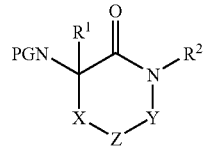

II

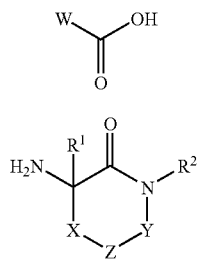

III

Carboxylic acids II may be prepared according to the routes and procedures described in WO 9639384, WO 9926659, and EP 1088824.

Amines III may be prepared by deprotection of the corresponding protected amines IV, in which the amino group is protected (PGN) as a carbamate, amide, phthalimide, N-benzyl derivative, or other standard amine protecting group, such as described in Protective Groups in Organic Synthesis (2$^{nd}$ Edition, T. W. Greene and P. G. M. Wuts, John Wiley & Sons, 1991).

Also included in the definition of protected amine IV are compounds in which the amino group is masked (PGN), i.e., the latent amino group may not fall into the strict definition of a protecting group, such as an azido or nitro group. Protected amines IV where the amino group is masked as a carbamate, amide, phthalimide, N-benzyl derivative, or other standard amine protecting group may be prepared from the amines III as described in Protective Groups in Organic Synthesis. Azido, nitro, and some protected amino groups, such as benzylamino, may be introduced by other means, such as displacement (azido and benzylamino). Carbamates may be prepared not only from the corresponding amine, but also from carboxylic acids by Curtius rearrangement, via the acid chloride, acyl azide and isocyanate (see Comprehensive Organic Synthesis, Editor B. M. Trost, Pergamon Press, 1991).

Synthetic schemes 1 to 28 provide general synthetic routes for the syntheses of amines III and protected amines IV. The reaction steps are subject to the constraints noted. For example, a reaction step noted "for products wherein X is O or S" is subject to the constraint that only products in which X is O or S may be prepared.

SCHEME 1

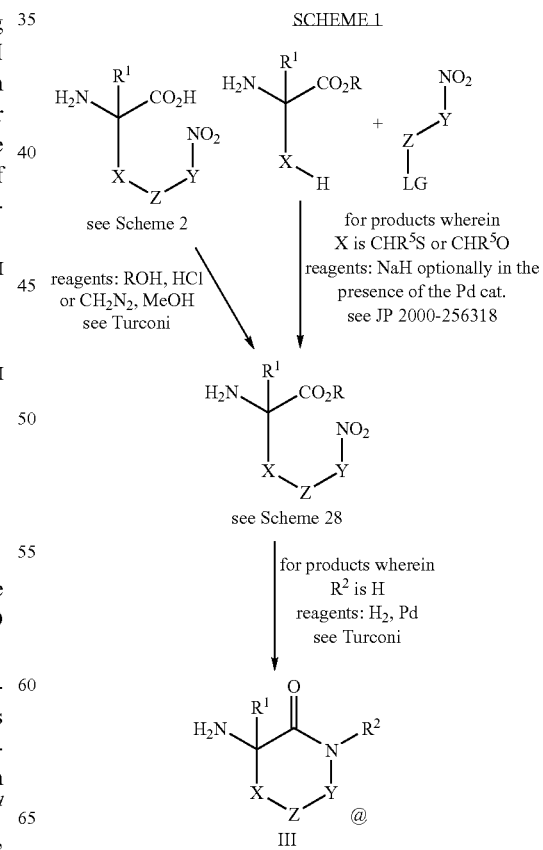

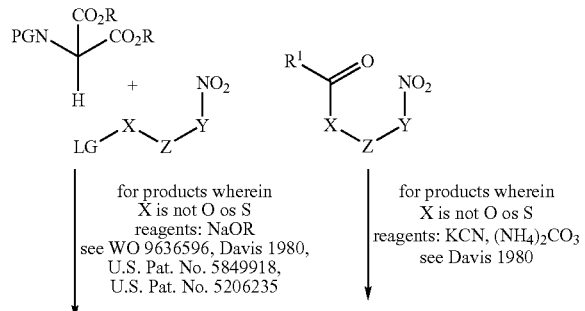
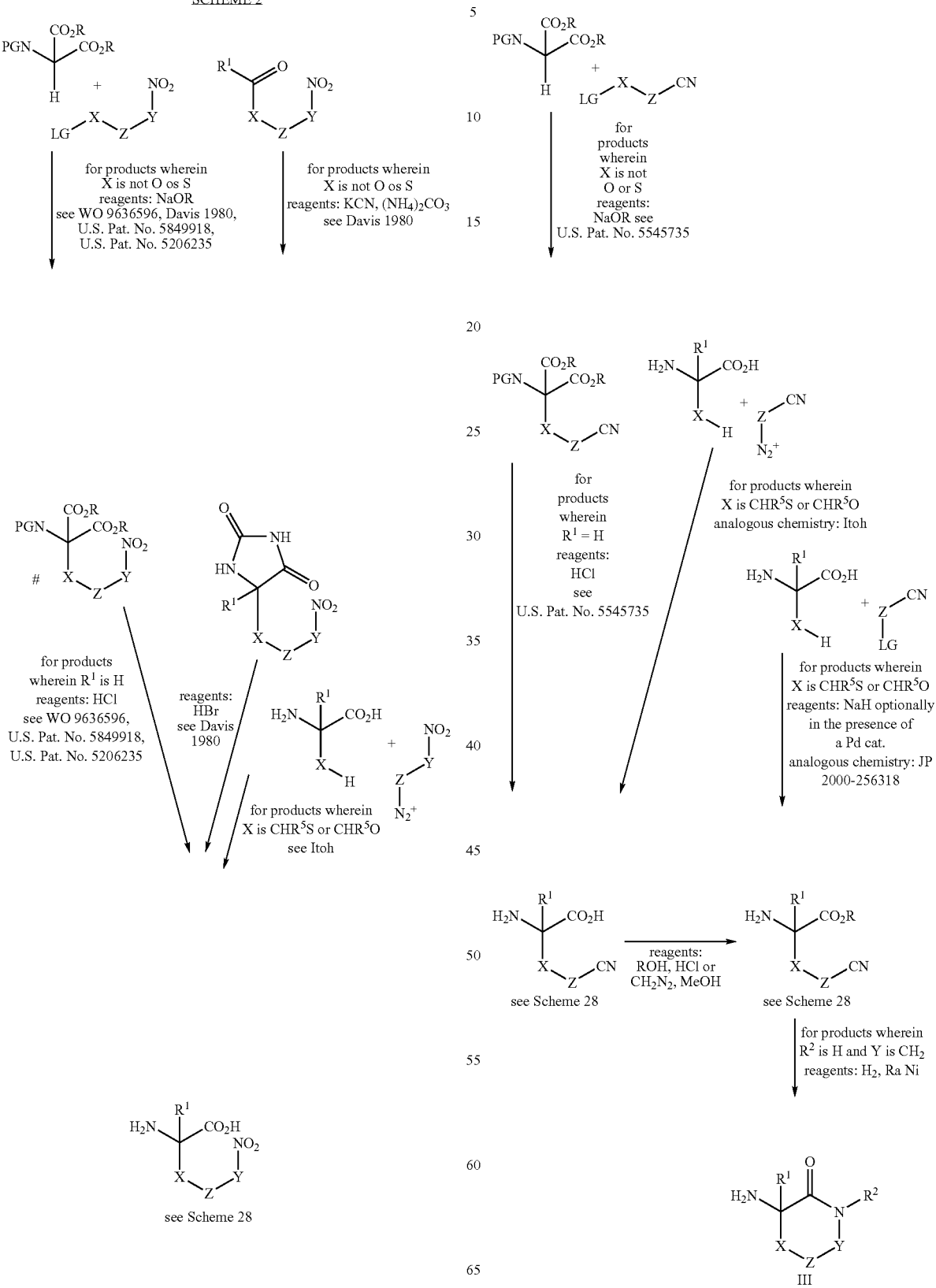

SCHEME 4
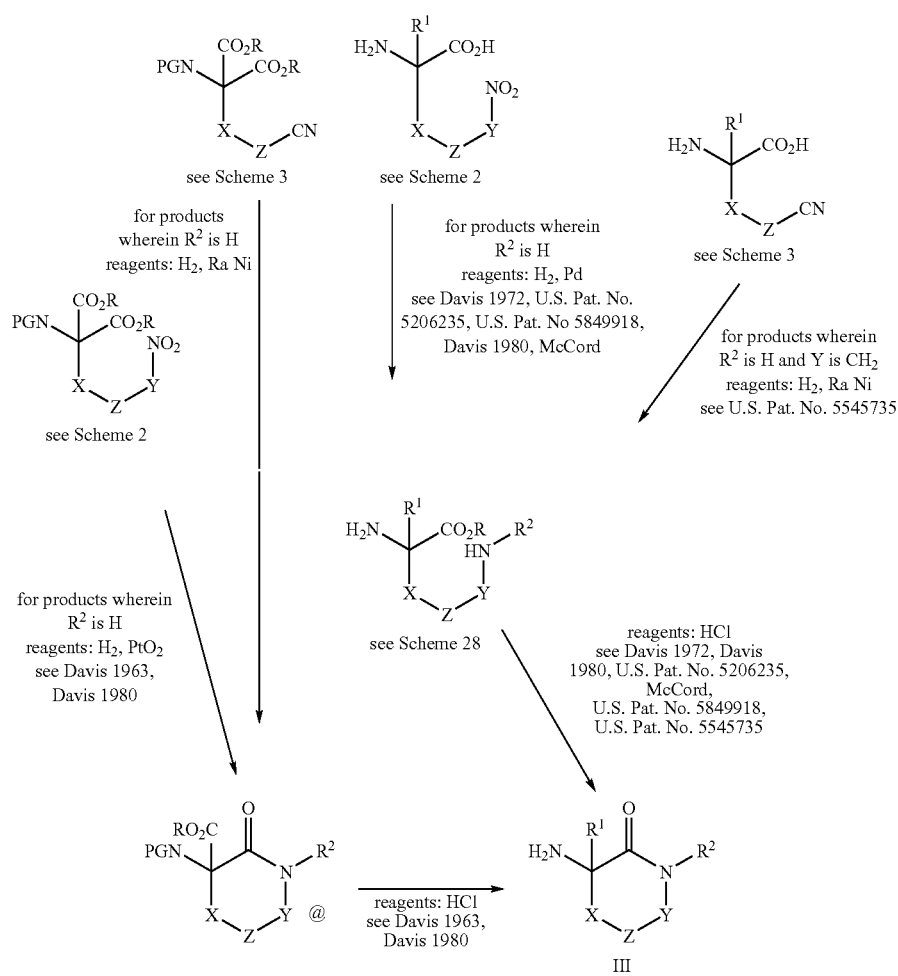
SCHEME 5
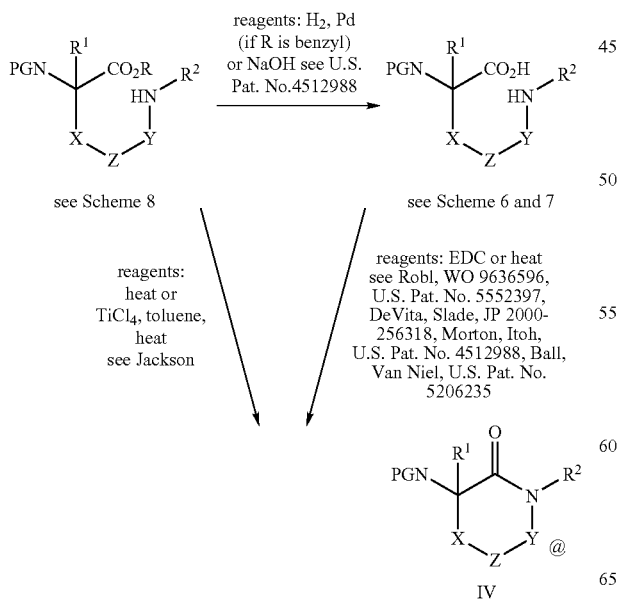

SCHEME 6
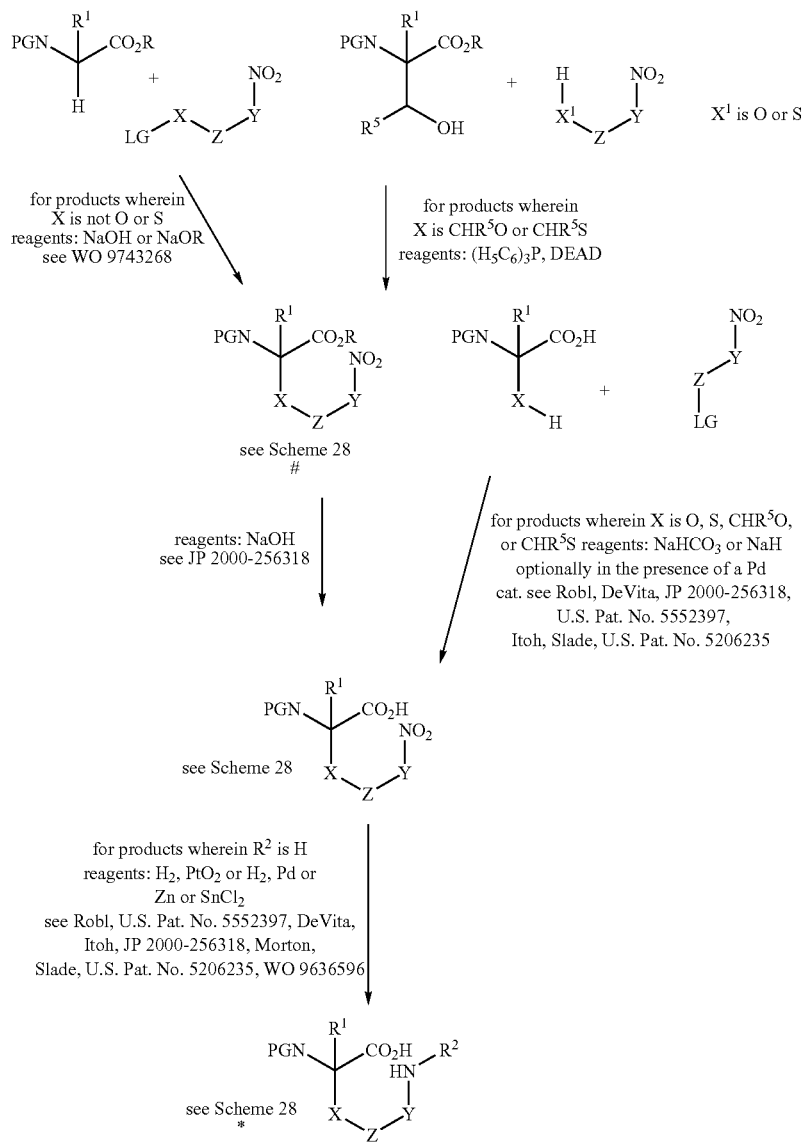
SCHEME 7
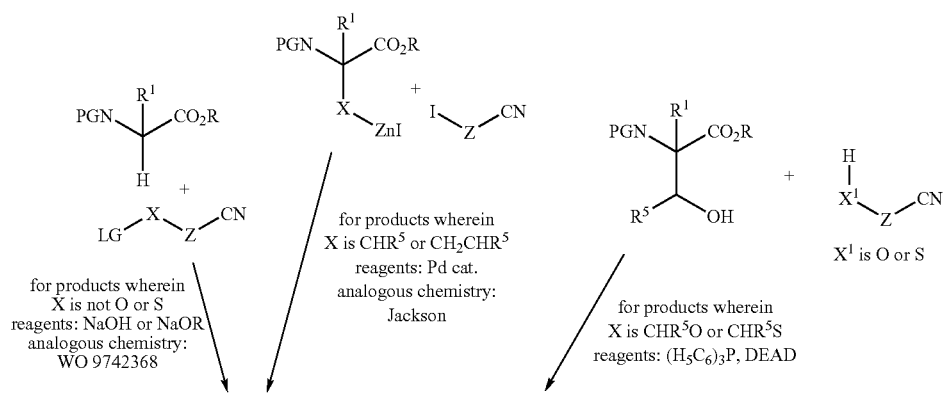

-continued
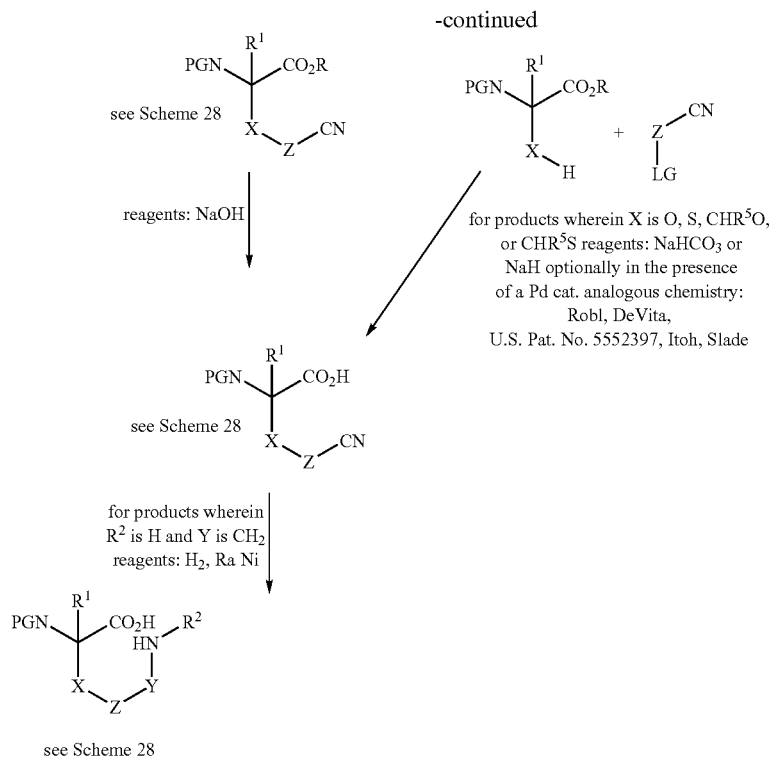
SCHEME 8
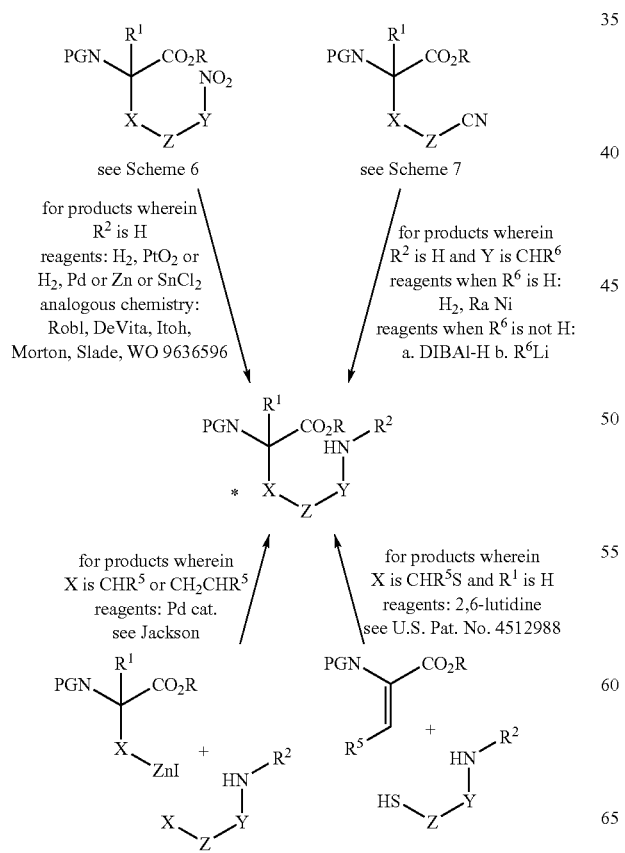

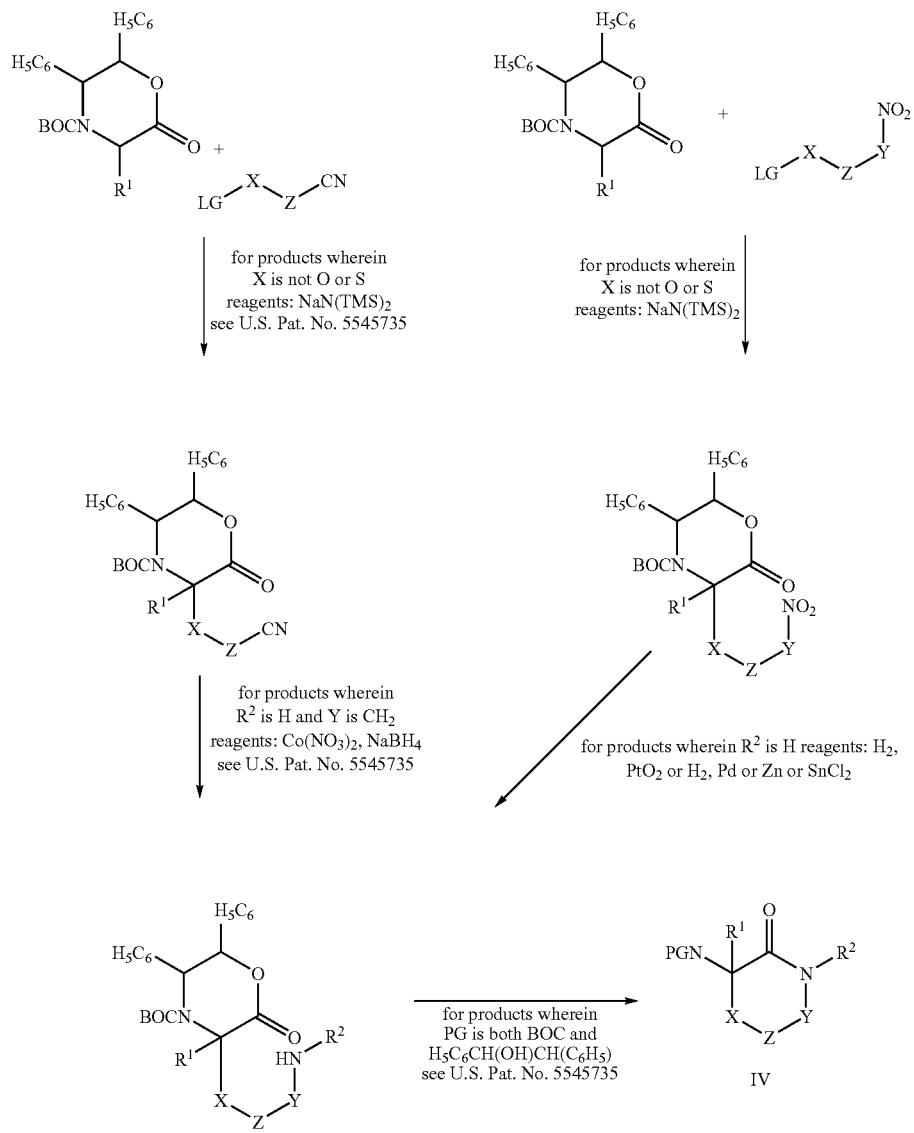
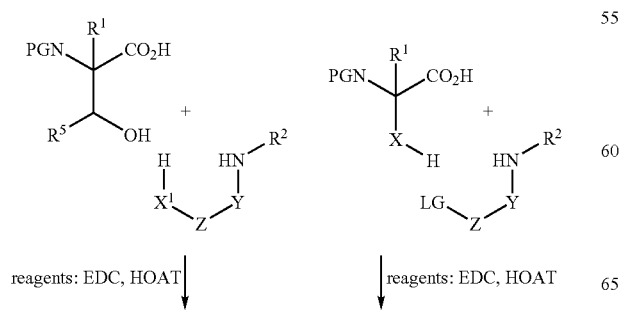

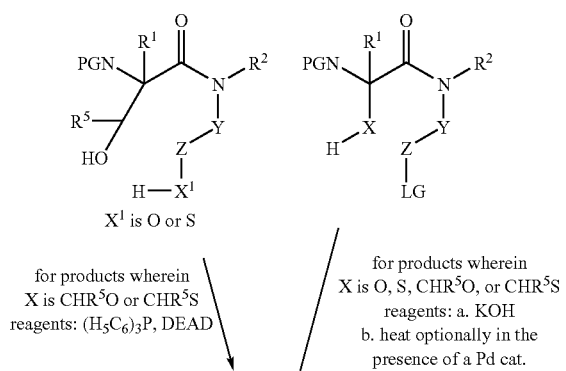

X¹ is O or S for products wherein
X is CHR⁵O or CHR⁵S
reagents: (H₅C₆)₃P, DEAD for products wherein
X is O, S, CHR⁵O, or CHR⁵S
reagents: a. KOH
b. heat optionally in the presence of a Pd cat.

IV

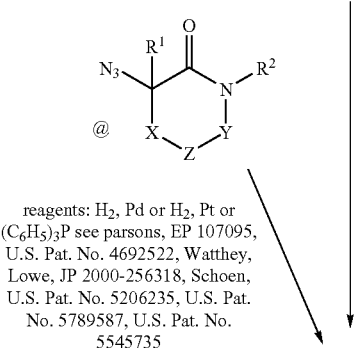

reagents: H₂, Pd or H₂, Pt or (C₆H₅)₃P see parsons, EP 107095, U.S. Pat. No. 4692522, Watthey, Lowe, JP 2000-256318, Schoen, U.S. Pat. No. 5206235, U.S. Pat. No. 5789587, U.S. Pat. No. 5545735

III

SCHEME 11

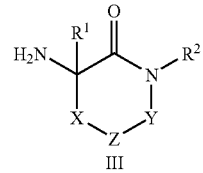

see Schemes 12, 15, 16, and 17

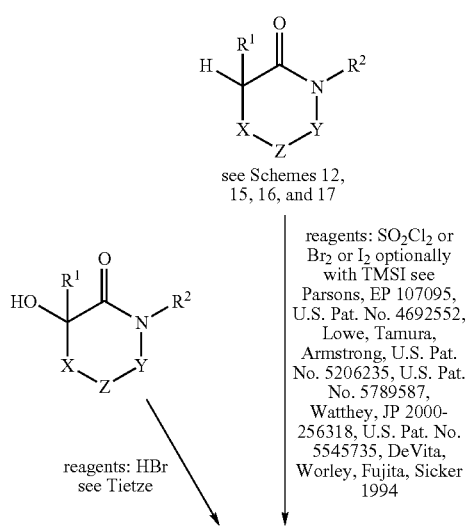

reagents: HBr
see Tietze reagents: SO₂Cl₂ or Br₂ or I₂ optionally with TMSI see Parsons, EP 107095, U.S. Pat. No. 4692552, Lowe, Tamura, Armstrong, U.S. Pat. No. 5206235, U.S. Pat. No. 5789587, Watthey, JP 2000-256318, U.S. Pat. No. 5545735, DeVita, Worley, Fujita, Sicker 1994

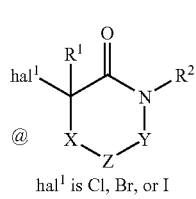

hal¹ is Cl, Br, or I reagents: NaN₃ or TMGN₃
see Parsons, EP 107095, U.S. Pat. No. 4692522, U.S. Pat. No. 5206235, Watthey, Armstrong, Lowe, U.S. Pat. No. 5789587, JP 2000-256318, U.S. Pat. No. 5545735 reagents: NH3
see Tamura, Armstrong, Kluge, U.S. Pat. No. 5545735, DeVita, U.S. Pat. No. 5206235

SCHEME 12

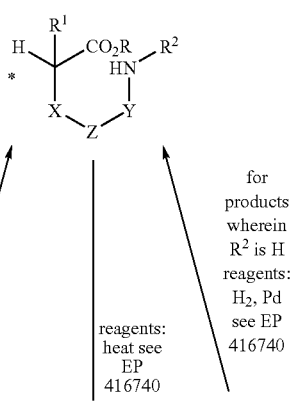

for products wherein R² is H and Y is CHR⁶ reagents when R⁶ is H: H₂, Ra Ni reagents when R⁶ is not H: a. DiBAl-H, b. R⁶Li reagents: heat see EP 416740 for products wherein R² is H reagents: H₂, Pd see EP 416740

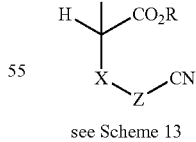

see Scheme 13 for products wherein R² is H and Y is CHR⁶ reagents when R⁶ is H: H₂, Ra Ni reagents when R⁶ is not H:a. DIABAl-H, b. R⁶Li

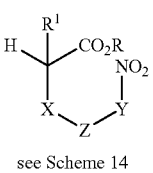

see Scheme 14 for products wherein R² is H reagents: H₂, PtO₂ or H₂, Ra Ni or Fe or Sn see Sicker 1994, U.S. Pat. No. 4755509, EP 416740, U.S. Pat. No. 6017926, EP 160546

-continued

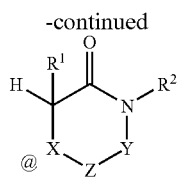

SCHEME 13

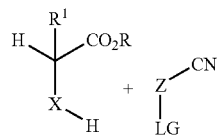

for products wherein X is O, S, CHR⁵O, or
CHR⁵S reagents: NaHCO₃ or NaH optionally in
the presence of a Pd cat. analogous chemistry:
Robl, DeVita, U.S. Pat. No. 5552397, Itoh, Slade

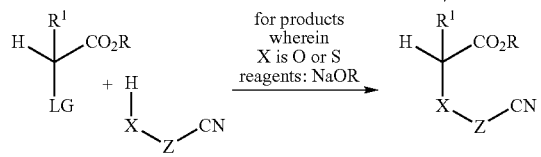

for products
wherein
X is O or S
reagents: NaOR

SCHEME 14

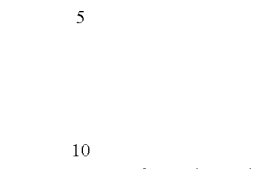 + 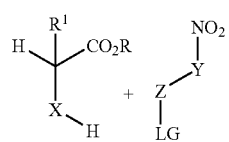

for products wherein X is O, S, CHR⁵O, or CHR⁵S
reagents: NaHCO₃ or NaH optionally in the presence
of a Pd cat. see EP 416740, U.S. Pat. No. 6017926,
U.S. Pat. No. 4755509, EP 160546

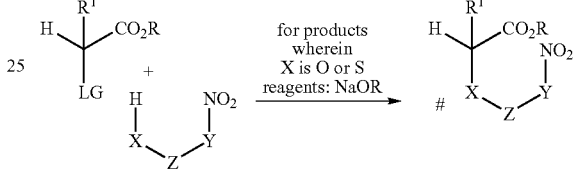

for products
wherein
X is O or S
reagents: NaOR

SCHEME 15

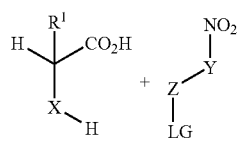

for products
wherein X is
O, S, CHR⁵O,
or CHR⁵S
reagents:
NaOH
optionally in
the presence
of a Pd cat. see
El-Subbah

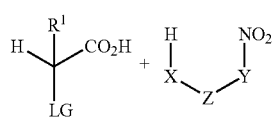

for products wherein
X is O or S reagents:
NaOH see U.S. Pat.
No. 3749715, U.S.
Pat. No. 4755509

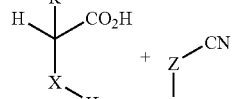

for products wherein X
is O, S, CHR⁵O, or
CHR⁵S reagents: NaOH
optionally in the
presence of a Pd cat.
analogous chemistry: El-
Subbagh

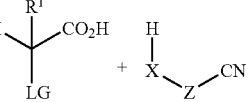

for products
wherein X is
O or S
reagents:
NaOH

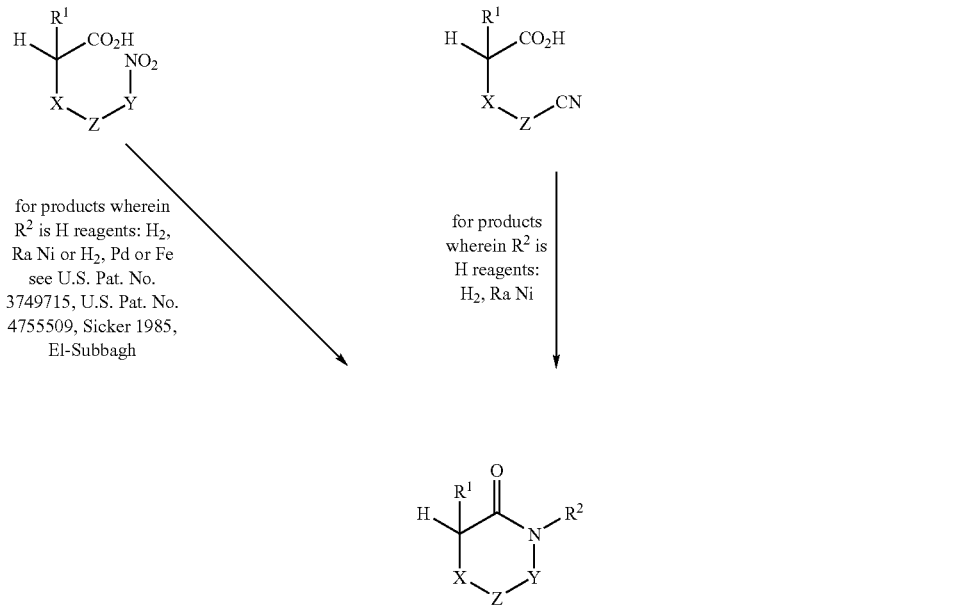
SCHEME 16
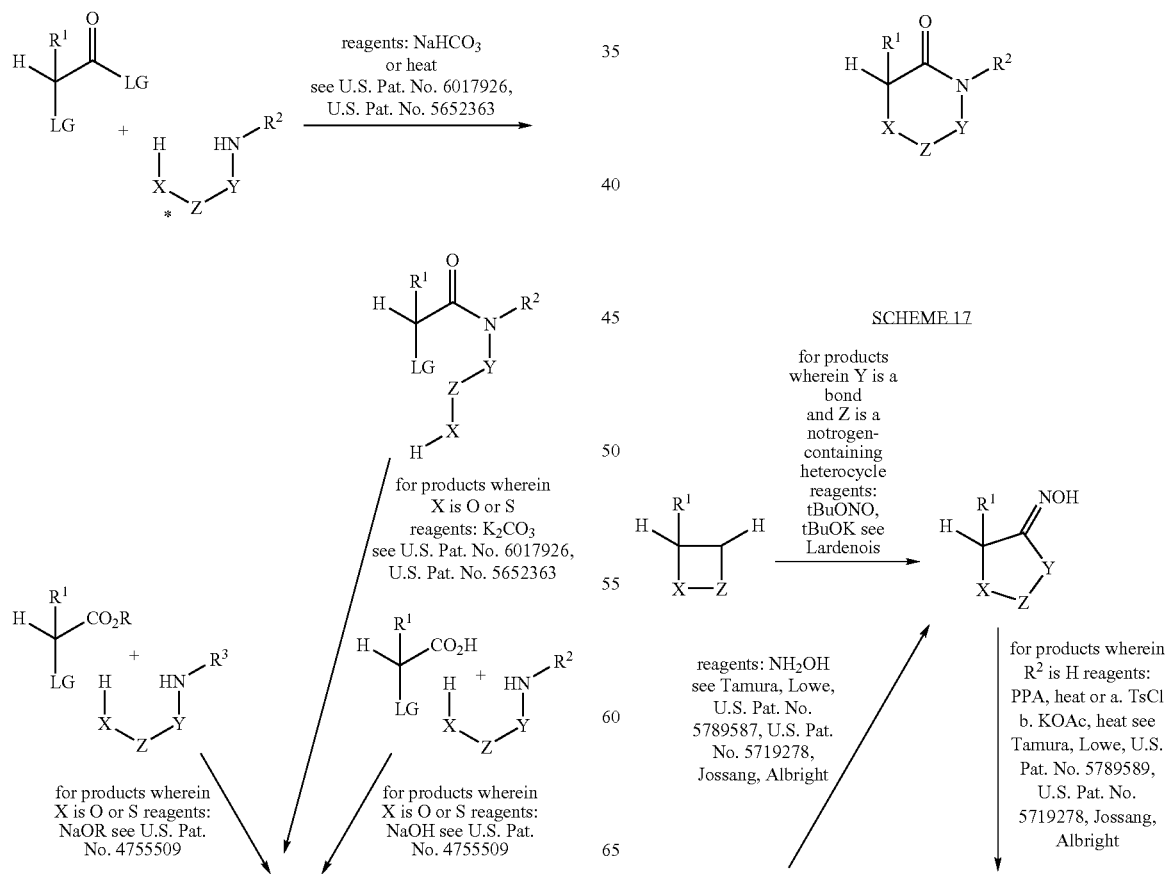
SCHEME 17

-continued

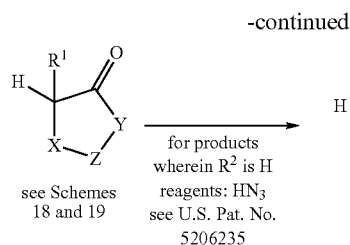

see Schemes 18 and 19 for products wherein R² is H
reagents: HN₃
see U.S. Pat. No. 5206235

SCHEME 18

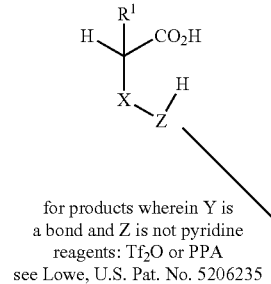

for products wherein Y is a bond and Z is not pyridine
reagents: Tf₂O or PPA
see Lowe, U.S. Pat. No. 5206235 for products wherein Y is a bond
reagents: CrO₃
see Caprathe for products wherein Y is a bond and Z is a pyridine
reagents: a. H₂O₂ b. Ac₂O c. NaOH
see U.S. Pat. No. 5789587, Jossang, Epsztajn

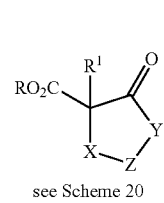

reagents: CrO₃ or C₆H₅POCl₂, DMSO
see U.S. Pat. No. 5789587, Jossang

SCHEME 19

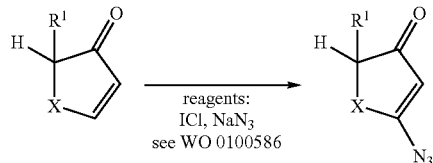

reagents: ICl, NaN₃
see WO 0100586 for products wherein Y is a bond and Z is a pyridine
reagents: a. (C₆H₅)₃P b. acrolein, Pd
see WO 0100586

-continued

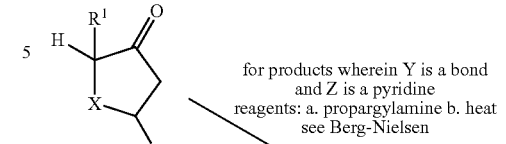

for products wherein Y is a bond and Z is a pyridine
reagents: a. propargylamine b. heat
see Berg-Nielsen reagents: NH₄OAc
see Hunag

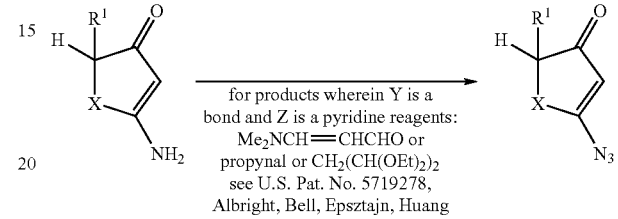

for products wherein Y is a bond and Z is a pyridine reagents:
Me₂NCH=CHCHO or propynal or CH₂(CH(OEt)₂)₂
see U.S. Pat. No. 5719278, Albright, Bell, Epsztajn, Huang

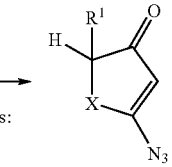

see Scheme 20 reagents: HCl
see WO 0100586

SCHEME 20

for products wherein X is CH₂CHR⁵ and Y is a bond
reagents: LDA
see WO 100586 see Schemes 18 and 19 reagents: base, RO₂CCl

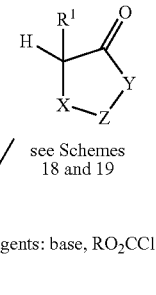

for products wherein Y is a bond and Z is not pyridine
reagents: a. (COCl)₂ b. AlCl₃ reagents: Swern or Dess-Martin oxidants

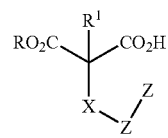

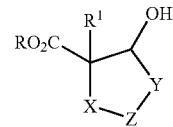

SCHEME 21

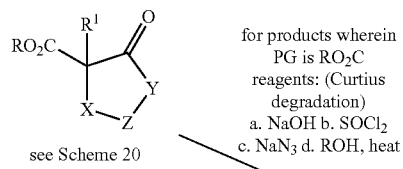

see Scheme 20 for products wherein
PG is RO₂C
reagents: (Curtius
degradation)
a. NaOH b. SOCl₂
c. NaN₃ d. ROH, heat reagents: NH₂OH
analogous chemistry:
Tamura, Lowe,
Jossang, Albright

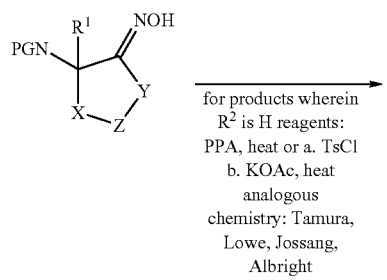

for products wherein
R² is H reagents:
PPA, heat or a. TsCl
b. KOAc, heat
analogous
chemistry: Tamura,
Lowe, Jossang,
Albright

SCHEME 22

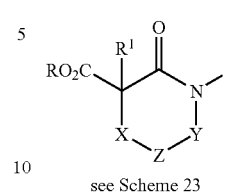

see Scheme 23 reagents: (Curtius
Degradation) a. KOH
b. SOCl₂ c. NaN₃
see Turconi

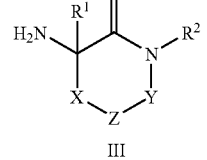

reagents: HCl, heat
see Turconi

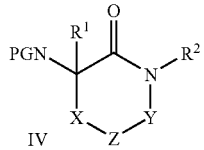

III for products wherein
PG is RO₂C
reagents: ROH, heat

IV

SCHEME 23

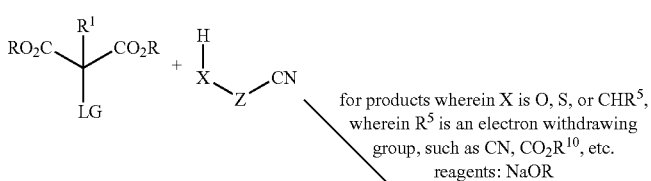

for products wherein X is O, S, or CHR⁵,
wherein R⁵ is an electron withdrawing
group, such as CN, CO₂R¹⁰, etc.
reagents: NaOR

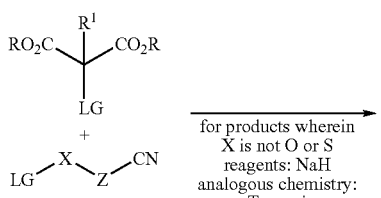

for products wherein
X is not O or S
reagents: NaH
analogous chemistry:
Turconi for products wherein
R² is H and Y is CH₂
reagents: H₂, Ra Ni -continued
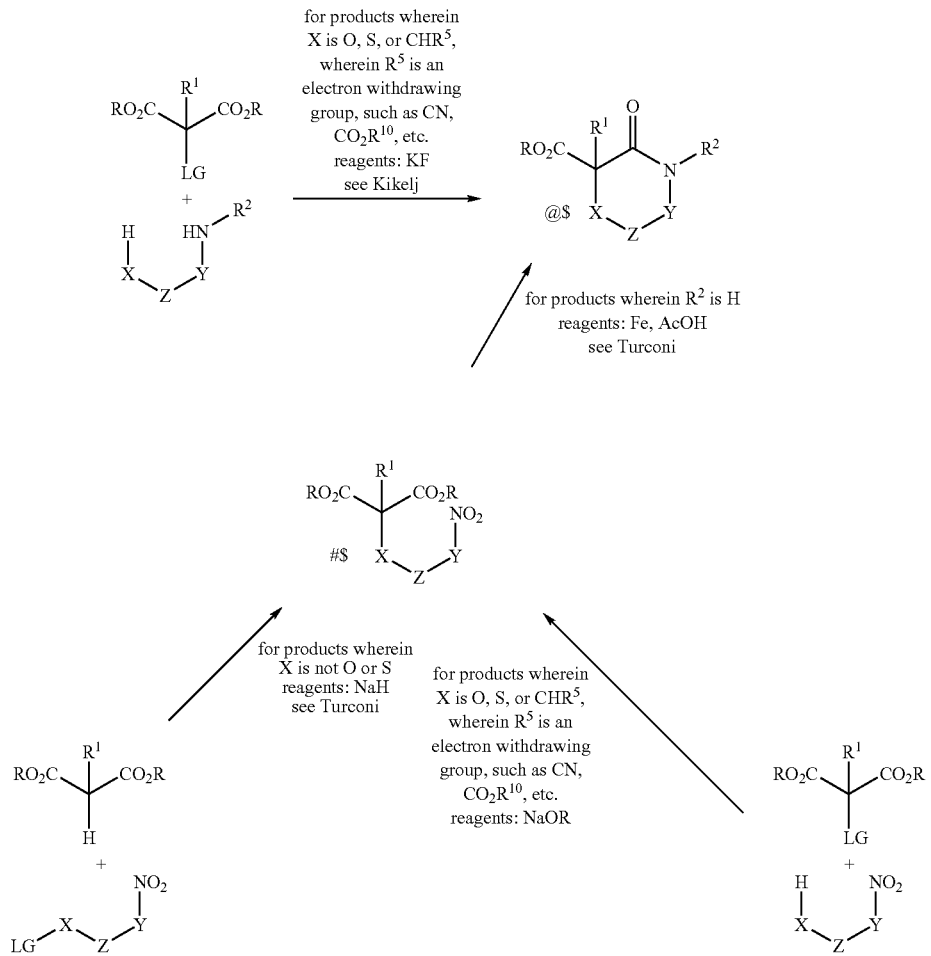
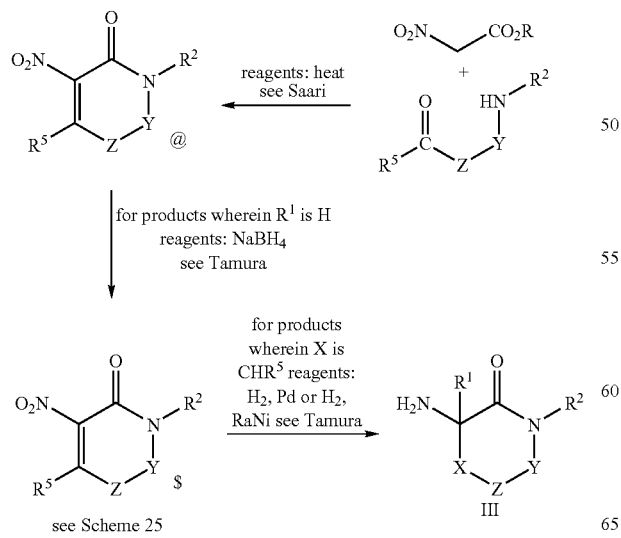
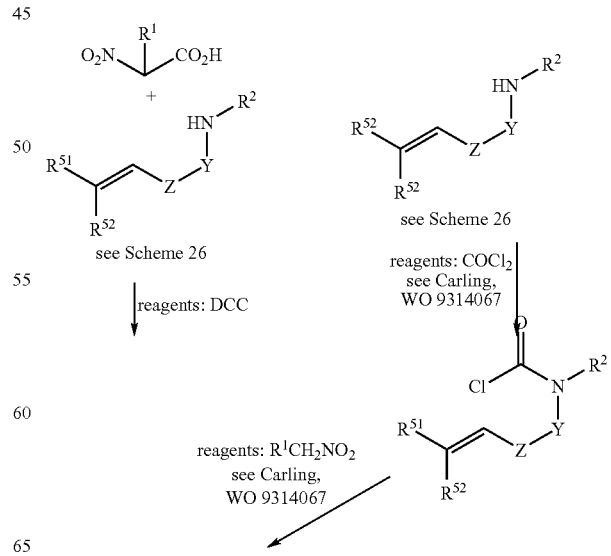

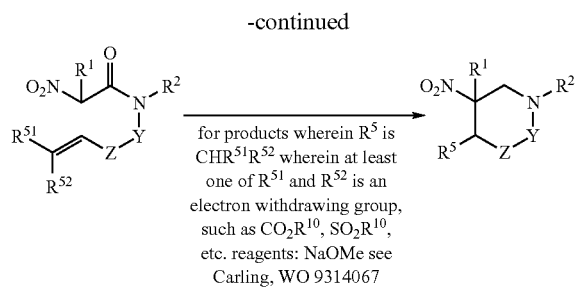
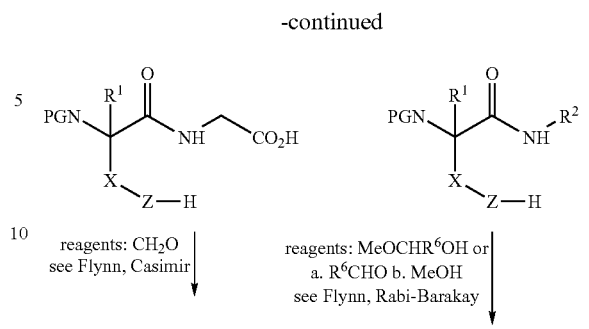
SCHEME 26
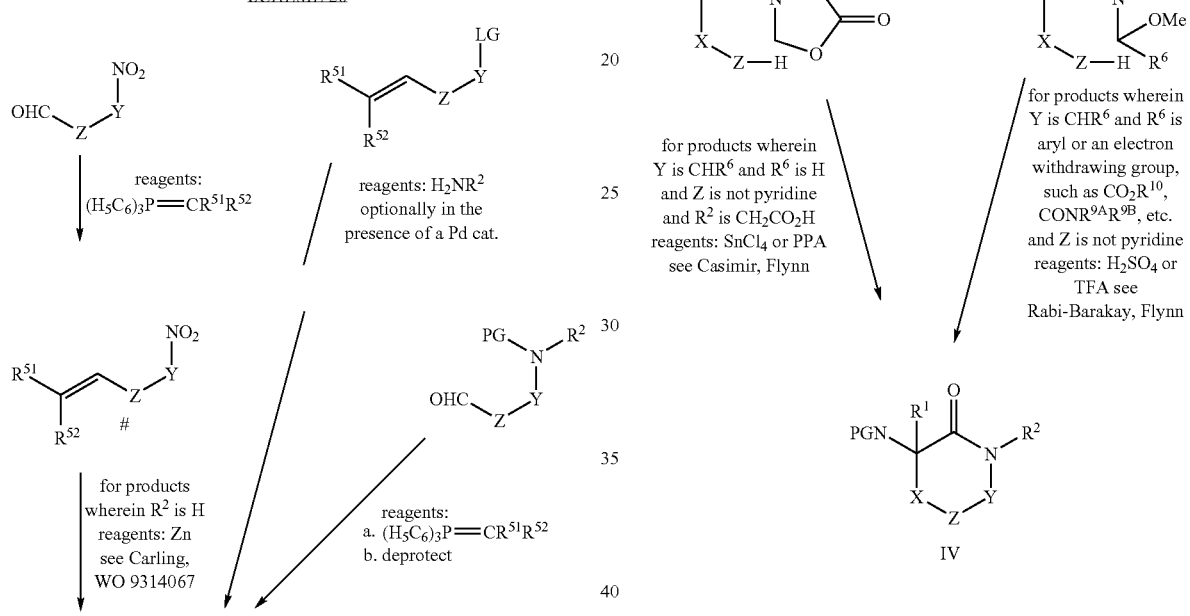
SCHEME 27
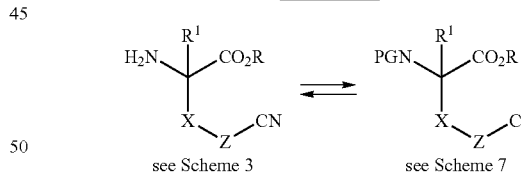
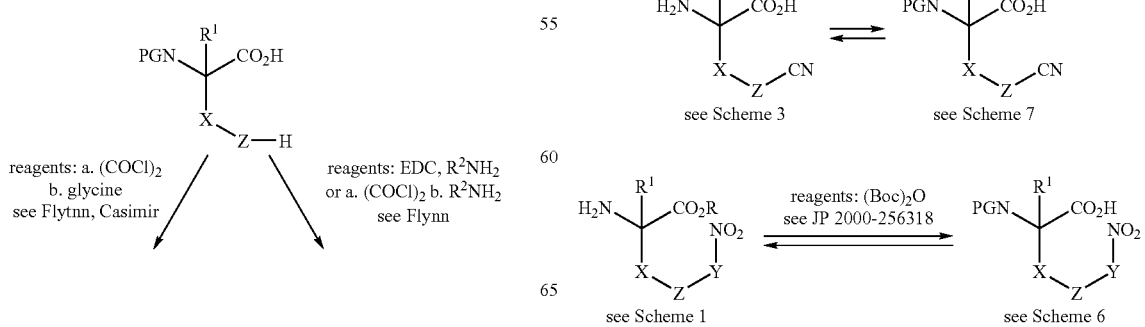
SCHEME 28
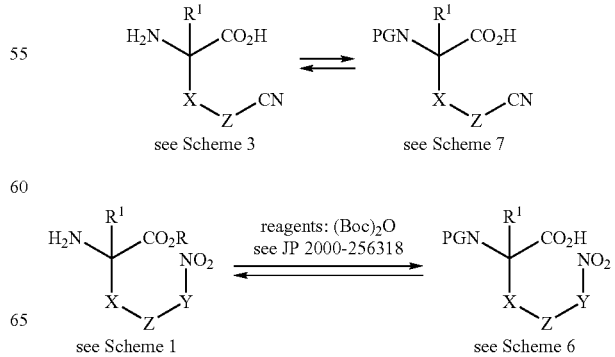

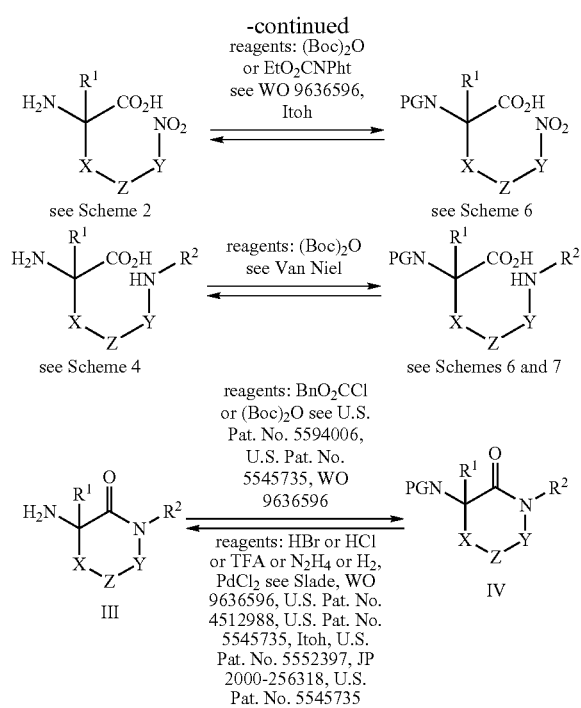

In the synthetic schemes above the reagent lists are abbreviated. References cited provide full details and in some cases alternative reagents. It is understood that the reagents shown in the synthetic schemes are example reagents, not meant to be limiting. Those skilled in the art will recognize that there are many acids (hydrochloric acid, polyphosphoric acid, etc.), many bases (sodium hydride, potassium methoxide, etc.), many oxidants (hydrogen peroxide, 3-chloroperoxybenzoic acid, etc.), many hydrogenation catalysts (palladium, platinum oxide, Raney® Nickel, etc.), and so on that may be employed to synthesize the compounds of the invention. In some cases alternative reagents known to those skilled in the art will be superior to those listed in the synthetic schemes. Alternative reagents may be found in Reagents For Organic Synthesis (Fieser and Fieser, John Wiley & Sons) and Compendium of Organic Synthetic Methods (John Wiley & Sons).

In the synthetic schemes LG represents a leaving group, for example fluoride, bromide, methanesulfonate or trifluoromethanesulfonate. The group R as utilized in the above schemes, (lacking a superscripted numeral) represents an alkyl or benzyl group.

In the synthetic schemes the possibility that certain compounds may be transformed from one variant of the structure to another variant of the same structure is denoted by the appearance of one or more of the following symbols next to the structure: $, *, @, #.

These symbols appear only at the first instance of the intermediate structure to which they pertain. The meaning of these symbols is as follows:

Intermediates denoted $ in which $R^1$ is an unsubstituted or substituted alkyl or alkenyl group may be prepared from the corresponding intermediates denoted $ in which $R^1$ is hydrogen by treatment with a base such as sodium hydride and the appropriate unsubstituted or substituted alkylating or alkenylating agent.

Intermediates denoted * in which $R^2$ is $R^{21}R^{22}CH$ ($R^{21}$ and $R^{22}$ are independently defined in the same manner as $R^2$) may be prepared from the corresponding intermediates denoted * in which $R^2$ is hydrogen by reductive amination with a ketone or aldehyde $R^{21}R^{22}CO$ and a reducing agent, such as sodium cyanoborohydride in the presence of an acid, such as acetic acid.

Intermediates denoted * in which $R^2$ is aryl may be prepared from the corresponding intermediates denoted * in which $R^2$ is hydrogen by palladium catalyzed coupling with an aryl halide, as described in Hamann, et al., J. Am. Chem. Soc. 1998, 120, 7369-7370 and references contained therein, and in recent papers authored by John F. Hartwig.

Compounds of formula I and intermediates denoted @ in which $R^2$ is an unsubstituted or substituted alkyl or alkenyl group may be prepared from the corresponding compounds of formula I and intermediates denoted @, respectively, in which $R^2$ is hydrogen by treatment with a base, such as sodium hydride and the appropriate unsubstituted or substituted alkylating or alkenylating agent.

Intermediates denoted # in which Y is $CH_2R^6$ and $R^6$ is an unsubstituted or substituted alkyl or alkenyl group may be prepared from the corresponding intermediates denoted # in which Y is $CH_2$ by treatment with a base such as sodium hydride and the appropriate unsubstituted or substituted alkylating or alkenylating agent.

In several synthetic schemes alpha amino acids or protected alpha amino acids are shown as intermediates or serve as starting materials. Many methods for the preparation of alpha amino acids and protected alpha amino acids are described in, or referenced in: Jackson, et al., J. Org. Chem. 1998, 63, 7875-7884; Ferraris, et al., J. Am. Chem. Soc. 2002, 124, 67-77; Fu, et al., J. Org. Chem. 2001, 66, 7118-7124.

Schemes 1-4 outline the preparation of amines III with late formation of the lactam amide bond. Schemes 5-9 outline the preparation of protected amines IV with late formation of the lactam amide bond. Scheme 10 outlines the preparation of protected amines IV with late formation of the X-Z bond. Schemes 11-20 outline the preparation of amines III with late introduction of the amino group via halogenation of the desamino intermediate. Scheme 21 outlines the preparation of protected amines IV with late expansion of a cyclic ketone to the lactam ring. Schemes 22-23 outline the preparation of amines III and protected amines IV with late Curtius degradation to install the amino group. Schemes 24-26 outline the preparation of protected amines IV with late formation of the X—Cα bond. Scheme 27 outlines the preparation of protected amines IV with late formation of the Y-Z bond. Scheme 28 identifies a set of amine and amine-protected intermediates that may be particularly usefully interconverted using standard amine protecting group chemistry as described in Protective Groups in Organic Synthesis.

Compounds of formula I and protected amines IV wherein $R^7$ or $R^8$ is other than hydrogen, halo, trifluoromethyl, or hydroxy, may be prepared from compounds of formula I and protected amines IV wherein $R^7$ or $R^8$, respectively, is halo or hydroxy, using various palladium catalyzed coupling procedures as described in Aranyos, et al., J. Am. Chem. Soc. 1999, 121, 4369-4378 and Hamann, et al., J. Am. Chem. Soc. 1998, 120, 7369-7370 and references contained therein, and in recent papers authored by Gregory C. Fu, Stephen L. Buchwald, or John F. Hartwig. These procedures are directly applicable when $R^7$ or $R^8$ is halo. When $R^7$ or $R^8$ is hydroxy, prior activation by conversion of the hydroxyl group to a trifluoromethylsulfonyloxy group, as described in the aforementioned references, is required.

Compounds of formula I and protected amines IV in which $R^7$ or $R^8$ is substituted or unsubstituted alkoxy or aryloxy may be prepared by elaboration of the analogous compounds of formula I and protected amines IV wherein $R^7$ or $R^8$, respectively, is hydroxy. For instance, a compound where $R^7$ or $R^8$ is carbomethoxymethoxy may be prepared from the compound in which $R^7$ or $R^8$ is hydroxy by alkylation with methyl bromoacetate. A compound where $R^7$ or $R^8$ is carboxymethoxy may be prepared by hydrolysis of the compound where $R^7$ or $R^8$ is carbomethoxymethoxy or carbo-t-butyloxymethoxy. A compound where $R^7$ or $R^8$ is 2-hydroxyethoxy may be prepared by reduction of the compound where $R^7$ or $R^8$ is carbomethoxymethoxy or carboxymethoxy. A compound where $R^7$ or $R^8$ is 2,3-dihydroxypropyloxy may be prepared from the compound where $R^7$ or $R^8$ is hydroxy by alkylation with glycidyl 3-nitrobenzenesulfonate, followed by epoxide hydrolysis. A compound where $R^7$ or $R^8$ is aryloxy may be prepared from the compound in which $R^7$ or $R^8$ is hydroxy and an aryl halide by various palladium catalyzed coupling procedures as described in Aranyos, et al., J. Am. Chem. Soc. 1999, 121, 4369-4378 and references contained therein, and in recent papers authored by Stephen L. Buchwald.

Compounds of formula I and protected amines IV in which Z is a pyridine N-oxide may be prepared from the corresponding compounds of formula I and protected amines IV in which Z is a pyridine by oxidation with an oxidizing agent, for example 3-chloroperoxybenzoic acid, in a solvent such as dichloromethane.

Compounds of formula I and protected amines IV in which X is $SO_2$ or $CHR^5SO_2$ may be prepared from the corresponding compounds of formula I and protected amines IV in which X is S or $CHR^5S$, respectively, by oxidation with an oxidizing agent, for example m-chlorobenzoic acid, in a solvent such as dichloromethane.

In general, the interchange of functional groups within $R^1$, $R^2$, $R^5$, $R^6$, $R^7$ and $R^8$, including the formation of various hydrogen bonding groups, may be accomplished according to the methods and procedures described in Compendium of Organic Synthetic Methods (John Wiley & Sons) and Comprehensive Organic Transformations—A Guide To Functional Group Preparations (R. C. Larock, VCH Publishers, 1989). It is understood that during the course of manipulating any functional group within $R^1$, $R^2$, $R^5$, $R^6$, $R^7$ and $R^8$, standard protecting groups, as described in Protective Groups in Organic Synthesis, may be employed to avoid undesired reaction of any other functional group, or of the lactam at its carbonyl or nitrogen, particularly when $R^2$ is hydrogen, or of the indole ring or other bicyclic heterocycle W, particularly at its nitrogen, or of the amide linking the lactam containing ring to W. Standard protecting groups may be used for this purpose at any stage of the synthesis, for example in manipulating a functional group to convert one compound of formula I to another compound of formula I, or in manipulating a functional group to convert one protected amine IV to another amine IV, or to avoid undesired reaction during the coupling of carboxylic acid II and amine III, or during the sequence of steps leading to the formation of either carboxylic acid II or protected amine IV.

The references provided within the synthetic schemes herein are not intended to constrain the applicability of the reaction steps, but rather to exemplify the reaction and provide further experimental detail. The references are designated by either a patent/publication number or the first author of a scientific journal publication. Full scientific journal publication references are provided below in alphabetical order according to first author:

Albright, et al., J. Het. Chem. 2000, 37, 41-46;
Armstrong, et al., Tetrahedron Lett. 1994, 35, 3239-3242;
Ball, et al., J. Heterocyclic Chem. 1990, 27, 279-286;
Bell, et al., J. Med. Chem. 1998, 41, 2146-2163;
Berg-Nielsen, et al., Acta Chem. Scand. B 1978, 32, 553-556;
DeVita, et al., Bioorg. & Med. Chem. Lett. 1995, 5, 1281-1286;
Caprathe, et al., J. Med. Chem. 1991, 34, 2736-2746;
Carling, et al., J. Med. Chem. 1993, 36, 3397-3408;
Casimir, et al., J. Org. Chem. 2000, 65, 6487-6492;
Davis et al., Arch. Biochem. Biophys. 1963, 102, 48-51;
Davis, et al., J. Med. Chem. 1972, 15, 325-327;
Davis, et al., J. Het. Chem. 1980, 17, 1405-1408;
El-Subbagh, et al., Arch. Pharm. Med. Chem. 1999, 332, 19-24;
Epsztajn, et al, J. Chem. Soc. Perkin Trans. I 1985, 213-219;
Flynn, et al., Biorg. & Med. Chem. Lett. 1991, 1, 309-312;
Fujita, et al., Synth. 1988, 599-604;
Huang, et al., Synth. Commun. 1998, 28, 1197-1200;
Itoh, et al., Chem. Pharm. Bull. 1986, 34, 1128-1147;
Jackson, et al., J. Org. Chem. 1998, 63, 7875-7884;
Jössang-Yanagida, et al., J. Het. Chem. 1978, 15, 249-251;
Kikelj, et al., J. Het. Chem. 1993, 30, 597-602;
Kluge, et al., J. Heterocyclic Chem. 1996, 33, 1623-1626;
Lardenois, et al., Synth. Commun. 1996, 26, 2305-2308;
Lowe, et al., J. Med. Chem. 1994, 37, 3789-3811;
McCord, et al., J. Het. Chem. 1981, 18, 1035-1039;
Morton, et al., Tetrahedron Letters 2000, 41, 3029-3033;
Murakami, et al., J. Med. Chem. 1999, 42, 2621-2632;
Parsons, et al., Biochem. Biophys. Res. Comm. 1983, 117, 108-113;
Rabi-Barakay, et al., Tetrahedron 1994, 50, 10771-10782;
Robl, et al., Bioorg. & Med. Chem. Lett. 1994, 4, 1789-1794;
Saari, et al., J. Med. Chem. 1992, 35, 3792-3802;
Schoen, et al., J. Med. Chem. 1994, 37, 897-906;
Sicker et al., Synth. 1985, 331-333;
Sicker, et al., J. Het. Chem. 1994, 31, 809-812;
Slade, et al., J. Med. Chem. 1985, 28, 1517-1521;
Tamura, et al., Bioorg. & Med. Chem. Lett. 1999, 9, 2573-2578;
Tietze, et al., Synth. 1991, 1118-1120;
Turconi, et al., Bioorg. & Med. Chem. 1994, 2, 1375-1383;
Van Niel, et al., Bioorg. & Med. Chem. Lett. 1995, 5, 1421-1426;
Watthey, et al., J. Med. Chem. 1985, 28, 1511-1516;
Worley, et al., J. Org. Chem. 1975, 40, 1731-1734.

Since those skilled in the art recognize that the efficiency of a chemical reaction is often related to the degree of structural similarity between the substrates and those in the literature procedure followed, the context of the references in the synthetic schemes is provided below for convenience.

Amines III and protected amines IV where X is $CH_2$, Y is a bond, Z is a benzene ring and $R^1$ is hydrogen may be prepared according to the routes and procedures described in Davis 1972; Tamura; Davis 1963; U.S. Pat. No. 5,849,918; WO 9636596; U.S. Pat. No. 5,206,235.

Intermediates leading to protected amines IV where X is $CH_2$, Y is a bond, Z is a benzene ring and $R^1$ is hydrogen may be prepared according to the routes and procedures described in WO 9743268.

Amines III and protected amines IV where X is $CHR^5$, Y is a bond, Z is a benzene ring, $R^5$ is not hydrogen and $R^1$ is hydrogen may be prepared according to the routes and procedures described in McCord; Davis 1980; Carling; WO 9314067.

Amines III and protected amines IV where X is $CH_2$, Y is a bond, Z is a benzene ring and $R^1$ is not hydrogen may be prepared according to the routes and procedures described in Davis 1980; Turconi.

Amines III and protected amines IV where X is $CH_2CH_2$, Y is a bond and Z is a benzene ring may be prepared according to the routes and procedures described in U.S. Pat. No. 5,849,918; EP 107095; U.S. Pat. No. 4,692,522; Tamura; Jackson; Armstrong; Schoen; Robl; Watthey; Parsons; U.S. Pat. No. 5,206,235.

Amines III and protected amines IV where X is $CH_2CHR^5$, Y is a bond, Z is a benzene ring and $R^5$ is not hydrogen may be prepared according to the routes and procedures described in Lowe.

Amines III and protected amines IV where X is $CHR^5O$ or $CHR^5S$, Y is a bond and Z is a benzene ring may be prepared according to the routes and procedures described in Robl; Slade; Itoh; U.S. Pat. No. 5,552,397; U.S. Pat. No. 4,512,988; DeVita; U.S. Pat. No. 5,206,235.

Protected amines IV where X is $CH_2CO$, Y is a bond and Z is a benzene ring may be prepared according to the routes and procedures described in Ball; Van Niel; DeVita.

Amines III where X is O or S, Y is a bond and Z is a benzene ring may be prepared according to the routes and procedures described in Kluge; U.S. Pat. No. 5,206,235; DeVita.

Intermediates leading to amines III where X is O or S, Y is a bond and Z is a benzene ring may be prepared according to the routes and procedures described in Tietze; Fujita; Worley; Sicker 1994; El-Subbagh; U.S. Pat. No. 4,755,509; Kikelj; U.S. Pat. No. 6,017,926.

Amines III and protected amines IV where X is $CHR^5$ or S, Y is $CHR^6$ and Z is a benzene ring may be prepared according to the routes and procedures described in U.S. Pat. No. 5,545,735; Rabi-Barakay; Flynn; Casimir.

Intermediates leading to amines III and protected amines IV where X is $CHR^5$, Y is a bond and Z is a pyridine ring may be prepared according to the routes and procedures described in Caprathe; Berg-Nielsen; Huang.

Amines III and protected amines IV where X is $CHR^5O$ $CHR^5S$, or $CHR^5SO_2$, Y is a bond and Z is a pyridine ring may be prepared according to the routes and procedures described in Morton; JP 2000-256318.

Amines III and protected amines IV where X is $CH_2CHR^5$, Y is a bond and Z is a pyridine ring may be prepared according to the routes and procedures described in U.S. Pat. No. 5,789,587; JP 2000-256318.

Intermediates leading to amines III and protected amines IV where X is $CH_2CHR^5$, Y is a bond and Z is a pyridine ring may be prepared according to the routes and procedures described in Lardenois; Epsztajn; Huang; U.S. Pat. No. 5,719,278; Jössang-Yanagida; Berg-Nielsen; Albright; Caprathe; WO 0100586; Bell.

Intermediates leading to amines III where X is O or S, Y is a bond and Z is a pyridine ring may be prepared according to the routes and procedures described in U.S. Pat. No. 3,749,715; El-Subbagh; U.S. Pat. No. 4,755,509; U.S. Pat. No. 5,652,363; U.S. Pat. No. 6,017,926; EP 416740; Sicker 1985; Kikelj; EP 160546.

Amines III and protected amines IV where X is $CH_2CHR^5$, Y is a bond and Z is a thiophene ring may be prepared according to the routes and procedures described in U.S. Pat. No. 5,789,587.

References to examples of the manipulation of $R^2$ in synthetic intermediates denoted @ include the following:

III where X is $CH_2$, Y is a bond and Z is a benzene ring: Parsons; EP 107095; U.S. Pat. No. 4,692,522; U.S. Pat. No. 5,849,918.

IV where X is $CH_2$, Y is a bond and Z is a benzene ring: U.S. Pat. No. 5,594,006.

IV where X is $CH_2CH_2$, Y is a bond and Z is a benzene ring: Parsons; EP 107095; U.S. Pat. No. 4,692,522; Robl; Murakami.

IV where X is $CH_2O$, Y is a bond and Z is a benzene ring: Robl; Murakami; Itoh.

IV where X is $CH_2S$, Y is a bond and Z is a benzene ring: Slade; Robl; Itoh.

IV where X is $CH_2CO$, Y is a bond and Z is a benzene ring: Ball; Van Niel.

IV where X is $CH_2$, Y is $CH_2$ and Z is a benzene ring: U.S. Pat. No. 5,545,735.

IV where X is $CHR^5O$, Y is a bond and Z is a pyridine ring: JP 2000-256318.

IV where X is $CHR^5S$, Y is a bond and Z is a pyridine ring: Morton; JP 2000-256318.

IV where X is S, Y is a bond and Z is a pyridine ring: U.S. Pat. No. 4,755,509.

Unsaturated nitro compound in Scheme 24: Tamura.

Alpha halo lactam in Scheme 11: Lowe.

Alpha azido lactam in Scheme 11: JP 2000-256318.

Curtius precursor in Scheme 23: Kikelj.

The references above are incorporated herein by reference.

UTILITY & COMBINATIONS

A. Utilities

The compounds of the present invention possess activity as inhibitors of the enzyme glycogen phosphorylase and therefore may be used in the treatment of diseases associated with glycogen phosphorylase activity. Via the inhibition of glycogen phosphorylase, the compounds of the present invention may preferably be employed to inhibit glycogenolysis, thereby interrupting or modulating hepatic glucose production.

Accordingly, the compounds of the present invention can be administered to mammals, preferably humans, for the treatment of a variety of conditions and disorders, including, but not limited to, treating or delaying the progression or onset of diabetes (including Type I and Type II, impaired glucose tolerance, insulin resistance and diabetic complications, such as nephropathy, retinopathy and neuropathy), hyperglycemia, hyperinsulinemia, hypercholesterolemia, elevated blood levels of free fatty acids or glycerol, hyperlipidemia, dislipidemia, hypertriglyceridemia, obesity, delayed wound healing, tissue ischemia, myocardial ischemia, atherosclerosis, hypertension, cancer and infection. Further, the compounds of the present invention can be used to treat or prevent infection in a mammal, e.g., bacterial, fungal, parasitic or viral infection.

In addition, the conditions, diseases, and maladies collectively referred to as "Syndrome X" or Metabolic Syndrome as detailed in Ford, et al., *J. Am. Med. Assoc.* 2002, 287, 356-359 and Arbeeny, et al., *Curr. Med. Chem.—Imm., Endoc. & Metab. Agents* 2001, 1, 1-24, may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may employed in combination with other glycogen phosphorylase inhibitors or one or more other suitable therapeutic agents useful in the treatment of the aforementioned disorders including: antidiabetic agents; anti-atherosclerotic agents; anti-ischemic agents; anti-infective agents; anti-cancer and cytotoxic agents; anti-hyperglycemic agents; lipid lowering agents; anti-hypertensive agents; anti-obesity agents and appetite suppressants.

Examples of suitable anti-diabetic agents for use in combination with the compounds of the present invention include insulin and insulin analogs: LysPro insulin, inhaled formulations comprising insulin; glucagon-like peptides; sulfonylureas and analogs: chlorpropamide, glibenclamide, tolbutamide, tolazamide, acetohexamide, glypizide, glyburide, glimepiride, repaglinide, meglitinide; biguanides: metformin, phenformin, buformin; alpha2-antagonists and imidazolines: midaglizole, isaglidole, deriglidole, idazoxan, efaroxan, fluparoxan; other insulin secretagogues: linogliride, insulinotropin, exendin-4, BTS-67582, A-4166; thiazolidinediones: ciglitazone, pioglitazone, troglitazone, rosiglitazone; PPAR-gamma agonists; PPAR-alpha agonists; PPAR alpha/gamma dual agonists; SGLT2 inhibitors; dipeptidyl peptidase-IV (DPP4) inhibitors; aldose reductase inhibitors; RXR agonists: JTT-501, MCC-555, MX-6054, DRF2593, GI-262570, KRP-297, LG100268; fatty acid oxidation inhibitors: clomoxir, etomoxir, α-glucosidase inhibitors: precose, acarbose, miglitol, emiglitate, voglibose, MDL-25,637, camiglibose, MDL-73,945; beta-agonists: BRL 35135, BRL 37344, Ro 16-8714, ICI D7114, CL 316, 243, TAK-667, AZ40140; phosphodiesterase inhibitors, both CAMP and cGMP type: sildenafil, L686398: L-386,398; amylin antagonists: pramlintide, AC-137; lipoxygenase inhibitors: masoprocal; somatostatin analogs: BM-23014, seglitide, octreotide; glucagon antagonists: BAY 276-9955; insulin signaling agonists, insulin mimetics, PTP1B inhibitors: L-783281, TER17411, TER17529; gluconeogenesis inhibitors: GP3034; somatostatin analogs and antagonists; antilipolytic agents: nicotinic acid, acipimox, WAG 994; glucose transport stimulating agents: BM-130795; glucose synthase kinase inhibitors: lithium chloride, CT98014, CT98023 and galanin receptor agonists.

Other suitable thiazolidinediones include Mitsubishi's MCC-555 (disclosed in U.S. Pat. No. 5,594,016), Glaxo-Welcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi).

Suitable PPAR alpha/gamma dual agonists include AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma; Effect of PPAR alpha Activation on Abnormal Lipid Metabolism in Liver of Zucker Fatty Rats", Diabetes 47, 1841-1847 (1998), and WO 01/21602, the disclosure of which is incorporated herein by reference, employing dosages as set out therein, which compounds designated as preferred are preferred for use herein.

Suitable alpha2 antagonists also include those disclosed in WO 00/59506, employing dosages as set out herein.

Suitable SGLT2 inhibitors include T-1095, phlorizin, WAY-123783 and those described in WO 01/27128.

Suitable DPP4 inhibitors include those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al, Biochemistry, 38 (36), 11597-11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537-1540, 2-cyanopyrrolidides and 4-cyanopyrrolidides, as disclosed by Ashworth et al, Bioorg. & Med. Chem. Lett., Vol. 6, No. 22, pp 1163-1166 and 2745-2748 (1996) employing dosages as set out in the above references.

Suitable aldose reductase inhibitors include those disclosed in WO 99/26659.

Suitable meglitinides include nateglinide (Novartis) or KAD1229 (PF/Kissei).

Examples of glucagon-like peptide-1 (GLP-1) include GLP-1(1-36) amide, GLP-1(7-36) amide, GLP-1(7-37) (as disclosed in U.S. Pat. No. 5,614,492 to Habener), as well as AC2993 (Amylen) and LY-315902 (Lilly).

Other anti-diabetic agents that can be used in combination with compounds of the invention include ergoset and D-chiroinositol.

Suitable anti-ischemic agents include, but are not limited to, those described in the Physicians' Desk Reference and NHE inhibitors, including those disclosed in WO 99/43663.

Examples of suitable anti-infective agents are antibiotic agents, including, but not limited to, those described in the Physicians' Desk Reference.

Examples of suitable lipid lowering agents for use in combination with the compounds of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, cholesterol ester transfer protein inhibitors (e.g., CP-529414 (Pfizer)) and/or nicotinic acid and derivatives thereof.

MTP inhibitors which may be employed as described above include those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440.

The HMG CoA reductase inhibitors which may be employed in combination with one or more compounds of formula I include mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, visastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322.

Preferred hypolipidemic agents are pravastatin, lovastatin, simvastatin, atorvastatin, fluvastatin, cerivastatin, atavastatin and ZD-4522.

In addition, phosphinic acid compounds useful in inhibiting HMG CoA reductase, such as those disclosed in GB 2205837, are suitable for use in combination with the compounds of the present invention.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869-1871, including isoprenoid (phosphinylmethyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243-249, the farnesyl diphosphate analog A and presqualene pyrophosphate (PSQ-PP) analogs as disclosed by Corey and Volante, J. Am. Chem. Soc., 1976, 98, 1291-1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40-43, 48-51, Summary.

The fibric acid derivatives which may be employed in combination with one or more compounds of formula I include fenofibrate, gemfibrozil, clofibrate, bezafibrate, ciprofibrate, clinofibrate and the like, probucol, and related compounds, as disclosed in U.S. Pat. No. 3,674,836, probucol and gemfibrozil being preferred, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents.

The ACAT inhibitor which may be employed in combination with one or more compounds of formula I include those disclosed in Drugs of the Future 24, 9-15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd).

The hypolipidemic agent may be an upregulator of LD2 receptor activity, such as MD-700 (Taisho Pharmaceutical Co. Ltd) and LY295427 (Eli Lilly).

Examples of suitable cholesterol absorption inhibitor for use in combination with the compounds of the invention include SCH48461 (Schering-Plough), as well as those disclosed in Atherosclerosis 115, 45-63 (1995) and J. Med. Chem. 41, 973 (1998).

Examples of suitable ileal $Na^+$/bile acid cotransporter inhibitors for use in combination with the compounds of the invention include compounds as disclosed in Drugs of the Future, 24, 425-430 (1999).

The lipoxygenase inhibitors which may be employed in combination with one or more compounds of formula I include 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al, "15-Lipoxygenase and its Inhibition: A Novel Therapeutic Target for Vascular Disease", Current Pharmaceutical Design, 1999, 5, 11-20.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetamide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-obesity agents for use in combination with the compounds of the present invention include a beta 3 adrenergic agonist, a lipase inhibitor, a serotonin (and dopamine) reuptake inhibitor, a thyroid receptor beta drug and/or an anorectic agent.

The beta 3 adrenergic agonists which may be optionally employed in combination with compounds of the present invention include AJ9677 (Takeda/Dainippon), L750355 (Merck), or CP331648 (Pfizer) or other known beta 3 agonists, as disclosed in U.S. Pat. Nos. 5,541,204, 5,770,615, 5,491,134, 5,776,983 and 5,488,064, with AJ9677, L750,355 and CP331648 being preferred.

Examples of lipase inhibitors which may be optionally employed in combination with compounds of the present invention include orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

Examples of thyroid receptor beta compounds which may be optionally employed in combination with compounds of the present invention include thyroid receptor ligands, such as those disclosed in WO97/21993 (U. Cal SF), WO99/00353 (KaroBio) and GB98/284425 (KaroBio), with compounds of the KaroBio applications being preferred.

The anorectic agent which may be optionally employed in combination with compounds of the present invention include dexamphetamine, phentermine, phenylpropanolamine or mazindol, with dexamphetamine being preferred.

Other compounds that can be used in combination with the compounds of the present invention include CCK receptor agonists (e.g., SR-27897B); galanin receptor antagonists; MCR-4 antagonists (e.g., HP-228); leptin or mimentics; 11-beta-hydroxysteroid dehydrogenase type-1 inhibitors; urocortin mimetics, CRF antagonists, and CRF binding proteins (e.g., RU-486, urocortin).

Further, the compounds of the present invention may be used in combination with anti-cancer and cytotoxic agents, including but not limited to alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α reductase inhibitors; inhibitors of 17β-hydroxy steroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. Additional anti-cancer agents are disclosed in EP 1 177 791. The compounds of the invention may also be used in conjunction with radiation therapy.

The aforementioned patents and patent applications are incorporated herein by reference.

The above other therapeutic agents, when employed in combination with the compounds of the present invention may be used, for example, in those amounts indicated in the Physician's Desk Reference, as in the patents set out above or as otherwise determined by one of ordinary skill in the art.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents.

In carrying out the method of the invention for treating diabetes and related diseases, a pharmaceutical composition will be employed containing the compounds of formula I, with or without other antidiabetic agent(s) and/or antihyperlipidemic agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders and the like. The compounds can be administered to mammalian patient, including humans, monkeys, dogs, etc. by an oral route, for example, in the form of tablets, capsules, beads, granules or powders. Typical solid formulations will contain from about 1 to about 1000 mg of a compound of formula I. The dose for adults is preferably between 1 and 2,000 mg per day, which can be administered in a single dose or in the form of individual doses from 1-4 times per day.

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

Glycogen phosphorylase inhibitor activity of the compounds of the invention may be determined by use of an assay system as set out below.

Assay for Glycogen Phosphorylase Activity

The utility of the compounds of the invention for use in the treatment of diabetes and the other components of Syndrome X and in ischemia may be demonstrated in assays for glycogen phosphorylase inhibition in vitro (U.S. Pat. No. 6,107, 329), effects on blood sugar and insulin in vivo (U.S. Pat. No. 6,107,329), and effects on ischemic tissue damage in vitro (U.S. Pat. No. 6,107,329), and for effects on weight and food intake in vivo (WO 00/47206).

The following working Examples serve to better illustrate, but not limit, some of the preferred embodiments of the present invention.

General

Reverse phase preparative HPLC separation employed an octadecyl sulfate (C-18) column eluting with a solvent gradient of solvents A and B, starting with 20% or more of solvent B and finishing with 100% of solvent B. Solvent A was 10% methanol in water, and solvent B was 90% methanol in water. In certain cases both solvents A and B contained 0.1% of trifluoroacetic acid, as noted.

Preparation of Resin Bound Activated Ester

To a suspension of triphenylphosphine (3.9 g) and 5-chloroindole-2-carboxylic acid (2.9 g) in tetrahydrofuran (100 mL) at room temperature, was added trichloroacetonitrile (2.2 g). The resulting yellow mixture was shaken for 2 h before diisopropylethylamine (2.0 g) and polymer-supported tetrafluorophenol (5.0 g, J. M. Salvino, et al., J. Combinatorial Chem. 2000, 2, 691-697) were added, followed by additional tetrahydrofuran (100 mL). After shaking for 5 h, the solution was drained from the now light brown mixture, and the resin was washed sequentially with N,N-dimethylformamide (50 mL twice), tetrahydrofuran (50 mL twice), and dichloromethane (50 mL twice). Mixed with the resin was a small amount of a yellow, insoluble solid, which was removed by separation in dichloromethane, in which the insoluble solid sank and the resin floated. Resin bound activated ester (5.9 g) was obtained after drying under vacuum. Loading was determined to be 1.0 mmol/g by measurement of the amount of 5-chloro-N-isopropyl-indolecarboxamide obtained after reaction with a large excess isopropylamine in dichloromethane.

Resin Capture Procedure

A mixture of amine (about 0.04 mmol) and the resin bound activated ester prepared above (about 0.05 mmol, always in excess) in tetrahydrofuran (1-2 mL) was shaken room temperature for 1-2 days. The mixture was filtered and the resin was rinsed with tetrahydrofuran (1 mL). The combined filtrate and rinses were evaporated under vacuum and analyzed by HPLC/MS. Starting amines used were free bases unless otherwise noted. In cases where an amine salt was used, a scavenger base was also present, as noted.

Carbodiimide Mediated Amide Bond Formation Procedure

A mixture of amine (0.04-0.23 mmol), N,N-dimethylformamide (0.8 mL), 5-chloroindole-2-carboxylic acid (1-2 equiv), 1-hydroxy-7-azabenzotriazole (1-2 equiv), and 1-[3-(dimethylamino)propyl]-3-ethylcarbodiimide hydrochloride (1.5-2.0 equiv) was stirred at room temperature. The starting amines were free bases unless otherwise noted. In cases where an amine salt was used, a scavenger base, generally triethylamine (1-2 equiv), was also present. After 16 h, 1.0 M aqueous sodium bicarbonate (0.5 mL) was added to hydrolyze any remaining activated ester. Water (2 mL) was added 1 day later, and the resulting precipitated mixture was centrifuged. The supernatant was removed, and the precipitate was washed by resuspension in water, centrifugation, and supernatant removal. In cases where an additional chemical step was required, such as ester hydrolysis, this crude amide product was used without further purification. In cases where the amide was the final product, further purification was performed as follows. A. The crude amide was stirred at room temperature in N,N-dimethylformamide (0.5 mL), then diluted with methanol (1 mL) and water (0.1 mL). B. The supernatant was injected onto reverse phase preparative HPLC using trifluoroacetic acid containing solvents to isolate pure amide product. Steps A and B were repeated with any remaining precipitate until either the precipitate contained no amide product or the precipitate was pure amide product.

Ester Hydrolysis Procedure

Ester (0.05-0.10 mmol), was dissolved in a mixture of ethanol (1 mL) and 1.0 M aqueous sodium hydroxide (0.5 mL). After stirring at room temperature for 6 h, the mixture was acidified to pH 1-2 by addition of trifluoroacetic acid (0.1 mL), and the product acid was purified by reverse phase preparative HPLC using trifluoroacetic acid containing solvents.

Example 1

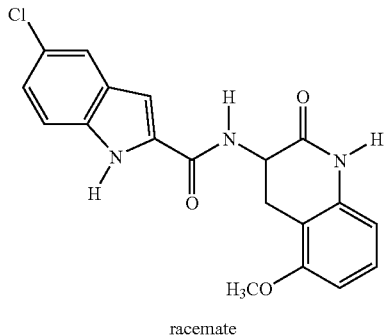

racemate

EXAMPLE 1

3-(5-chloroindole-2-carbonylamino)-5-methoxy-3,4-dihydrocarbostyril

Sodium metal (1.15 g) was dissolved in absolute ethanol (500 mL), and to the resulting solution was added diethyl 2-acetylaminomalonate (9.1 g). After 15 min at room temperature, a solution of 2-methoxy-6-nitrobenzyl bromide (J. Med. Chem. 1977, 20, 190-196) (8.6 g) in tetrahydrofuran (25 mL) was added over 2 min. After 16 h stirring at room temperature the mixture was evaporated. The residue was dissolved in a mixture of ethyl acetate and water. The ethyl acetate layer was separated and washed sequentially with water and brine before drying over anhydrous sodium sulfate. Evaporation was followed by silica gel chromatography eluting initially with dichloromethane, followed by ethyl acetate, to obtain diethyl 2-acetylamino-2-(2-methoxy-6-nitrobenzyl)malonate (10.8 g).

A mixture of diethyl 2-acetylamino-2-(2-methoxy-6-nitrobenzyl)malonate (10.5 g), 10% palladium on carbon (1.0 g), and absolute ethanol (200 mL) was shaken under a hydrogen atmosphere at 60 psi for 45 min. Addition of more 10% palladium on carbon (1.0 g) and further hydrogenation for 20 min was followed by filtration and evaporation of the filtrate. The residue was triturated with 20% methanol in toluene, and the solid was filtered to obtain 3-acetamidoamino-3-carboethoxy-5-methoxy-3,4-dihydrocarbostyril (7.5 g, mp 258-259° C.).

A mixture of 3-acetamidoamino-3-carboethoxy-5-methoxy-3,4-dihydrocarbostyril (5.7 g) and 6 M aqueous hydrochloric acid (75 mL) was refluxed for 6 h. This mixture was evaporated to a solid which was triturated with acetonitrile. Filtration provided 3-amino-5-methoxy-3,4-dihydrocarbostyril hydrochloride (3.8 g, mp 301-302° C. with decomp.) as gray crystals. The free base, 3-amino-5-methoxy-3,4-dihydrocarbostyril, was prepared by ion exchange on an SCX column (United Chemical Technologies, CLEAN-UP Extraction Column, sorbent CUBCX1HL, Synthesis 1997, 553-558) by loading in methanol and eluting with methanol, followed by 2 M methanolic ammonia. The ammonia containing eluant was evaporated to provide 3-amino-5-methoxy-3,4-dihydrocarbostyril.

The title compound was prepared by reaction of the resin bound activated ester with 3-amino-5-methoxy-3,4-dihydrocarbostyril according to Resin Capture Procedure. HPLC/MS [M+H]+, 370; [M–H]−, 368.

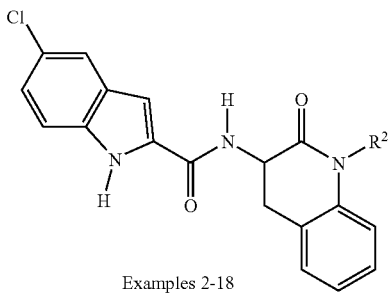

Examples 2-18
see table

| Example | R² | Stereochemistry |
|---|---|---|
| 2 | H | racemate |
| 3, 5 | H | R |
| 4, 6 | H | S |
| 7 | CH₂CO₂CH₃ | R |
| 8 | CH₂CO₂CH₃ | S |
| 9 | CH₂CO₂H | R |
| 10 | CH₂CO₂H | S |
| 11 | CH₂CH₂OH | S |
| 12 | CH₂CONH₂ | R |
| 13 | CH₂CONH₂ | S |
| 14 | OCH₃ | R |
| 15 | OCH₃ | S |
| 16 | CH₂CH=CH₂ | S |
| 17 | CH₂CN | S |
| 18 | CH₂CN | R |

EXAMPLE 2

3-(5-chloroindole-2-carbonylamino)-3,4-dihydrocarbostyril

The title compound was prepared by reaction of the resin bound activated ester with 3-amino-3,4-dihydrocarbostyril (Arch. Biochem. Biophys. 1963, 102, 48-51) according to Resin Capture Procedure. HPLC/MS [M+H]+, 340; [M–H]−, 338.

Homochiral compounds of the title compound from Example 2 were produced in the following Examples 3 and 4.

EXAMPLE 3

(R)-3-(5-chloroindole-2-carbonylamino)-3,4-dihydrocarbostyril

Resolution of 3-amino-3,4-dihydrocarbostyril (Arch. Biochem. Biophys. 1963, 102, 48-51) was performed by separating a racemic mixture of 3-amino-3,4-dihydrocarbostyril into its component (R) and (S) enantiomers by chiral normal phase preparative HPLC (Chiralcel AS column, 25% ethanol in hexane). Analysis was by chiral normal phase analytical HPLC (Chiralcel AS column, 30% ethanol in hexane, S isomer elutes before R isomer).

The title compound was prepared by reaction of the resin bound activated ester with (R)-3-amino-3,4-dihydrocarbostyril according to the Resin Capture Procedure. HPLC/MS [M+H]+, 340; [M–H]−, 338.

EXAMPLE 4

(S)-3-(5-chloroindole-2-carbonylamino)-3,4-dihydrocarbostyril

The title compound was prepared by reaction of the resin bound activated ester with (S)-3-amino-3,4-dihydrocarbostyril from Example 3 according to the Resin Capture Procedure.

HPLC/MS [M+H]+, 340; [M–H]−, 338.

EXAMPLE 5

(R)-3-(5-chloroindole-2-carbonylamino)-3,4-dihydrocarbostyril

To a suspension of racemic 3-amino-3,4-dihydrocarbostyril hydrochloride (300 mg) in acetonitrile (20 mL) at room temperature was added aqueous sodium bicarbonate (378 mg in 5 mL of water) followed by di-t-butyl dicarbonate (425 mg). After stirring for 3 h, the solvent was removed under vacuum, and the residue was dissolved in ethyl acetate. This was washed sequentially with 1 M aqueous sodium hydroxide (60 mL) and brine (60 mL) before drying over anhydrous sodium sulfate and evaporation under vacuum to provide 3-t-butyloxycarbonylamino-3,4-dihydrocarbostyril (413 mg), which was separated into its homochiral component enantiomers (R) and (S) 3-t-butyloxycarbonylamino-3,4-dihydrocarbostyril by chiral normal phase preparative HPLC (Chiralcel AD column, 10% isopropanol in hexane). Analysis was by chiral normal phase analytical HPLC (Chiralcel AD column, 10% isopropanol in hexane, R isomer elutes before S isomer).

(R)-3-t-butyloxycarbonylamino-3,4-dihydrocarbostyril (178 mg) was dissolved in 4 M hydrogen chloride in 1,4-dioxane solution (10 mL) at 0° C. After 1 h the solution was slowly warmed to room temperature over 2 h. The solvent was evaporated under vacuum, and the residue was twice taken up in toluene (10 mL) and evaporated under vacuum to provide (R)-3-amino-3,4-dihydrocarbostyril hydrochloride, a white solid (132 mg).

(R)-3-amino-3,4-dihydrocarbostyril hydrochloride (132 mg) was treated with resin bound activated ester according to the Resin Capture Procedure, but on 14 times the standard scale and with diisopropylethylamine (1 mL) present. Crude product was purified by reverse phase preparative HPLC to provide 193 mg of the title compound. HPLC/MS [M+H]+, 340.

Alternatively, (R)-3-amino-3,4-dihydrocarbostyril hydrochloride (95 mg) was added to a mixture of tetrahydrofuran (10 mL), 5-chloroindole-2-carboxylic acid (103 mg), 1-hydroxy-7-azabenzotriazole (85 mg), and 1-[3-(dimethylamino)propyl]-3-ethylcarbodiimide hydrochloride (120 mg) at room temperature. Diisopropylethylamine (186 mg) was added, and the resulting yellow suspension was stirred for 2 h, during which a solution formed. The solution was diluted with ethyl acetate (50 mL) and washed sequentially with 1.0 M aqueous hydrochloric acid (25 mL), 1.0 M aqueous sodium hydroxide (25 mL), and brine (25 mL), dried over anhydrous sodium sulfate, and evaporated under vacuum. The resulting solid crude product was triturated with diethyl ether (5 mL twice), then 50% methanol in diethyl ether (5 mL twice). Drying under vacuum provided pure title compound (132 mg).

EXAMPLE 6

(S)-3-(5-chloroindole-2-carbonylamino)-3,4-dihydrocarbostyril

The title compound was prepared from (S)-3-t-butyloxycarbonylamino-3,4-dihydrocarbostyril (prepared in Example 5) by the procedures described for the preparation of (R)-3-(5-chloroindole-2-carbonylamino)-3,4-dihydrocarbostyril (Example 5) from (R)-3-t-butyloxycarbonylamino-3,4-dihydrocarbostyril. HPLC/MS [M+H]$^+$, 340; [M+Na]$^+$, 362.

EXAMPLE 7

(R)-1-carbomethoxymethyl-3-(5-chloroindole-2-carbonylamino)-3,4-dihydrocarbostyril (R)-3-t-butyloxycarbonylamino-3,4-dihydrocarbostyril (26 mg), as prepared in Example 5, was dissolved in tetrahydrofuran (5 mL) at room temperature under argon. To the stirring solution was added methyl bromoacetate (31 mg), followed by sodium methoxide (26 mg). The resulting suspension was stirred for 30 min before dilution with ethyl acetate (25 mL) and water (25 mL). The organic phase was separated, washed with water (25 mL), and dried over anhydrous sodium sulfate. After solvent evaporation under vacuum, the crude product was purified by reverse phase preparative HPLC to provide (R)-3-t-butyloxycarbonylamino-1-carbomethoxymethyl-3,4-dihydrocarbostyril (24 mg).

(R)-3-t-butyloxycarbonylamino-1-carbomethoxymethyl-3,4-dihydrocarbostyril (20 mg) was dissolved in 4 M hydrogen chloride in 1,4-dioxane solution (5 mL) at room temperature. After 1 h the solvent was evaporated under vacuum, and the residue was twice taken up in toluene (10 mL) and evaporated under vacuum to provide (R)-3-amino-1-carbomethoxymethyl-3,4-dihydrocarbostyril hydrochloride, a white solid (21 mg).

(R)-3-amino-1-carbomethoxymethyl-3,4-dihydrocarbostyril hydrochloride (21 mg) was treated with resin bound activated ester according to Resin Capture Procedure with diisopropylethylamine (1 mL) present. The resin was rinsed with tetrahydrofuran, N,N-dimethylformamide, and dichloromethane. The combined filtrate and rinses were evaporated under vacuum, and the residue was purified by reverse phase preparative HPLC to provide the title compound (13 mg). HPLC/MS [M+H]$^+$, 412; [M+Na]$^+$, 434.

Alternatively, (R)-3-amino-1-carbomethoxymethyl-3,4-dihydrocarbostyril hydrochloride (19 mg) was added to a mixture of tetrahydrofuran (10 mL), 5-chloroindole-2-carboxylic acid (15 mg), 1-hydroxy-7-azabenzotriazole (12 mg), and 1-[3-(dimethylamino)propyl]-3-ethylcarbodiimide hydrochloride (16 mg) at room temperature. Diisopropylethylamine (19 mg) was added, and the resulting yellow suspension was stirred under argon for 16 h, during which a solution formed. The solution was diluted with ethyl acetate (50 mL) and washed sequentially with 1.0 M aqueous hydrochloric acid (25 mL twice), 1.0 M aqueous sodium hydroxide (20 mL) and brine (20 mL), dried over anhydrous sodium sulfate and evaporated under vacuum. One half of the residue was purified by reverse phase preparative HPLC to provide the title compound (7.6 mg).

EXAMPLE 8

(S)-1-carbomethoxymethyl-3-(5-chloroindole-2-carbonylamino)-3,4-dihydrocarbostyril The title compound was prepared from (S)-3-t-butyloxycarbonylamino-3,4-dihydrocarbostyril (prepared in Example 5) by the procedures described for the preparation of (R)-1-carbomethoxymethyl-3-(5-chloroindole-2-carbonylamino)-3,4-dihydrocarbostyril (Example 7) from (R)-3-t-butyloxycarbonylamino-3,4-dihydrocarbostyril. HPLC/MS [M+H]$^+$, 412.

EXAMPLE 9

(R)-1-carboxymethyl-3-(5-chloroindole-2-carbonylamino)-3,4-dihydrocarbostyril (R)-1-carbomethoxymethyl-3-(5-chloroindole-2-carbonylamino)-3,4-dihydrocarbostyril (Example 7) (13 mg) was dissolved in a 2:2:1 mixture of tetrahydrofuran, methanol, and water (5 mL). Lithium hydroxide monohydrate (3 mg) was added, and the resulting mixture was stirred at room temperature for 2 h. Addition of 1.0 M aqueous hydrochloric acid (10 mL) was followed by extraction with ethyl acetate (20 mL twice). The combined organic layers were washed with brine (10 mL), dried over anhydrous sodium sulfate, and evaporated under vacuum to provide the title compound (12 mg). HPLC/MS [M+H]$^+$, 398.

EXAMPLE 10

(S)-1-carboxymethyl-3-(5-chloroindole-2-carbonylamino)-3,4-dihydrocarbostyril

The title compound was prepared from (S)-1-carbomethoxymethyl-3-(5-chloroindole-2-carbonylamino)-3,4-dihydrocarbostyril (Example 8) by the procedures described for the preparation of (R)-1-carboxymethyl-3-(5-chloroindole-2-carbonylamino)-3,4-dihydrocarbostyril (Example 9) from (R)-1-carbomethoxymethyl-3-(5-chloroindole-2-carbonylamino)-3,4-dihydrocarbostyril. HPLC/MS [M+H]$^+$, 398.

EXAMPLE 11

(S)-1-(2-hydroxyethyl)-3-(5-chloroindole-2-carbonylamino)-3,4-dihydrocarbostyril A mixture of (S)-1-carboxymethyl-3-(5-chloroindole-2-carbonylamino)-3,4-dihydrocarbostyril (Example 10) (6 mg) in 1.0 M borane in tetrahydrofuran solution (2 mL) under argon was stirred at 35° C. for 3 h. After cooling to room temperature, 1.0 M aqueous hydrochloric acid (10 mL) and ethyl acetate (10 mL) were added. This mixture was stirred for 3 h before the layers were separated. The organic phase was washed with water (10 mL three times) and evaporated under vacuum. The residue was chromatographed on reverse phase preparative HPLC to isolate the title compound (1.1 mg) and the over-reduction product (S)-1-(2-hydroxyethyl)-3-(5-chloroindole-2-carbonylamino)-1,2,3,4-tetrahydroquinoline (0.9 mg). Title compound HPLC/MS [M+H]$^+$, 384.

EXAMPLE 12

(R)-1-aminocarbonylmethyl-3-(5-chloroindole-2-carbonylamino)-3,4-dihydrocarbostyril (R)-1-carbomethoxymethyl-3-(5-chloroindole-2-carbonylamino)-3,4-dihydrocarbostyril (Example 7) (5.6 mg) was dissolved in a mixture of tetrahydrofuran (2 mL) and 2 M ammonia in methanol solution (2 mL). After stirring for 16 h at room temperature, the solvent was evaporated under vacuum and the residue was coevaporated with toluene (5 mL twice) under vacuum. Purification by reverse phase preparative HPLC provided the title compound (3.4 mg). HPLC/MS [M+H]$^+$, 397; HPLC/MS [M+H-NH$_3$]$^+$, 380.

EXAMPLE 13

(S)-1-aminocarbonylmethyl-3-(5-chloroindole-2-carbonylamino)-3,4-dihydrocarbostyril (S)-1-carbomethoxymethyl-3-(5-chloroindole-2-carbonylamino)-3,4-dihydrocarbostyril (Example 8) (5 mg) was dissolved in a mixture of tetrahydrofuran (1 mL) and 2 M ammonia in methanol solution (2 mL). After stirring for 16 h at room temperature, the solvent was evaporated and the residue was coevaporated with methanol (3 mL twice) under vacuum. Purification by reverse phase preparative HPLC provided the title compound (2.2 mg). HPLC/MS [M+H]$^+$, 397.

EXAMPLE 14

(R)-3-(5-chloroindole-2-carbonylamino)-1-methyl-3,4-dihydrocarbostyril (R)-3-t-butyloxycarbonylamino-3,4-dihydrocarbostyril (prepared in Example 5, 30 mg) was dissolved in tetrahydrofuran (5 mL) at room temperature under argon. To the stirring solution was added methyl iodide (32 mg), followed by sodium methoxide (7.5 mg). The resulting suspension was stirred for 30 min before dilution with ethyl acetate (25 mL) and water (25 mL). The organic phase was separated, washed with water (25 mL), and dried over anhydrous sodium sulfate. After solvent evaporation under vacuum, the crude product was purified by reverse phase preparative HPLC to provide (R)-3-t-butyloxycarbonylamino-1-methyl-3,4-dihydrocarbostyril (24 mg).

(R)-3-t-butyloxycarbonylamino-1-methyl-3,4-dihydrocarbostyril (20 mg) was dissolved in 4 M hydrogen chloride in 1,4-dioxane solution (5 mL) at room temperature. After 1 h the solvent was evaporated under vacuum, and the residue was twice taken up in toluene (5 mL) and evaporated under vacuum to provide (R)-3-amino-1-methyl-3,4-dihydrocarbostyril hydrochloride (25 mg).

(R)-3-amino-1-methyl-3,4-dihydrocarbostyril hydrochloride (25 mg) was treated with resin bound activated ester according to the Resin Capture Procedure with diisopropylethylamine (1 mL) present. The resin was rinsed with tetrahydrofuran, N,N-dimethylformamide, and dichloromethane. The combined filtrate and rinses were evaporated under vacuum, and the residue was purified by reverse phase preparative HPLC to provide the title compound (13 mg). HPLC/MS [M+H]$^+$, 354.

EXAMPLE 15

(S)-3-(5-chloroindole-2-carbonylamino)-1-methyl-3,4-dihydrocarbostyril

The title compound was prepared from (S)-3-t-butyloxycarbonylamino-3,4-dihydrocarbostyril (prepared in Example 5) by the procedures described for the preparation of (R)-3-(5-chloroindole-2-carbonylamino)-1-methyl-3,4-dihydrocarbostyril (Example 14) from (R)-3-t-butyloxycarbonylamino-3,4-dihydrocarbostyril. HPLC/MS [M+H]$^+$, 354.

EXAMPLE 16

(S)-1-allyl-3-(5-chloroindole-2-carbonylamino)-3,4-dihydrocarbostyril (S)-3-t-butyloxycarbonylamino-3,4-dihydrocarbostyril (prepared in Example 5, 30 mg) was dissolved in tetrahydrofuran (5 mL) at room temperature under argon. To the stirring solution was added sodium methoxide (20 mg), followed by allyl bromide (55 mg). The resulting suspension was stirred for 16 h before dilution with ethyl acetate (20 mL) and water (20 mL). The organic phase was separated and dried over anhydrous sodium sulfate. After solvent evaporation under vacuum, the crude product was purified by reverse phase preparative HPLC to provide (S)-1-allyl-3-t-butyloxycarbonylamino-3,4-dihydrocarbostyril (10 mg).

(S)-1-allyl-3-t-butyloxycarbonylamino-3,4-dihydrocarbostyril (9.7 mg) was dissolved in 4 M hydrogen chloride in 1,4-dioxane solution (2 mL) at room temperature, and a white precipitate soon formed. After 30 min the solvent was evaporated under vacuum, and the residue was twice taken up in toluene (5 mL) and evaporated to provide (S)-1-allyl-3-amino-3,4-dihydrocarbostyril hydrochloride (7.6 mg).

(S)-1-allyl-3-amino-3,4-dihydrocarbostyril hydrochloride (7.6 mg) was added to a mixture of tetrahydrofuran (4 mL), 5-chloroindole-2-carboxylic acid (6.9 mg), 1-hydroxy-7-azabenzotriazole (5.5 mg), and 1-[3-(dimethylamino)propyl]-3-ethylcarbodiimide hydrochloride (7.7 mg) at room temperature. Diisopropylethylamine (12 mg) was added, and the resulting yellow suspension was stirred under argon for 16 h, during which a solution formed. The solution was evaporated under vacuum and the residue was directly purified by reverse phase preparative HPLC to provide the title compound (6.5 mg). HPLC/MS [M+H]$^+$, 380; HPLC/MS [M+Na]$^+$, 402.

EXAMPLE 17

(S)-3-(5-chloroindole-2-carbonylamino)-1-cyanomethyl-3,4-dihydrocarbostyril (S)-3-(5-chloroindole-2-carbonylamino)-3,4-dihydrocarbostyril (Example 4, 13.4 mg) was dissolved in tetrahydrofuran (5 mL) at room temperature under argon with stirring. After cooing to 0° C., sodium methoxide (4.3 mg) was added, followed 2 h later by bromoacetonitrile (7.2 mg). This was warmed to room temperature over 2 h, and 2 h later water (15 mL), 1.0 M aqueous hydrochloric acid (1 mL), and ethyl acetate (20 mL) were added. The organic phase was separated, washed with brine, and dried over anhydrous sodium sulfate. After solvent evaporation under vacuum, the crude product was purified by reverse phase preparative HPLC to provide the title compound (4 mg). HPLC/MS [M+H]$^+$, 379; HPLC/MS [M+Na]$^+$, 401.

EXAMPLE 18

(R)-3-(5-chloroindole-2-carbonylamino)-1-cyanomethyl-3,4-dihydrocarbostyril

The title compound was prepared from (R)-3-(5-chloroindole-2-carbonylamino)-3,4-dihydrocarbostyril (Example 3) by the procedures described for the preparation of (S)-3-(5-chloroindole-2-carbonylamino)-1-cyanomethyl-3,4-dihydrocarbostyril (Example 17) from (S)-3-(5-chloroindole-2-carbonylamino)-3,4-dihydrocarbostyril. HPLC/MS [M+H]$^+$, 379.

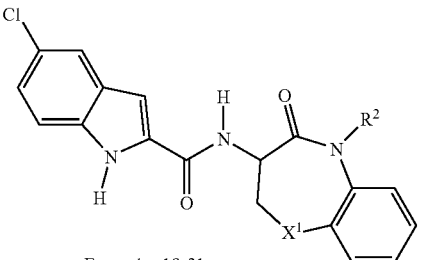

Examples 19-21
and 24-31
see table

| Example | X¹ | R² | Stereochemistry |
|---|---|---|---|
| 19 | CH₂ | H | racemate |
| 20 | O | H | S |
| 21 | O | H | R |
| 24 | S | H | racemate |
| 25 | SO₂ | H | racemate |
| 26 | S | H | S |
| 27 | CH₂ | CH₂CO₂H | S |
| 28 | CH₂ | CH₂CO₂H | R |
| 29 | S | CH₂CO₂H | racemate |
| 30 | SO₂ | CH₂CO₂H | racemate |
| 31 | O | CH₂CO₂H | S |

EXAMPLE 19

3-(5-chloroindole-2-carbonylamino)-2,3,4,5-tetrahydro-1H-1-benzazepin-2-one

The title compound was prepared according to the Carbodiimide Mediated Amide Bond Formation Procedure from 3-amino-2,3,4,5-tetrahydro-1H-1-benzazepin-2-one (amine prepared in Schoen, et al., J. Med. Chem. 1994, 37, 897-906). HPLC/MS [M+H]⁺, 354.

EXAMPLE 20

(S)-3-(5-chloroindole-2-carbonylamino)-2,3-dihydro-1,5-benzoxazepin-4(5H)-one

The title compound was prepared according to the Carbodiimide Mediated Amide Bond Formation Procedure from (S)-3-amino-2,3-dihydro-1,5-benzoxazepin-4(5H)-one trifluoroacetic acid salt (amine hydrochloride salt prepared in Itoh, et al., Chem. Pharm. Bull. 1986, 34, 1128-1147). HPLC/MS [M+H]⁺, 356.

Alternatively, to a mixture of (S)-3-amino-2,3-dihydro-1,5-benzoxazepin-4(5H)-one hydrochloride salt (54 mg) (prepared in Itoh, et al., Chem. Pharm. Bull. 1986, 34, 1128-1147), tetrahydrofuran (10 mL), 5-chloroindole-2-carboxylic acid (39 mg), 1-hydroxy-7-azabenzotriazole (31 mg), and 1-[3-(dimethylamino)propyl]-3-ethylcarbodiimide hydrochloride (57 mg) stirring at room temperature under argon was added diisopropylethylamine (65 mg). The resulting yellow suspension was stirred for 30 min, during which a solution formed. After evaporation under vacuum, the residue was redissolved in ethyl acetate (50 mL) and the resulting solution was washed sequentially with 1.0 M aqueous hydrochloric acid (25 mL), 1.0 M aqueous sodium hydroxide (25 mL), water (25 mL) and brine (25 mL), dried over anhydrous sodium sulfate, and evaporated under vacuum. The resulting solid crude product was triturated with diethyl ether (20 mL three times), followed by drying under vacuum to provide the title compound (63 mg).

EXAMPLE 21

(R)-3-(5-chloroindole-2-carbonylamino)-2,3-dihydro-1,5-benzoxazepin-4(5H)-one (R)-3-amino-2,3-dihydro-1,5-benzoxazepin-4(5H)-one hydrochloride salt was prepared from N-t-butyloxycarbonyl-D-serine by the procedures described in Itoh, et al., Chem. Pharm. Bull. 1986, 34, 1128-1147 for the preparation of (S)-3-amino-2,3-dihydro-1,5-benzoxazepin-4(5H)-one hydrochloride salt from N-t-butyloxycarbonyl-L-serine.

The title compound was prepared from (R)-3-amino-2,3-dihydro-1,5-benzoxazepin-4(5H)-one hydrochloride salt by the procedures described for the preparation of (S)-3-(5-chloroindole-2-carbonylamino)-2,3-dihydro-1,5-benzoxazepin-4(5H)-one (Example 20) from (S)-3-amino-2,3dihydro-1,5-benzoxazepin-4(5H)-one hydrochloride salt. HPLC/MS [M+H]⁺, 356.

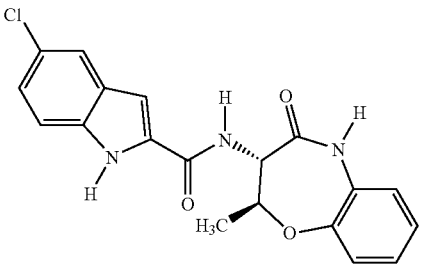

EXAMPLE 22

(2S,3S)-3-(5-chloroindole-2-carbonylamino)-2-methyl-2,3-dihydro-1,5-benzoxazepin-4(5H)-one (2S,3S)-3-amino-2-methyl-2,3-dihydro-1,5-benzoxazepin-4(5H)-one trifluoroacetate salt was prepared from (2S,3S)-3-t-butyloxycarbonylamino-2-methyl-2,3-dihydro-1,5-benzoxazepin-4(5H)-one (Robl, et al., Bioorg. & Med. Chem. Lett. 1994, 4, 1789-1794) by treatment with a solution of trifluoroacetic acid-dichloromethane-tetrahydrofuran (1:10:10) at room temperature, followed by solvent evaporation and coevaporation with tetrahydrofuran under vacuum.

The title compound was prepared from (2S,3S)-3-amino-2-methyl-2,3-dihydro-1,5-benzoxazepin-4(5H)-one trifluoroacetate salt according to the Carbodiimide Mediated Amide Bond Formation Procedure with the following modifications: the reaction solvent was N,N-dimethylformamide-tetrahydrofuran (1:1), the scavenger base was diisopropylethylamine, no attempt was made to hydrolyze any residual activated ester, no attempt was made to precipitate desired product, and the product was purified directly by reverse phase preparative HPLC. HPLC/MS [M+H]⁺, 370.

Example 23

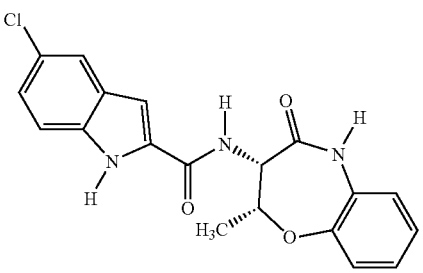

EXAMPLE 23

(2S,3R)-3-(5-chloroindole-2-carbonylamino)-2-methyl-2,3-dihydro-1,5-benzoxazepin-4 (5H)-one (2S,3R)-3-amino-2-methyl-2,3-dihydro-1,5-benzoxazepin-4(5H)-one trifluoroacetate salt was prepared from (2S,3R)-3-t-butyloxycarbonylamino-2-methyl-2,3-dihydro-1,5-benzoxazepin-4(5H)-one (Robi, et al., Bioorg. & Med. Chem. Lett. 1994, 4, 1789-1794) by treatment with a solution of trifluoroacetic acid-dichloromethane-tetrahydrofuran (1:10:10) at room temperature, followed by solvent evaporation and coevaporation with tetrahydrofuran under vacuum.

The title compound was prepared from (2S,3R)-3-amino-2-methyl-2,3-dihydro-1,5-benzoxazepin-4 (5H)-one trifluoroacetate salt by the procedures described for the preparation of (2S,3S)-3-(5-chloroindole-2-carbonylamino)-2-methyl-2,3-dihydro-1,5-benzoxazepin-4(5H)-one (Example 22) from (2S,3S)-3-amino-2-methyl-2,3-dihydro-1,5-benzoxazepin-4 (5H)-one trifluoroacetate salt. HPLC/MS [M+H]$^+$, 370.

EXAMPLE 24

3-(5-chloroindole-2-carbonylamino)-2,3-dihydro-1,5-benzthiazepin-4(5H)-one

3-Amino-2,3-dihydro-1,5-benzthiazepin-4(5H)-one trifluoroacetate salt was prepared from 3-t-butyloxycarbonylamino-2,3-dihydro-1,5-benzthiazepin-4(5H)-one (U.S. Pat. No. 4,512,988) by treatment with trifluoroacetic acid in dichloromethane at room temperature, followed by solvent evaporation under vacuum.

The title compound was prepared from 3-amino-2,3-dihydro-1,5-benzthiazepin-4(5H)-one trifluoroacetate salt according to the Carbodiimide Mediated Amide Bond Formation Procedure. HPLC/MS [M+H]$^+$, 372.

EXAMPLE 25

3-(5-chloroindole-2-carbonylamino)-2,3-dihydro-1,5-benzthiazepin-4(5H)-one S,S-dioxide To a solution of 3-(5-chloroindole-2-carbonylamino)-2,3-dihydro-1,5-benzthiazepin-4(5H)-one (Example 24) (5.6 mg) in tetrahydrofuran (2 mL) was added 60% 3-chloroperoxybenzoic acid (5.2 mg gross). After stirring at room temperature for 30 min, the mixture was directly injected onto reverse phase preparative HPLC, which separated the two sulfoxides from the title compound (2.5 mg). Further oxidation of the sulfoxides with 3-chloroperoxybenzoic acid in dichloromethane, followed by solvent evaporation under vacuum and reverse phase preparative HPLC provided title compound (1.0 mg). HPLC/MS [M+H]$^+$, 404.

EXAMPLE 26

(S)-3-(5-chloroindole-2-carbonylamino)-2,3-dihydro-1,5-benzthiazepin-4(5H)-one

The title compound was prepared according to the Carbodiimide Mediated Amide Bond Formation Procedure from (S)-3-amino-2,3-dihydro-1,5-benzthiazepin-4 (5H)-one trifluoroacetic acid salt (amine free base prepared in Slade, et al., J. Med. Chem. 1985, 28, 1517-1521). HPLC/MS [M+H]$^+$, 372.

EXAMPLE 27

(S)-1-carboxymethyl-3-(5-chloroindole-2-carbonylamino)-2,3,4,5-tetrahydro-1H-1-benzazepin-2-one The title compound was prepared in two steps according to the Carbodiimide Mediated Amide Bond Formation Procedure followed by the Ester Hydrolysis Procedure from (S)-1-carboethoxymethyl-3-amino-2,3,4,5-tetrahydro-1H-1-benzazepin-2-one L-tartaric acid salt (amine L-tartaric acid salt prepared in Watthey, et al., J. Med. Chem. 1985, 28, 1511-1516). HPLC/MS [M+H]$^+$, 412.

EXAMPLE 28

(R)-1-carboxymethyl-3-(5-chloroindole-2-carbonylamino)-2,3,4,5-tetrahydro-1H-1-benzazepin-2-one The title compound was prepared in two steps according to the Carbodiimide Mediated Amide Bond Formation Procedure followed by the Ester Hydrolysis Procedure from (R)-1-carboethoxymethyl-3-amino-2,3,4,5-tetrahydro-1H-1-benzazepin-2-one D-tartaric acid salt ((R)-amine D-tartaric acid salt prepared analogously to enantiomer in Watthey, et al., J. Med. Chem. 1985, 28, 1511-1516). HPLC/MS [M+H]$^+$, 412.

EXAMPLE 29

1-carboxymethyl-3-(5-chloroindole-2-carbonylamino)-2,3-dihydro-1,5-benzthiazepin-4(5H)-one The title compound was prepared in two steps according to the Carbodiimide Mediated Amide Bond Formation Procedure followed by the Ester Hydrolysis Procedure from 1-carboethoxymethyl-3-amino-2,3-dihydro-1,5-benzthiazepin-4 (5H)-one hydrochloride salt (amine free base prepared in U.S. Pat. No. 4,512,988). HPLC/MS [M+H]$^+$, 430.

EXAMPLE 30

1-carboxymethyl-3-(5-chloroindole-2-carbonylamino)-2,3-dihydro-1,5-benzthiazepin-4(5H)-one S,S-dioxide To a solution of 1-carboxymethyl-3-(5-chloroindole-2-carbonylamino)-2,3-dihydro-1,5-benzthiazepin-4(5H)-one (Example 29) (3.7 mg) in dichloromethane (15 mL) at 0° C. was added 60% 3-chloroperoxybenzoic acid (5.2 mg gross). After stirring while slowly warming to room temperature over 1 h, water (15 mL) was added. This mixture was stirred for 30 min, the layers were separated, and the organic phase was washed sequentially with 10% aqueous sodium bisulfite solution, 1.0 M aqueous sodium hydroxide solution (10 mL), and brine (10 mL). After drying over anhydrous sodium sulfate, the solvent was evaporated under vacuum, and the residue was purified by reverse phase preparative HPLC to obtain the title compound (2.7 mg). HPLC/MS [M+H]$^+$, 462.

EXAMPLE 31

(S)-1-carboxymethyl-3-(5-chloroindole-2-carbonylamino)-2,3-dihydro-1,5-benzoxazepin-4(5H)-one The title compound was prepared in two steps according to the Carbodiimide Mediated Amide Bond Formation Procedure followed by the Ester Hydrolysis Procedure from (S)-1-carboethoxymethyl-3-amino-2,3-dihydro-1,5-benzoxazepin-4(5H)-one hydrochloride salt (amine hydrochloride salt prepared in U.S. Pat. No. 5,552,397). HPLC/MS [M+H]$^+$, 414.

Example 32

EXAMPLE 32

(R)-4-(5-chloroindole-2-carbonylamino)-2,3,4,5-tetrahydro-2-benzazepin-3(1H)-one (R)-4-amino-2,3,4,5-tetrahydro-2-benzazepin-3(1H)-one hydrochloride salt (387 mg) (amine free base prepared in U.S. Pat. No. 5,545,735) was added to a mixture of tetrahydrofuran (40 mL), 5-chloroindole-2-carboxylic acid (356 mg), 1-hydroxy-7-azabenzotriazole (272 mg), and 1-[3(dimethylamino)propyl]-3-ethylcarbodiimide hydrochloride (382 mg) at room temperature. Diisopropylethylamine (202 mg) was added, and the resulting yellow suspension was stirred under argon for 16 h, during which a solution formed. The solution was evaporated under vacuum and the residue was redissolved in ethyl acetate (100 mL). This was washed sequentially with 1.0 M aqueous hydrochloric acid (50 mL), 1.0 M aqueous sodium hydroxide (50 mL), water (50 mL) and brine (50 mL), dried over anhydrous sodium sulfate, and evaporated under vacuum. The resulting solid crude product was triturated with 20% methanol in diethyl ether (20 mL four times). Drying under vacuum provided pure title compound (283 mg). HPLC/MS [M+H]+, 354.

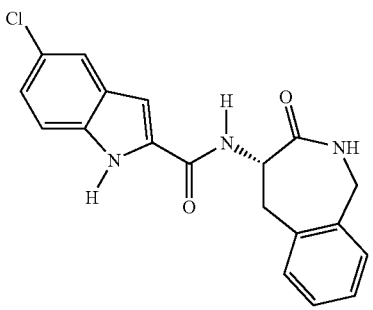

Example 33

EXAMPLE 33

(S)-4-(5-chloroindole-2-carbonylamino)-2,3,4,5-tetrahydro-2-benzazepin-3(1H)-one To a solution of (S)-L-(2-cyanophenyl)alanine (1.0 g) in acetonitrile (30 mL) at room temperature was added di-t-butyl dicarbonate (1.7 g), followed by saturated aqueous sodium carbonate (20 mL, slowly). After stirring for 16 h, the acetonitrile was removed under vacuum, and the aqueous layer was extracted with ethyl acetate (50 mL three times). The combined organic layers were washed sequentially with 0.5 M aqueous hydrochloric acid (50 mL) and brine (50 mL) before drying over anhydrous sodium sulfate and evaporation under vacuum to provide (S)-N-t-butyloxycarbonyl(2-cyanophenyl)alanine (1.4 g).

A mixture of (S)-N-t-butyloxycarbonyl(2-cyanophenyl)alanine (1.0 g), Raney® Nickel (1.0 g), and methanol (20 mL) was hydrogenated in a Parr apparatus at 50 psi for 60 h at room temperature. The catalyst was filtered and rinsed with methanol (20 mL three times). The combined filtrate and rinses were evaporated under vacuum, and the resulting residue was triturated with diethyl ether (30 mL five times) to obtain (S)-N-t-butyloxycarbonyl(2-aminomethylphenyl)alanine (406 mg).

A mixture of (S)-N-t-butyloxycarbonyl(2-aminomethylphenyl)alanine (353 mg), N,N-dimethylformamide (10 mL), dichloromethane (50 mL), 1-hydroxy-7-azabenzotriazole (252 mg), and 1-[3-(dimethylamino)propyl]-3-ethylcarbodiimide hydrochloride (180 mg) was stirred at room temperature for 1 h. The solvent was removed under vacuum and the residue was dissolved ethyl acetate (100 mL). This solution was washed sequentially with 1.0 M aqueous hydrochloric acid (50 mL twice), 1.0 M aqueous sodium hydroxide (50 mL), water (50 mL), and brine (50 mL), dried over anhydrous sodium sulfate, and evaporated under vacuum to obtain (S)-4-(t-butyloxycarbonylamino)-2,3,4,5-tetrahydro-2-benzazepin-3(1H)-one (315 mg).

(S)-4-(t-butyloxycarbonylamino)-2,3,4,5-tetrahydro-2-benzazepin-3(1H)-one (276 mg) was dissolved in 2 M hydrogen chloride in diethyl ether solution (25 mL) at room temperature. A precipitate slowly formed. After 16 h stirring the solvent was evaporated under vacuum. The residue was twice taken up in toluene (10 mL) and evaporated to provide (S)-4-amino-2,3,4,5-tetrahydro-2-benzazepin-3(1H)-one hydrochloride, which was used directly in the next step.

A mixture of (S)-4-amino-2,3,4,5-tetrahydro-2-benzazepin-3(1H)-one hydrochloride (all of that prepared above), tetrahydrofuran (25 mL), 5-chloroindole-2-carboxylic acid (198 mg), 1-hydroxy-7-azabenzotriazole (150 mg), and 1-[3-(dimethylamino)propyl]-3-ethylcarbodiimide hydrochloride (210 mg) was stirred at room temperature. Diisopropylethylamine (202 mg) was added, and after 16 h the resulting yellow solution was evaporated under vacuum. The residue was dissolved in ethyl acetate (150 mL), and this was washed sequentially with 1.0 M aqueous hydrochloric acid (50 mL twice), 1.0 M aqueous sodium hydroxide (50 mL), water (50 mL), and brine (25 mL), dried over anhydrous sodium sulfate, and evaporated under vacuum to provide crude product. The product was crystallized by dissolving in warm methanol (40 mL) and adding diethyl ether (100 mL). The crystals were filtered, washed with diethyl ether (30 mL twice), and dried under vacuum to provide the title compound (181 mg). HPLC/MS [M+H]+, 354.

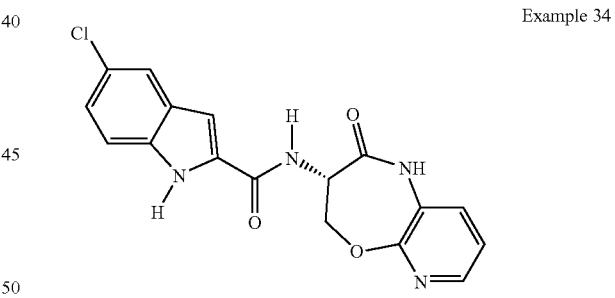

Example 34

EXAMPLE 34

(S)-9-aza-3-(5-chloroindole-2-carbonylamino)-2,3-dihydro-1,5-benzoxazepin-4(5H)-one To a stirring solution of N-t-butyloxycarbonyl-L-serine (2.26 g) in N,N-dimethylformamide (15 mL) under argon at −20° C. was slowly added sodium hydride (60% oil dispersion, 0.88 g gross weight). The resulting mixture was warmed to 0° C. for 1 h, then recooled to −20° C. before a solution of 2-chloro-3-nitropyridine (1.6 g) in N,N-dimethylformamide (10 mL) was added over 10 min. The resulting red solution was stirred at −20° C. for 1 h. Water (100 mL) was then added, and the mixture was washed with diethyl ether (30 mL twice). The aqueous layer was adjusted to pH 7 with 1.0 M aqueous hydrochloric acid and extracted with ethyl acetate (30 mL three times). The combined extracts were washed with brine (50 mL), dried over anhydrous sodium sulfate, and evaporated under vacuum. The resulting residue was purified by silica gel chromatography eluting with ethyl acetate-hexane (1:2) to obtain N-t-butyloxycarbonyl-O-(3-nitro-2-pyridyl)-L-serine (2.46 g).

A mixture of N-t-butyloxycarbonyl-O-(3-nitro-2-pyridyl)-L-serine (500 mg) and 10% palladium on carbon (50 mg) in methanol (30 mL) was hydrogenated under a hydrogen balloon for 6 h. The catalyst was filtered off, rinsing with methanol (15 mL twice). The filtrate was evaporated under vacuum, and the residue was purified by reverse phase preparative HPLC using trifluoroacetic acid containing solvents. The preparative HPLC fractions were partially evaporated at 0° C. under vacuum before lyophilization to provide N-t-butyloxycarbonyl-O-(3-amino-2-pyridyl)-L-serine trifluoroacetic acid salt (475 mg).

To a suspension of N-t-butyloxycarbonyl-O-(3-amino-2-pyridyl)-L-serine trifluoroacetic acid salt (473 mg) in tetrahydrofuran (25 mL) stirring at room temperature under argon was added 1-hydroxy-7-azabenzotriazole (188 mg), 1-[3-(dimethylamino)propyl]-3-ethylcarbodiimide hydrochloride (264 mg), and then diisopropylethylamine (297 mg). After 17 h the mixture was evaporated under vacuum and reverse phase preparative HPLC using trifluoroacetic acid containing solvents provided (S)-9-aza-3-t-butyloxycarbonylamino-2,3-dihydro-1,5-benzoxazepin-4(5H)-one trifluoroacetic acid salt (142 mg).

(S)-9-aza-3-t-butyloxycarbonylamino-2,3-dihydro-1,5-benzoxazepin-4(5H)-one trifluoroacetic acid salt (40 mg) was dissolved in dichloromethane (5 mL) and 4 M hydrogen chloride in dioxane solution (2 mL) at room temperature. After 16 h the solvent was evaporated under vacuum, and the residue was twice taken up in toluene (10 mL) and evaporated to provide (S)-9-aza-3-amino-2,3-dihydro-1,5-benzoxazepin-4(5H)-one hydrochloride, all of which was used directly in the next step.

A mixture of (S)-9-aza-3-amino-2,3-dihydro-1,5-benzoxazepin-4(5H)-one hydrochloride, tetrahydrofuran (15 mL), 5-chloroindole-2-carboxylic acid (12 mg), 1-hydroxy-7-azabenzotriazole (8 mg), 1-[3-(dimethylamino)propyl]-3-ethylcarbodiimide hydrochloride (11.5 mg), and diisopropylethylamine (15.5 mg) was stirred at room temperature under argon for 16 h. The solvent was evaporated under vacuum and purification by reverse phase preparative HPLC provided the title compound (18.9 mg). HPLC/MS [M+H]$^+$, 357.

Example 35

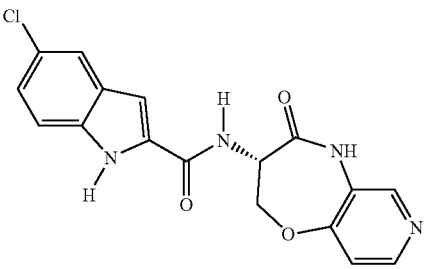

EXAMPLE 35

(S)-7-aza-3-(5-chloroindole-2-carbonylamino)-2,3-dihydro-1,5-benzoxazepin-4(5H)-one The title compound was prepared analogously to (S)-9-aza-3-(5-chloroindole-2-carbonylamino)-2,3-dihydro-1,5-benzoxazepin-4(5H)-one (Example 34) using 4-chloro-3-nitropyridine in place of 2-chloro-3-nitropyridine. MS [M+H]$^+$, 357.

Example 36

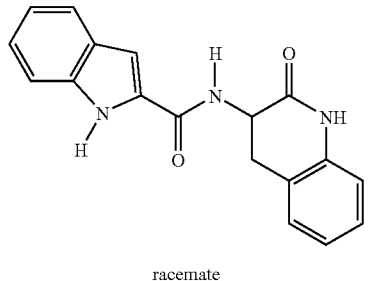

racemate

EXAMPLE 36

3-(indole-2-carbonylamino)-3,4-dihydrocarbostyril

The title compound was prepared by the methods of Example 5 using 3-amino-3,4-dihydrocarbostyril hydrochloride in place of (R)-3-amino-3,4-dihydrocarbostyril hydrochloride and indole-2-carboxylic acid in place of 5-chloroindole-2-carboxylic acid. HPLC/MS [M+H]$^+$, 306; [M+Na]$^+$, 328.

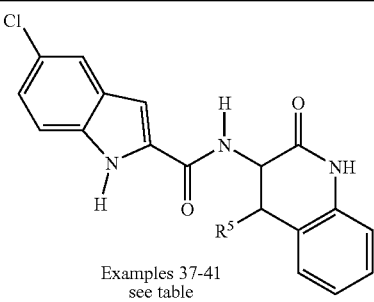

Examples 37-41
see table

| Example | R$^5$ | Stereochemistry |
|---|---|---|
| 37 | CH$_2$CO$_2$CH$_3$ | trans racemate |
| 38 | CH$_2$CO$_2$CH$_3$ | cis racemate |
| 39 | CH$_2$CO$_2$H | trans racemate |
| 40 | CH$_2$CO$_2$H | trans homochiral enantiomers |
| 41 | CH$_2$CONHCH$_2$C$_6$H$_5$ | cis - trans racemate |

EXAMPLE 37

(3R*,4S*)-4-carbomethoxymethyl-3-(5-chloroindole-2-carbonylamino)-3,4-dihydrocarbostyril (trans racemate)

To a stirred solution of 3-(2-aminophenyl)propenoic acid methyl ester (2.0 g, 11.3 mmol) and triethylamine (3.3 mL, 23.7 mmol) in tetrahydrofuran (36 mL) at room temperature under argon was added 20% w/w phosgene in toluene solution (7 g, 14.1 mmol). After 1 h, a solution of nitromethane (2.9 mL, 54 mmol) in tetrahydrofuran (200 mL) containing 1 M potassium t-butoxide in tetrahydrofuran solution (62 mL, 62 mmol) was added via cannula. The mixture was stirred for 1 h before it was poured into ice-cold 1 M aqueous hydrochloric acid (300 mL). The resulting mixture was extracted with ice-cold diethyl ether (300 mL three times). The combined organic extracts were dried over anhydrous sodium sulfate, and the solvent was evaporated under vacuum to give crude 3-(2-(nitroacetylamino)phenyl)propenonic acid methyl ester (1 g, 72% pure) as an orange solid. HPLC/MS [M+H]+, 265.

A 50 mL round-bottom flask was charged with crude 3-(2-(nitroacetylamino)phenyl)propenonic acid methyl ester (100 mg), methanol (20 mL) and 0.5 M sodium methoxide in methanol solution (2.3 mL). After stirring 18 h at room temperature under argon, with reaction progress monitored by diminution of UV absorbance at 280 nm, the reaction was quenched with glacial acetic acid (5 mL). Raney® Nickel (100 mg of 50% w/w water slurry) was added, and the atmosphere evacuated and charged four times with hydrogen gas (1 atm). After the mixture was stirred vigorously for 3 h at room temperature, the vessel was flushed with nitrogen, and the mixture was allowed to settle. The supernatant was decanted, and solvent evaporation under vacuum gave a green solid which was purified by reverse phase preparative HPLC using trifluoroacetic acid containing solvents to obtain 3-amino-4-carbomethoxymethyl-3,4-dihydrocarbostyril trifluoroacetic acid salt (24 mg, 7% overall yield from 3-(2-aminophenyl)propenoic acid methyl ester) as a white solid. This material was comprised of two fractions, a 3:1 mixture of cis and trans isomers (11 mg) and pure trans isomer (13 mg). Cis isomer: $^1$H NMR (CD$_3$OD, 400 MHz) δ 7.40-7.03 (m, 4H), 4.55 (d, 1H, J=4.7 Hz), 3.9-3.85 (m, 1H), 3.81 (s, 3H), 2.82 (dd, 1H, J=4.8, 15.8 Hz), 2.50 (dd, 1H, J=9.6, 15.8 Hz). Trans isomer: $^1$H NMR (CD$_3$OD, 400 MHz) d 7.33-7.25 (m, 2H), 7.14-7.00 (m, 1H), 6.98 (d, 1H, J=7.9 Hz), 4.41 (d, 1H, J=12.3 Hz), 3.74 (s, 3H), 3.65-3.61 (m, 1H), 3.20 (dd, 1H, J=4.3, 17.8 Hz), 2.95 (dd, 1H, J=6.1, 17.6 Hz).

A 1 mL reaction vessel was charged with trans 3-amino-4-carbomethoxymethyl-3,4-dihydrocarbostyril trifluoroacetic acid salt (13 mg, 0.04 mmol), 1-[3-(dimethylamino)propyl]-3-ethylcarbodiimide hydrochloride (9 mg, 0.05 mmol), 1-hydroxy-7-azabenzotriazole (7 mg, 0.05 mmol), 5-chloroindole-2-carboxylic acid (8 mg, 0.04 mmol) and N,N-dimethylformamide (0.3 mL). After the solids dissolved during stirring at room temperature under argon, diisopropylethylamine (14 mg, 0.11 mmol) was added, and the solution was stirred for 1 h before it was diluted with water (0.2 mL) and methanol (0.8 mL). Purification by reverse phase preparative HPLC using trifluoroacetic acid containing solvents gave the title compound (8.5 mg, 56% yield) as a white solid. $^1$H NMR (d$_8$-THF, 400 MHz) δ 11.2 (s, 1H), 9.6 (s, 1H), 8.06 (d, 1H, J=8.9 Hz), 7.64 (d, 1H, J=1.9 Hz), 7.43 (d, 1H, J=8.7 Hz), 7.24-6.87 (m, 6H), 4.84 (dd, 1H, J=8.8, 13.0 Hz), 3.67 (m, 1H), 3.59 (s, 3H), 2.89 (d, 2H, J=6.2 Hz). HPLC/MS [M+H]+, 412.

EXAMPLE 38

(3R*,4R*)-4-carbomethoxymethyl-3-(5-chloroindole-2-carbonylamino)-3,4-dihydrocarbostyril (cis racemate)

Following the procedure for the last step of Example 37, the title compound was prepared from a 3:1 mixture of cis and trans, respectively, 3-amino-4-carbomethoxymethyl-3,4-dihydrocarbostyril trifluoroacetic acid salt (prepared in Example 37). The title compound of Example 37 was also isolated by reverse phase preparative HPLC, eluting just after the title compound of Example 38. $^1$H NMR (CD$_3$OD, 400 MHz) δ 7.64-6.93 (m, 8H), 5.03 (d, 1H, J=5.7 Hz), 3.93-3.91 (m, 1H), 3.50 (s, 3H), 2.73 (dd, 1H, J=5.2, 15.3 Hz), 2.36 (dd, 1H, J=9.5, 15.2 Hz). HPLC/MS [M+H]+, 412.

EXAMPLE 39

(3R*,4S*)-4-carboxymethyl-3-(5-chloroindole-2-carbonylamino)-3,4-dihydrocarbostyril (trans racemate)

A 250 mL round-bottom flask was charged with 3-(2-aminophenyl)propenoic acid methyl ester (600 mg, 3.39 mmol) and THF (100 mL), and the resulting solution was cooled to 0° C. To this was added dicyclohexylcarbodiimide (880 mg, 4.26 mmol) and of nitroacetic acid (prepared according to Huang, et al., J. Org. Chem. 2000, 65, 499-503) (430 mg, 4.0 mmol). The reaction solution was stirred for 2 h at 0° C. (solids formed) before warming to room temperature and filtration. The filtrate was evaporated under vacuum to obtain crude 3-(2-(nitroacetylamino)phenyl)propenonic acid methyl ester (1.0 g, 82.5% pure) as a tan solid.

A 500 mL round-bottom flask was charged with crude 3-(2-(nitroacetylamino)phenyl)propenonic acid methyl ester (1.0 g), methanol (190 mL), and after degassing by argon sparge for 30 min, 0.5 M sodium methoxide in methanol solution (23 mL). After stirring 5 h at room temperature under argon, with reaction progress monitored by diminution of UV absorbance at 280 nm, the reaction mixture was cooled to −30° C. and 2 M hydrogen chloride in ether solution (7 mL) was added slowly. After partial solvent evaporation to 30 mL at 0° C. under vacuum, the resulting solution was transferred to a 100 mL round-bottom flask containing dry Raney® Nickel (400 mg, prepared from 50% w/w water slurry by repetitive rinsing with methanol (5 mL three times) and solvent evaporation under vacuum). The resulting mixture was stirred vigorously for 14 h at room temperature under hydrogen (1 atm) before it was transferred to a pressure bottle to continue hydrogenation at 40 psi for 2 h. The supernatant was decanted and evaporated under vacuum. The residue was taken up in a mixture of water (200 mL) and diethyl ether (100 mL). After separation of the aqueous layer, the organic layer (containing suspended solids) was diluted with ethyl acetate (50 mL) and extracted with water (100 mL). The combined aqueous extracts were evaporated under vacuum to dryness to obtain crude 3-amino-4-carbomethoxymethyl-3,4-dihydrocarbostyril hydrochloride (1.2 g).

Crude 3-amino-4-carbomethoxymethyl-3,4-dihydrocarbostyril hydrochloride (1.2 g) was slurried in N,N-dimethylformamide (11 mL) with 1-[3-(dimethylamino)propyl]-3-ethylcarbodiimide hydrochloride (340 mg), 1-hydroxy-7-azabenzotriazole (240 mg), 5-chloroindole-2-carboxylic acid (300 mg) and diisopropylethylamine (525 mg, added last). The reaction mixture was stirred for 14 h at room temperature before dilution with ethyl acetate (200 mL) and 1.0 M aqueous hydrochloric acid solution (100 mL). After separation of the organic layer, the aqueous layer was extracted with ethyl acetate (50 mL). The combined organic layers were washed sequentially with 1.0 M aqueous hydrochloric acid solution (100 mL three times), 1.0 M aqueous sodium hydroxide solution (100 mL twice), and brine (100 mL), before drying over anhydrous magnesium sulfate and evaporation under vacuum to obtain crude cis-trans racemic 4-carbomethoxymethyl-3-(5-chloroindole-2-carbonylamino)-3,4-dihydrocarbostyril (360 mg, 26% overall yield from 3-(2-aminophenyl)propenoic acid methyl ester) as a tan solid.

Crude cis-trans racemic 4-carbomethoxymethyl-3-(5-chloroindole-2-carbonylamino)-3,4-dihydrocarbostyril (360 mg, 0.87 mmol) was dissolved in tetrahydrofuran (6 mL) with lithium hydroxide monohydrate (73 mg, 1.74 mmol) and water (2 mL). After 1 h, 1.0 M aqueous hydrochloric acid solution (1.8 ml) was added and the mixture was evaporated under vacuum to dryness. Epimerization under these hydrolysis conditions produced a 2:1 cis to trans ratio of products. Purification by reverse phase preparative HPLC using trifluoroacetic acid containing solvents gave the title compound (80 mg, 23% yield) as a tan solid. The cis isomer of the title compound was also isolated.

EXAMPLE 40

(3R*,4S*)-4-carboxymethyl-3-(5-chloroindole-2-carbonylamino)-3,4-dihydrocarbostyril (trans homochiral isomers)

Separation of (3R*,4S*)-4-carboxymethyl-3-(5-chloroindole-2-carbonylamino)-3,4-dihydrocarbostyril (trans racemate), the title compound of Example 39, into its component enantiomers was accomplished by chiral normal phase preparative HPLC (Chiralcel OD column, elution solvent: methanol containing 0.05% trifluoroacetic acid). High resolution MS calculated for [M–H]$^-$, 396.0751.

First isomer to elute: high resolution MS [M–H]$^-$ found 396.0770. $\alpha_D$ (21.5° C.)=+154.8 (c=0.50, methanol).

Second isomer to elute: high resolution MS [M–H]$^-$ found 396.0770. $\alpha_D$ (21.5° C.)=–127.0 (c=0.50, methanol).

EXAMPLE 41

4-benzylaminocarbonylmethyl-3-(5-chloroindole-2-carbonylamino)-3,4-dihydrocarbostyril (cis-trans racemate)

To a 1 dram vial was added 4-carboxymethyl-3-(5-chloroindole-2-carbonylamino)-3,4-dihydrocarbostyril as a 2:1 cis-trans racemate (mixture of the Example 39 title compound and its cis isomer, see Example 39) (9 mg, 0.02 mmol), N,N-dimethylformamide (0.2 mL), 1-[3-(dimethylamino)propyl]-3-ethylcarbodiimide hydrochloride (5 mg, 0.02 mmol), and benzylamine (0.01 mL, 0.05 mmol). After the solution was stirred for 14 h, additional 1-[3-(dimethylamino)propyl]-3-ethylcarbodiimide hydrochloride (10 mg) and benzylamine (0.015 mL) were added. The solution was stirred for 24 h more before dilution with 75% methanol in water (1.3 mL) and direct injection to reverse phase preparative HPLC, which provided the title compound (3.5 mg) as a white solid. HPLC/MS [M+H]$^+$, 487; [M–H]$^-$, 485.

Examples 42-44 and 47-55 can be prepared by one skilled in the art using the schemes and procedures in other examples contained herein. These examples serve to further illustrate, but not limit, the scope of the present invention.

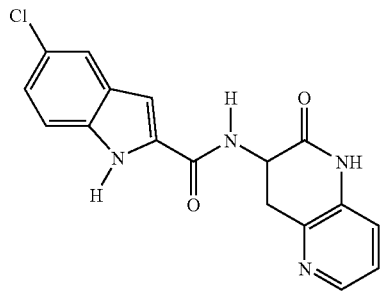

EXAMPLE 42 use Scheme 19, 17, AND 11

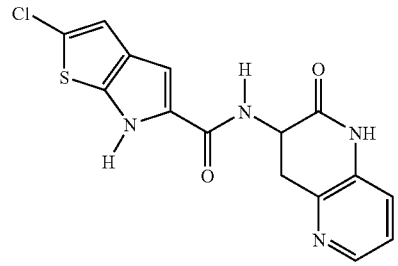

EXAMPLE 43 use Schemes 19, 17, AND 11

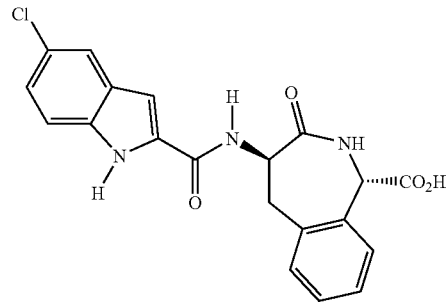

EXAMPLE 44 use Scheme 27

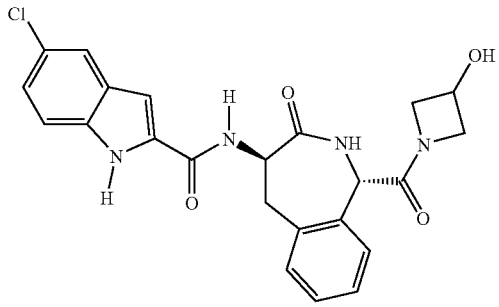

EXAMPLE 45

(1S,4R)-4-(5-chloroindole-2-carbonylamino)-1-(3-hydroxyazetidin-1-ylcarbonyl)-2,3,4,5-tetrahydro-2-benzazepin-3(1H)-one N-phthaloyl-D-phenylalanyl-α-methoxyglycine methyl ester was prepared from N-phthaloyl-D-phenylalaninamide by the procedures described in Flynn, et al., Biorg. & Med. Chem. Lett. 1991, 1, 309-312 for the preparation of N-phthaloyl-L-phenylalanyl-α-methoxyglycine methyl ester from N-phthaloyl-L-phenylalaninamide.

N-phthaloyl-D-phenylalanyl-α-methoxyglycine methyl ester (2.5 g) was stirred at 0° C. in a mixture of dichloromethane (2 mL) and concentrated sulfuric acid (30 mL) for 16 h before ice (100 g) was added. The resulting mixture was stirred for 24 h during which the temperature was allowed to rise to room temperature. The solid product was filtered, washed with water (10 mL twice), and dried under vacuum to provide a mixture (1:7) of desired (1S,4R) and undesired (1R,4R)-1-carbomethoxy-4-(N-phthaloylamino)-2,3,4,5-tetrahydro-2-benzazepin-3(1H)-one (1.7 g) as a white solid.

Ester hydrolysis and epimerization to a more favorable diastereoisomeric ratio were accomplished with coincident half hydrolysis and regeneration of the phthalimide protecting group as follows. To a solution of a 1:7 mixture of (1S,4R) and (1R,4R)-1-carbomethoxy-4-(N-phthaloylamino)-2,3,4,5-tetrahydro-2-benzazepin-3(1H)-one (1.0 g) in methanol (10 mL), tetrahydrofuran (10 mL), and water (10 mL) stirring at room temperature under argon was added 1.0 M aqueous lithium hydroxide solution (2.75 mL). After 16 h HPLC analysis indicated that the ratio of (1S,4R) to (1R,4R) intermediates was 3:2. Acetic acid was added until the mixture reached pH 4, and the solvent was largely evaporated under vacuum. The residue was partitioned between ethyl acetate (50 mL) and water (50 mL), and the organic layer was dried over anhydrous sodium sulfate and evaporated under vacuum. The resulting solid was dissolved in tetrahydrofuran (25 mL) and stirred under argon at room temperature as 1-[3-dimethylamino)propyl]-3-ethylcarbodiimide hydrochloride (0.69 g) and 1-hydroxy-7-azabenzotriazole (0.49 g) were added. After 1 h water (2 mL) was added, and the mixture was stirred for 16 h more at room temperature. The solvent was evaporated under vacuum and the residue was purified by reverse phase preparative HPLC using trifluoroacetic acid containing solvents, which provided the desired (1S,4R)-1-carboxy-4-(N-phthaloylamino)-2,3,4,5-tetrahydro-2-benzazepin-3(1H)-one (0.17 g) and undesired (1R,4R) diastereomer (0.11 g) (desired (1S,4R) isomer elutes after undesired (1R,4R) isomer).

A mixture of (1S,4R)-1-carboxy-4-(N-phthaloylamino)-2,3,4,5-tetrahydro-2-benzazepin-3(1H)-one-(40 mg), 3-hydroxyazetidine trifluoroacetic acid salt (26 mg), 1-[3-dimethylamino)propyl]-3-ethylcarbodiimide hydrochloride (26 mg), 1-hydroxy-7-azabenzotriazole (17 mg), and triethylamine (23 mg) in tetrahydrofuran (2 mL) was stirred under argon at room temperature for 16 h. The solvent was evaporated under vacuum and the residue was purified by reverse phase preparative HPLC using trifluoroacetic acid containing solvents, to provide (1S,4R)-1-(3-hydroxyazetidin-1-ylcarbonyl)-4-(N-phthaloylamino)-2,3,4,5-tetrahydro-2-benzazepin-3(1H)-one (20 mg) as a gum.

To a solution of (1S,4R)-1-(3-hydroxyazetidin-1-ylcarbonyl)-4-(N-phthaloylamino)-2,3,4,5-tetrahydro-2-benzazepin-3(1H)-one (20 mg) in methanol (2 mL) stirring at room temperature under argon was added hydrazine (16 mg). After 16 h the solvent was evaporated under vacuum, and the residue was coevaporated with tetrahydrofuran (5 mL twice) to provide crude (1S,4R)-4-amino-1-(3-hydroxyazetidin-1-ylcarbonyl)-2,3,4,5-tetrahydro-2-benzazepin-3(1H)-one, which without purification, was coupled with 5-chloroindole-2-carboxylic acid according to the Carbodiimide Mediated Amide Bond Formation Procedure with the following modifications: the reaction solvent was tetrahydrofuran, no attempt was made to hydrolyze any residual activated ester, no attempt was made to precipitate desired product, and the product was purified directly by reverse phase preparative HPLC using trifluoroacetic acid containing solvents, to provide the title compound (1.3 mg). MS [M+H]+, 453.

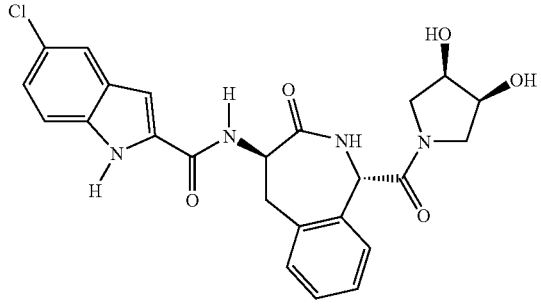

EXAMPLE 46

(1S,4R)-4-(5-chloroindole-2-carbonylamino)-1-(3,4-cis-dihydroxypyrrolidin-1-ylcarbonyl)-2,3,4,5-tetrahydro-2-benzazepin-3(1H)-one A mixture of (1S,4R)-1-carboxy-4-(N-phthaloylamino)-2,3,4,5-tetrahydro-2-benzazepin-3(1H)-one (100 mg) (prepared in Example 45), 3,4-isopropylidinedioxypyrrolidine (49 mg), 1-[3dimethylamino)propyl]-3-ethylcarbodiimide hydrochloride (65 mg), and 1-hydroxy-7-azabenzotriazole (46 mg) in tetrahydrofuran (5 mL) was stirred under argon at room temperature for 2 h. The solvent was evaporated under vacuum and the residue was purified by reverse phase preparative HPLC using trifluoroacetic acid containing solvents, to provide (1S,4R)-1-(3,4-isopropylidinedioxypyrrolidin-1-ylcarbonyl)-4-(N-phthaloylamino)-2,3,4,5-tetrahydro-2-benzazepin-3(1H)-one (87 mg) as a gum.

To a solution of (1S,4R)-1-(3,4-isopropylidinedioxypyrrolidin-1-ylcarbonyl)-4-(N-phthaloylamino)-2,3,4,5-tetrahydro-2-benzazepin-3(1H)-one (80 mg) in methanol (3 mL) stirring at room temperature under argon was added hydrazine (54 mg). After 16 h the solvent was evaporated under vacuum, and the residue was coevaporated with toluene (5 mL twice) and tetrahydrofuran (5 mL) to provide crude (1S,4R)-4-amino-1-(3,4-isopropylidinedioxypyrrolidin-1-ylcarbonyl)-2,3,4,5-tetrahydro-2-benzazepin-3(1H)-one, which without purification, was coupled with 5-chloroindole-2-carboxylic acid according to the Carbodiimide Mediated Amide Bond Formation Procedure with the following modifications: the reaction solvent was N,N-dimethylformamide-tetrahydrofuran (1:3), no attempt was made to hydrolyze any residual activated ester, no attempt was made to precipitate desired product, and the product was purified directly by reverse phase preparative HPLC using trifluoroacetic acid containing solvents, to provide (1S,4R)-4-(5-chloroindole-2-carbonylamino)-1-(3,4-isopropylidinedioxypyrrolidin-1-ylcarbonyl)-2,3,4,5-tetrahydro-2-benzazepin-3(1H)-one (13 mg).

(1S,4R)-4-(5-chloroindole-2-carbonylamino)-1-(3,4-isopropylidinedioxypyrrolidin-1-ylcarbonyl)-2,3,4,5tetrahydro-2-benzazepin-3(1H)-one (10 mg) was dissolved in a 1:1 mixture of trifluoroacetic acid and dichloromethane (2 mL), and the resulting solution was stirred under argon at room temperature for 16 h before the solvent was evaporated under vacuum and the residue was purified by reverse phase preparative HPLC using trifluoroacetic acid containing solvents, to provide the title compound (0.7 mg). MS [M+H]+, 483.

EXAMPLE 47
use Scheme 27
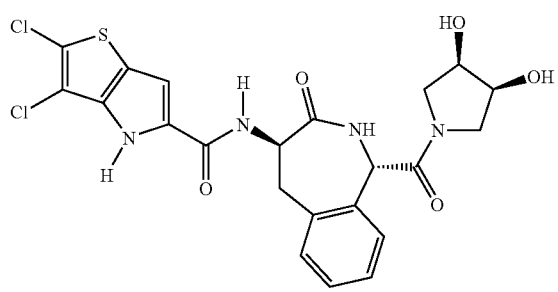
EXAMPLE 48
see Example 34
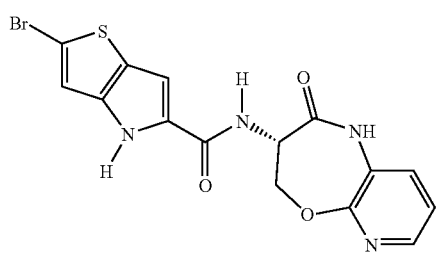
EXAMPLE 49
see Example 35
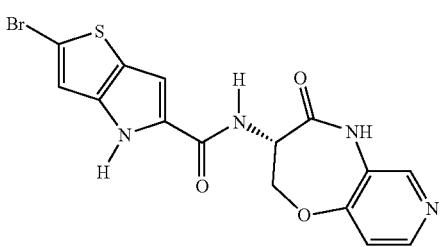
EXAMPLE 50
see Example 39
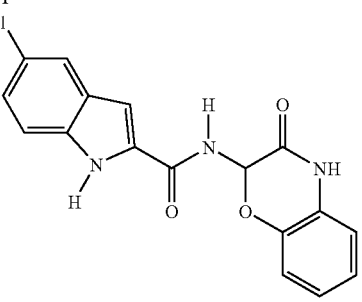
EXAMPLE 51
use Schemes 23, 22, and 11
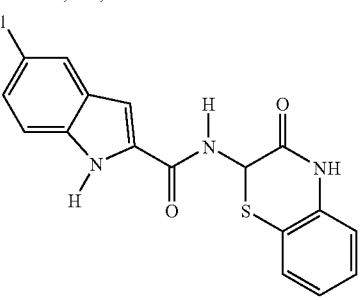
EXAMPLE 52
use Scheme 11
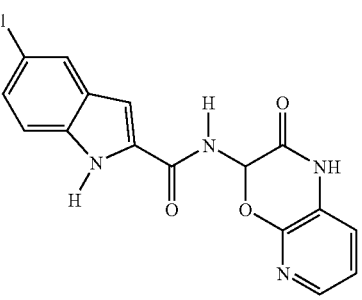
EXAMPLE 53
use Schemes 16 and 11
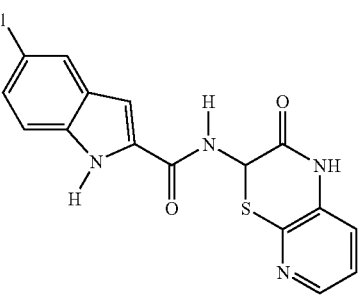

EXAMPLE 54 use Schemes 15 and 11

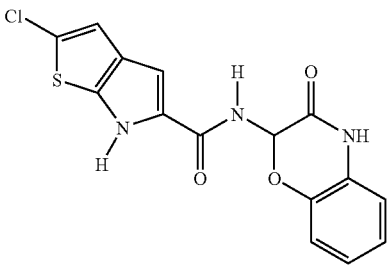

EXAMPLE 55 use Schemes 23, 22, and 11

EXAMPLE 56 racemate

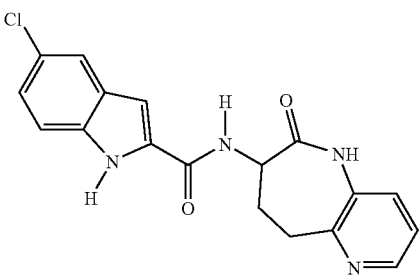

EXAMPLE 56

3-(5-chloroindole-2-carbonylamino)-2,3,4,5-tetrahydro-1H-pyrido[3,2-b]azepin-2-one To a solution of 2,3,4,5-tetrahydro-1H-pyrido[3,2-b]azepin-2-one (Jössang-Yanagida, et al., J. Het. Chem. 1978, 15, 249-251 and U.S. Pat. No. 5,719,278) (100 mg), N,N,N',N'tetramethylethylenediamine (215 mg), and iodotrimethylsilane (370 mg) in dichloromethane (1 mL) stirring under argon at 0° C. was added iodine (236 mg). After the starting material was consumed, the product, 3-iodo-2,3,4,5-tetrahydro-1H-pyrido[3,2-b]azepin-2-one, was purified by silica gel chromatography without prior solvent evaporation.

Thus obtained 3-iodo-2,3,4,5-tetrahydro-1H-pyrido[3,2-b]azepin-2-one (109 mg) was dissolved in 7 M methanolic ammonia solution (5 mL) at room temperature under argon. When the starting material was consumed, the mixture was evaporated under vacuum, and the residue was purified by silica gel chromatography to obtain 3-amino-2,3,4,5-tetrahydro-1H-pyrido[3,2-b]azepin-2-one.

The title compound was prepared from 3-amino-2,3,4,5-tetrahydro-1H-pyrido[3,2-b]azepin-2-one according to the Carbodiimide Mediated Amide Bond Formation Procedure with the following modifications: the reaction solvent was N,N-dimethylformamide-tetrahydrofuran (2:3), diisopropylethylamine was included, no attempt was made to hydrolyze any residual activated ester, no attempt was made to precipitate desired product, and the product was purified directly by reverse phase preparative HPLC. MS $[M+H]^+$, 355; $[M-H]^-$, 353.

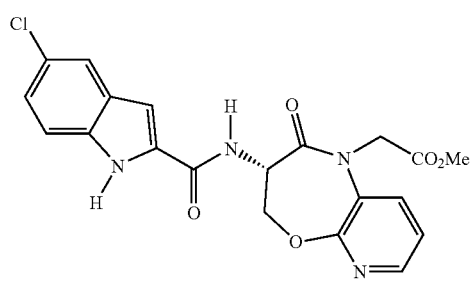

Example 57

EXAMPLE 57

(S)-9-aza-5-carbomethoxymethyl-3-(5-chloroindole-2-carbonylamino)-2,3-dihydro-1,5-benzoxazepin-4(5H)-one (S)-9-aza-3-(5-chloroindole-2-carbonylamino)-2,3-dihydro-1,5-benzoxazepin-4(5H)-one (Example 34) (15.3 mg) was dissolved in tetrahydrofuran (5 mL) at room temperature under argon. To the stirring solution was added sodium methoxide (4.6 mg), followed by methyl bromoacetate (13.2 mg). After 16 h, additional sodium methoxide (4.6 mg) was added and the resulting mixture was stirred for 3 h before acetic acid (1 mL) and water (1 mL) were added. The solvent was evaporated under vacuum, and the crude product was purified by reverse phase preparative HPLC to provide the title compound (13.4 mg). HPLC/MS $[M+H]^+$, 429.

What is claimed is:

1. A compound of the formula I

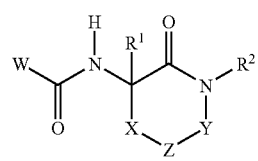

wherein

W is a bicyclic heteroaryl of the structure

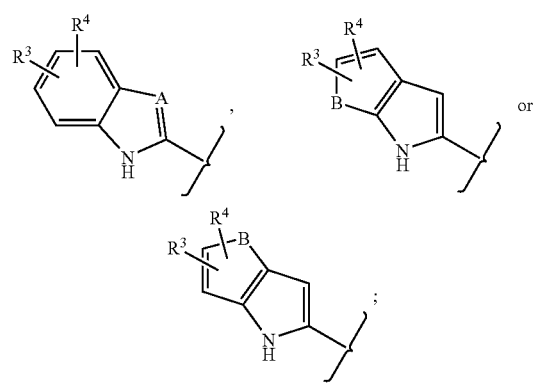

X is —$CHR^5O$—,

Y is a bond;

Z is an aryl or heteroaryl group of the following structure:

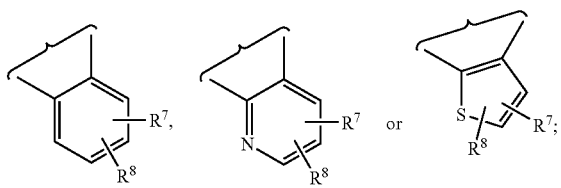

A is —CH— or —N—;
B is —O— or —S—;
R$^1$ is hydrogen, alkyl, aryl or alkenyl;
R$^2$ is hydrogen, alkyl, aryl, arylalkyl, heteroarylalkyl or alkenyl;
R$^3$ and R$^4$ are each independently hydrogen, halo, trifluoromethyl, cyano, alkyl or alkoxy;
R$^5$ and R$^6$ are each independently hydrogen, alkyl, aryl, alkenyl, CN, CN$_4$R$^{9A}$ (tetrazole), CO$_2$R$^{9A}$, CONR$^{9A}$R$^{9B}$ or CONR$^{9A}$OR$^{9B}$;
R$^7$ and R$^8$ are each independently hydrogen, halo, trifluoromethyl, cyano, hydroxy, a hydrogen bonding group, alkyl, alkoxy, aryl, arylalkyl, heteroarylalkyl, aryloxy or alkenyl; and
R$^{9A}$ and R$^{9B}$ are independently hydrogen, alkyl, arylalkyl, heteroarylalkyl or aryl, or R$^{9A}$ and R$^{9B}$ may optionally be cyclized together to form a ring, wherein said ring may further be substituted with one to three hydrogen bonding groups;
wherein when R$^1$, R$^2$, R$^5$, R$^6$, R$^7$ and R$^8$ are alkyl, aryl, alkenyl, arylalkyl, heteroarylalkyl, alkoxy or aryloxy, R$^1$, R$^2$, R$^5$, R$^6$, R$^7$ and R$^8$ may each independently be substituted with 1 to 3 hydrogen bonding groups;
wherein said hydrogen bonding group is selected from the group consisting of OR$^{9A}$, OCO$_2$R$^{10}$, OCONR$^{9A}$R$^{9B}$, CN, NO$_2$, CN$_4$R$^{9A}$ (tetrazole), COCF$_3$, COR$^{9A}$, CO$_2$R$^{9A}$, CONR$^{9A}$R$^{9B}$, CONR$^{9A}$OR$^{9B}$, C(NR$^{9A}$)NR$^{9B}$R$^{9C}$, CONR$^{9A}$SO$_2$R$^{9B}$, SOR$^{10}$, SO$_2$R$^{10}$, SO$_3$H, SO$_2$NR$^{9A}$R$^{9B}$, SO$_2$NR$^{9A}$COR$^{9B}$, SO$_2$NR$^{9A}$CONR$^{9B}$R$^{9C}$, POR$^{9A}$R$^{9B}$, PO$_2$R$^{9A}$R$^{9B}$, PO$_3$R$^{9A}$R$^{9B}$, PO$_2$R$^{9A}$NR$^{9B}$R$^{9C}$, NR$^{9A}$R$^{9B}$, NR$^{9A}$COR$^{9B}$, NR$^{9A}$C(NR$^{9B}$)R$^{9C}$, NR$^{9A}$CO$_2$R$^{9B}$, NR$^{9A}$CONR$^{9B}$R$^{9C}$, NR$^{9A}$C(NR$^{9B}$)NR$^{9C}$R$^{9D}$, NR$^{9A}$SO$_2$R$^{9B}$, NR$^{9A}$CONR$^{9A}$SO$_2$NR$^{9B}$R$^{9C}$, NR$^{9A}$POR$^{9B}$R$^{9C}$, NR$^{9A}$PO$_2$R$^{9B}$R$^{9C}$, NR$^{9A}$PO$_3$R$^{9B}$R$^{9C}$ and NR$^{9A}$PO$_2$R$^{9B}$NR$^{9C}$R$^{9D}$; wherein
R$^{9C}$ and R$^{9D}$ are each independently hydrogen, alkyl, arylalkyl, heteroarylalkyl or aryl; and
R$^{10}$ is independently alkyl, arylalkyl, heteroarylalkyl, or aryl;
wherein R$^{9A}$, R$^{9B}$, R$^{9C}$, R$^{9D}$ or R$^{10}$ may further be substituted with one to three hydrogen bonding groups;
and wherein
two of R$^{9A}$, R$^{9B}$, R$^{9C}$ or R$^{9D}$ within the same hydrogen bonding group may optionally be cyclized together to form a ring, wherein said ring may further be substituted with one to three hydrogen bonding groups as defined above;
or a pharmaceutically acceptable salt thereof.

2. The compound as defined in claim 1 wherein Z is an aryl or heteroaryl group of the structure

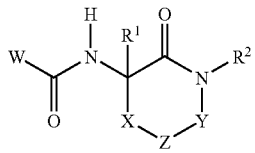

3. A pharmaceutical composition comprising a compound of formula I

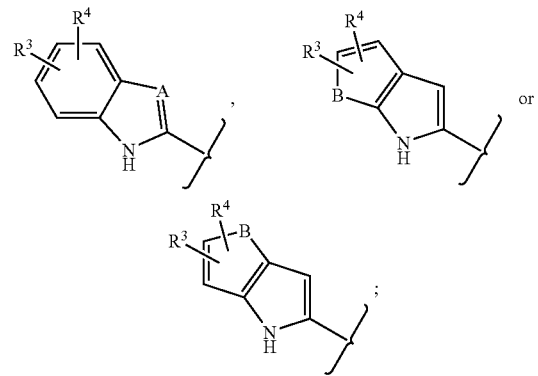

wherein
W is a bicyclic heteroaryl of the structure

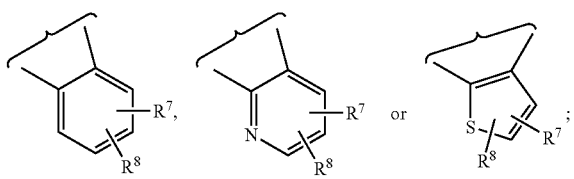

X is —CHR$^5$O—;
Y is a bond;
Z is an aryl or heteroaryl group of the following structure:

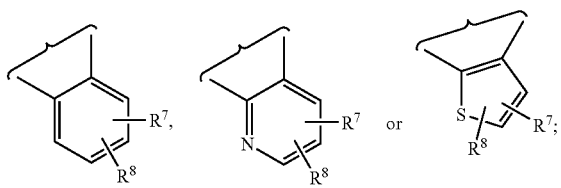

A is —CH— or —N—;
B is —O— or —S—;
R$^1$ is hydrogen, alkyl, aryl or alkenyl;
R$^2$ is hydrogen, alkyl, aryl, arylalkyl, heteroarylalkyl or alkenyl;
R$^3$ and R$^4$ are each independently hydrogen, halo, trifluoromethyl, cyano, alkyl or alkoxy;
R$^5$ and R$^6$ are each independently hydrogen, alkyl, aryl, alkenyl, CN, CN$_4$R$^{9A}$ (tetrazole), CO$_2$R$^{9A}$, CONR$^{9A}$R$^{9B}$ or CONR$^{9A}$OR$^{9B}$;

R[7] and R[8] are each independently hydrogen, halo, trifluoromethyl, cyano, hydroxy, a hydrogen bonding group, alkyl, alkoxy, aryl, arylalkyl, heteroarylalkyl, aryloxy or alkenyl; and R[9A] and R[9B] are independently hydrogen, alkyl, arylalkyl, heteroarylalkyl or aryl, or R[9A] and R[9B] may optionally be cyclized together to form a ring, wherein said ring may further be substituted with one to three hydrogen bonding groups, wherein when R[1], R[2], R[5], R[6], R[7] and R[8] are alkyl, aryl, alkenyl, arylalkyl, heteroarylalkyl, alkoxy or aryloxy, R[1], R[2], R[5], R[6], R[7] and R[8] may each independently be substituted with 1 to 3 hydrogen bonding groups;

wherein said hydrogen bonding group is selected from the group consisting of $OR^{9A}$, $OCO_2R^{10}$, $OCONR^{9A}R^{9B}$, $CN$, $NO_2$, $CN_4R^{9A}$ (tetrazole), $COCF_3$, $COR^{9A}$, $CO_2R^{9A}$, $CONR^{9A}R^{9B}$, $CONR^{9A}OR^{9B}$, $C(NR^{9A})NR^{9B}R^{9C}$, $CONR^{9A}SO_2R^{9B}$, $SOR^{10}$, $SO_2R^{10}$, $SO_3H$, $SO_2NR^{9A}R^{9B}$, $SO_2NR^{9A}COR^{9B}$, $SO_2NR^{9A}CONR^{9B}R^{9C}$, $POR^{9A}R^{9B}$, $PO_2R^{9A}R^{9B}$, $PO_3R^{9A}R^{9B}$, $PO_2R^{9A}NR^{9B}R^{9C}$, $NR^{9A}R^{9B}$, $NR^{9A}COR^{9B}$, $NR^{9A}C(NR^{9B})R^{9C}$, $NR^{9A}CO_2R^{9B}$, $NR^{9A}CONR^{9B}R^{9C}$, $NR^{9A}C(NR^{9B})NR^{9C}R^{9D}$, $NR^{9A}SO_2R^{9B}$, $NR^{9A}CONR^{9B}SO_2R^{9C}$, $NR^{9A}POR^{9B}R^{9C}$, $NR^{9A}PO_2R^{9B}R^{9C}$, $NR^{9A}PO_3R^{9B}R^{9C}$ and $NR^{9A}PO_2R^{9B}NR^{9C}R^{9D}$; wherein R[9C] and R[9D] are each independently hydrogen, alkyl, arylalkyl, heteroarylalkyl or aryl; and R[10] is independently alkyl, arylalkyl, heteroarylalkyl, or aryl;

wherein R[9A], R[9B], R[9C], R[9D] or R[10] may further be substituted with one to three hydrogen bonding groups;

and wherein two of R[9A], R[9B], R[9C] or R[9D] within the same hydrogen bonding group may optionally be cyclized together to form a ring, wherein said ring may further be substituted with one to three hydrogen bonding groups;

or a pharmaceutically acceptable salt thereof, and a pharmaceutically acceptable carrier therefor.

4. The pharmaceutical composition of claim 3 wherein

Z is an aryl or heteroaryl group of the structure

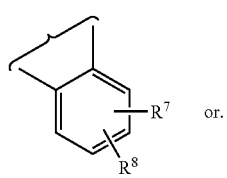

5. The pharmaceutical composition of claim 3 wherein

R[1] is hydrogen;

Z is

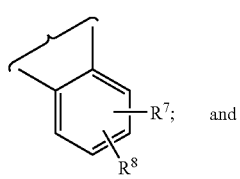

W is

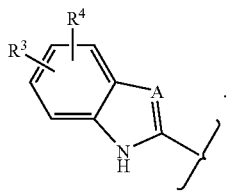

6. The pharmaceutical composition of claim 3 wherein Z is

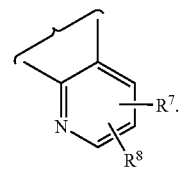

7. The pharmaceutical composition of claim 3 wherein W is 5-chloroindol-2-yl.

8. The pharmaceutical composition of claim 3 wherein

X is —CHR[5]O—;

Y is a bond; and

R[5] is $CO_2H$.

9. The pharmaceutical composition of claim 3 wherein the compound of formula I has the structure:

(S)-3-(5-chloroindole-2-carbonylamino)-2,3-dihydro-1,5-benzoxazepin-4(5H)-one;

(R)-3-(5-chloroindole-2-carbonylamino)-2,3-dihydro-1,5-benzoxazepin-4(5H)-one;

(2S,3S)-3-(5-chloroindole-2-carbonylamino)-2-methyl-2,3-dihydro-1,5-benzoxazepin-4(5H)-one;

(2S,3R)-3-(5-chloroindole-2-carbonylamino)-2-methyl-2,3-dihydro-1,5-benzoxazepin-4(5H)-one;

(S)-1-carboxymethyl-3-(5-chloroindole-2-carbonylamino)-2,3-dihydro-1,5-benzoxazepin-4(5H)-one;

(S)-9-aza-3-(5-chloroindole-2-carbonylamino)-2,3-dihydro-1,5-benzoxazepin-4(5H)-one;

(S)-7-aza-3-(5-chloroindole-2-carbonylamino)-2,3-dihydro-1,5-benzoxazepin-4(5H)-one.

10. The pharmaceutical composition of claim 3 comprising a compound of formula I and at least one anti-diabetic agent, an anti-obesity agent or a lipid lowering agent.

11. The pharmaceutical composition of claim 10 wherein the antidiabetic agent is at least one agent selected from the group consisting of a biguanide, a sulfonyl urea, a glucosidase inhibitor, a PPAR-alpha agonist, a PPAR-gamma agonist, a PPAR alpha/gamma dual agonist, an aP2 inhibitor, an SGLT2 inhibitor, a dipeptidyl peptidase-IV inhibitor, an insulin sensitizer, a thiazolidinedione, a glucagon-like peptide-1 (GLP-1), an aldose reductase inhibitor, a sorbitol dehydrogenase inhibitor, insulin and a meglitinide.

12. The pharmaceutical composition of claim 10 wherein the antidiabetic agent is at least one agent selected from the group consisting of metformin, glyburide, glimepiride, glipyride, glipizide, chlorpropamide, gliclazide, acarbose, miglitol, pioglitazone, troglitazone, rosiglitazone, insulin, Gl-262570, isaglitazone, JTT-501, NN-2344, L895645, YM-440, R-119702, AJ9677, repaglinide, nateglinide, KAD1129, AR-HO39242, GW-409544, KRP297, AC2993, LY315902 and NVP-DPP-728A.

13. The pharmaceutical composition of claim 10 wherein the anti-obesity agent is at least one agent selected from the group consisting of a beta 3 adrenergic agonist, a lipase inhibitor, a serotonin (and dopamine) reuptake inhibitor, a thyroid receptor beta compound and an anorectic agent.

14. The pharmaceutical composition of claim 10 wherein the anti-obesity agent is at least one agent selected from the group consisting of orlistat, ATL-962, AJ9677, L750355, CP331648, sibutramine, topiramate, axokine, dexamphetamine, phentermine, phenylpropanolamine and mazindol.

15. The pharmaceutical composition of claim 10 wherein the lipid lowering agent is at least one agent selected from the group consisting of an MTP inhibitor, cholesterol ester transfer protein, an HMG CoA reductase inhibitor, a squalene synthetase inhibitor, a fibric acid derivative, a cholesterol absorption inhibitor, an ileal Na+/bile cotransporter inhibitor, a bile acid sequestrant, a nicotinic acid derivative, an upregulator of LDL receptor activity, a lipoxygenase inhibitor and an ACAT inhibitor.

16. The pharmaceutical composition of claim 10 wherein the lipid lowering agent is at least one agent selected from the group consisting of pravastatin, lovastatin, simvastatin, atorvastatin, cerivastatin, fluvastatin, nisvastatin, visastatin, fenofibrate, gemfibrozil, clofibrate, avasimibe, TS-962, MD-700, CP-529414, and/or LY295427.

17. The pharmaceutical composition of claim 10 comprising a compound of formula I and at least one anti-hypertensive agent.

18. A method for treating diabetes, hyperglycemia, obesity, or glucose intolerance, which comprises administering to a mammalian patient in need of treatment a therapeutically effective amount of the pharmaceutical composition as defined in claim 3.

19. The method according to claim 18 further comprising administering, concurrently or sequentially, a therapeutically effective amount of at least one additional therapeutic agent selected from the group consisting of other compounds of formula I, anti-diabetic agents, anti-obesity agents, anti-hypertensive agents, anti-atherosclerotic agents, and lipid-lowering agents.

20. The method of claim 18 wherein
Z is an aryl or heteroaryl group of the structure

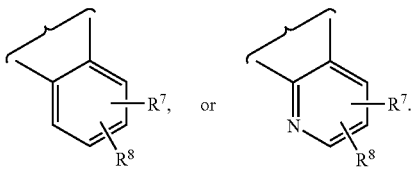

* * * * *

UNITED STATES PATENT AND TRADEMARK OFFICE
CERTIFICATE OF CORRECTION

PATENT NO. : 7,425,550 B2
APPLICATION NO. : 11/352867
DATED : September 16, 2008
INVENTOR(S) : Philip Sher et al.

Page 1 of 1

It is certified that error appears in the above-identified patent and that said Letters Patent is hereby corrected as shown below:

In the Claims:

Claim 1:

Column 74, line 66, change "," to -- ; --.

Column 75, line 50, change "$NR^{9A}CONR^{9A}SO_2NR^{9B}R^{9C}$," to -- $NR^{9A}CONR^{9B}SO_2R^{9C}$, $NR^{9A}SO_2NR^{9B}R^{9C}$, --.

Claim 3:

Column 77, line 24, after "$NR^{9A}CONR^{9B}SO_2R^{9C}$,", insert -- $NR^{9A}SO_2NR^{9B}R^{9C}$, --.

Claim 4:

Column 77, line 49, after "or", insert -- 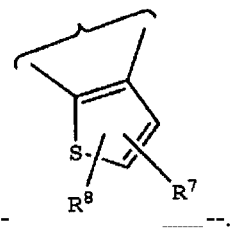 --.

Claim 20:

Column 80, line 23, delete ",".

Signed and Sealed this
Twenty-seventh Day of September, 2011

David J. Kappos
Director of the United States Patent and Trademark Office

UNITED STATES PATENT AND TRADEMARK OFFICE
CERTIFICATE OF CORRECTION

| | | |
|---|---|---|
| PATENT NO. | : 7,425,550 B2 | Page 1 of 1 |
| APPLICATION NO. | : 11/352867 | |
| DATED | : September 16, 2008 | |
| INVENTOR(S) | : Philip Sher et al. | |

It is certified that error appears in the above-identified patent and that said Letters Patent is hereby corrected as shown below:

On the Title Page:

Item (73) Assignee,

Change "Bristol-Meyers Squibb Company" to -- Bristol-Myers Squibb Company --.

Signed and Sealed this
Twenty-ninth Day of November, 2011

David J. Kappos
*Director of the United States Patent and Trademark Office*